(12) United States Patent
Millar et al.

(10) Patent No.: US 8,343,738 B2
(45) Date of Patent: Jan. 1, 2013

(54) ASSAY FOR SCREENING FOR POTENTIAL CERVICAL CANCER

(75) Inventors: Douglas Spencer Millar, Revesby (AU); John R. Melki, Dolls Point (AU); George L. Gabor Miklos, Newport (AU)

(73) Assignee: Human Genetic Signatures Pty. Ltd., North Ryde (AU)

( * ) Notice: Subject to any disclaimer, the term of this patent is extended or adjusted under 35 U.S.C. 154(b) by 367 days.

(21) Appl. No.: 12/066,644

(22) PCT Filed: Sep. 14, 2006
(Under 37 CFR 1.47)

(86) PCT No.: PCT/AU2006/001349
§ 371 (c)(1), (2), (4) Date: Oct. 2, 2008

(87) PCT Pub. No.: WO2007/030882
PCT Pub. Date: Mar. 22, 2007

(65) Prior Publication Data
US 2010/0041013 A1    Feb. 18, 2010

Related U.S. Application Data

(60) Provisional application No. 60/717,148, filed on Sep. 14, 2005.

(51) Int. Cl.
*C12P 19/34* (2006.01)
(52) U.S. Cl. .................................................... 435/91.2
(58) Field of Classification Search .................... None
See application file for complete search history.

(56) References Cited

U.S. PATENT DOCUMENTS

| | | | |
|---|---|---|---|
| 5,175,273 A | 12/1992 | Bischofberger et al. |
| 5,414,077 A | 5/1995 | Lin et al. |
| 5,418,149 A | 5/1995 | Gelfand et al. |
| 5,629,156 A | 5/1997 | Shah et al. |
| 5,656,744 A | 8/1997 | Arnold et al. |
| 5,750,338 A | 5/1998 | Collins et al. |
| 5,786,146 A | 7/1998 | Herman et al. |
| 5,824,517 A | 10/1998 | Cleuziat et al. |
| 5,952,174 A | 9/1999 | Nikiforov et al. |
| 6,156,501 A | 12/2000 | McGall et al. |
| 6,251,637 B1 | 6/2001 | Blusch |
| 6,265,171 B1 | 7/2001 | Herman et al. |
| 6,331,393 B1 | 12/2001 | Laird et al. |
| 6,420,106 B1 | 7/2002 | Gyllensten et al. |
| 6,521,411 B2 | 2/2003 | Hecker et al. |
| 6,692,918 B2 | 2/2004 | Kurn |
| 6,960,436 B2 | 11/2005 | Cottrell |
| 7,008,770 B1 | 3/2006 | Berlin |
| 7,288,373 B2 | 10/2007 | Millar et al. |
| 7,413,855 B2 | 8/2008 | Bergmann et al. |
| 7,504,207 B2 | 3/2009 | Bergquist et al. |
| 7,527,948 B2 | 5/2009 | Hudson et al. |
| 7,799,525 B2 | 9/2010 | Millar |
| 7,803,580 B2 | 9/2010 | Millar |
| 7,833,942 B2 | 11/2010 | Millar et al. |
| 7,846,693 B2 | 12/2010 | Millar et al. |
| 8,168,777 B2 | 5/2012 | Millar et al. |
| 2002/0086324 A1 | 7/2002 | Laird et al. |
| 2002/0142397 A1 | 10/2002 | Collas et al. |
| 2003/0073081 A1 | 4/2003 | Mukai et al. |
| 2003/0082600 A1 | 5/2003 | Olek et al. |
| 2003/0119025 A1 | 6/2003 | Olek et al. |
| 2003/0143577 A1 | 7/2003 | Hogrefe et al. |
| 2004/0067559 A1 | 4/2004 | McCarthy et al. |
| 2004/0086944 A1 | 5/2004 | Grigg et al. |
| 2004/0203004 A1 | 10/2004 | Bernard et al. |
| 2004/0219539 A1 | 11/2004 | Millar et al. |
| 2005/0019762 A1 | 1/2005 | Olek |
| 2005/0059003 A1 | 3/2005 | Enoki et al. |
| 2005/0118578 A1 | 6/2005 | Mineno et al. |
| 2005/0136417 A1 | 6/2005 | Cole et al. |
| 2005/0196392 A1 | 9/2005 | Andersen |
| 2005/0196792 A1 | 9/2005 | Fodor et al. |
| 2005/0202490 A1 | 9/2005 | Makarov |
| 2006/0014144 A1 | 1/2006 | Christensen et al. |
| 2006/0051771 A1 | 3/2006 | Murphy et al. |
| 2006/0068406 A1 | 3/2006 | Affholter et al. |
| 2006/0094009 A1 | 5/2006 | Vaughan et al. |
| 2006/0166203 A1 | 7/2006 | Took |
| 2006/0286576 A1 | 12/2006 | Lofton-Day |
| 2007/0020633 A1 | 1/2007 | Millar |
| 2007/0020639 A1 | 1/2007 | Millar |
| 2007/0020653 A1 | 1/2007 | Holliger et al. |
| 2007/0026070 A1 | 2/2007 | Vonwiller |

(Continued)

FOREIGN PATENT DOCUMENTS

DE    103 31 107 B3    12/2004

(Continued)

OTHER PUBLICATIONS

Bakker et al. JBC, vol. 277, No. 25, pp. 22573-22580, Jun. 2002.*
Lee et al., Cancer Epidemiology, Biomarkers, Prevention, vol. 6, pp. 443-450, Jun. 1997.*
Esteller te al., Cancer Research, vol. 58, pp. 4514-4518, Oct. 1998.*
Virmani et al., Clinical Cancer Research, vol. 7, No. 3, pp. 584-489, Mar. 2001.*
Melki et al., Cancer Research, vol. 59, pp. 3730-3740, Aug. 1999.*
Toyota et al., Cancer Research, vol. 59, pp. 4535-4541, Sep. 1999.*
Shao-Qing, Chinese journal of Agricultureal Biotechnology, vol. 4, No. 1, pp. 75-79, 2007.*
Pao et al., Human Molecular Genetics, vol. 10, No. 9, pp. 903-910, 2001.*
Cameron et al., Blood, vol. 94, No. 7, pp. 2445-2451, Oct. 1999.*
Tsuda et al., Gynecologic Oncology, vol. 91, pp. 476-485, 2003.*
European Search Report issued in corresponding European Application No. 06774977, dated Jul. 28, 2009.
Extended European Search Report issued in corresponding European Application No. 05779000.8, dated Dec. 4, 2008.

(Continued)

*Primary Examiner* — Gary Benzion
*Assistant Examiner* — Cynthia Wilder
(74) *Attorney, Agent, or Firm* — Knobbe Martens Olson & Bear LLP

(57) ABSTRACT

The invention relates to an assay for determining a health state of a subject using a combination of detecting the presence of a virus and detecting the presence of a genomic target or marker indicative of a health state.

13 Claims, 4 Drawing Sheets

U.S. PATENT DOCUMENTS

| | | | |
|---|---|---|---|
| 2007/0042365 | A1 | 2/2007 | Millar et al. |
| 2007/0065824 | A1 | 3/2007 | Gutig |
| 2007/0178457 | A1 | 8/2007 | Millar |
| 2007/0178459 | A1 | 8/2007 | Millar |
| 2007/0190530 | A1 | 8/2007 | Birkner et al. |
| 2007/0264653 | A1 | 11/2007 | Berlin et al. |
| 2008/0050738 | A1 | 2/2008 | Millar |
| 2009/0029346 | A1 | 1/2009 | Millar et al. |
| 2009/0042732 | A1 | 2/2009 | Millar |
| 2009/0130657 | A1 | 5/2009 | Millar |
| 2009/0263909 | A1 | 10/2009 | Millar |
| 2010/0041013 | A1 | 2/2010 | Millar et al. |
| 2010/0092972 | A1 | 4/2010 | Millar et al. |
| 2010/0121056 | A1 | 5/2010 | Christensen et al. |
| 2010/0221785 | A1 | 9/2010 | Millar et al. |
| 2010/0286379 | A1 | 11/2010 | Millar et al. |
| 2010/0304386 | A1 | 12/2010 | Millar |
| 2011/0003700 | A1 | 1/2011 | Millar |
| 2011/0136098 | A1 | 6/2011 | Millar et al. |
| 2012/0021461 | A1 | 1/2012 | Millar et al. |

FOREIGN PATENT DOCUMENTS

| | | | |
|---|---|---|---|
| EP | 1 130 113 | | 9/2001 |
| EP | 1 319 718 | | 6/2003 |
| EP | 1443052 | | 8/2004 |
| EP | 1 801 213 | A2 | 6/2007 |
| WO | WO 95/01456 | | 1/1995 |
| WO | WO 95/22623 | | 8/1995 |
| WO | WO 97/41254 | | 11/1997 |
| WO | WO 97/45559 | | 12/1997 |
| WO | WO 98/20157 | | 5/1998 |
| WO | WO 98/29108 | | 7/1998 |
| WO | WO 99/09211 | A2 | 2/1999 |
| WO | WO 99/14226 | | 3/1999 |
| WO | WO 99/49081 | A2 | 9/1999 |
| WO | WO 00/44934 | | 8/2000 |
| WO | WO 00/50869 | A2 | 8/2000 |
| WO | WO 01/09374 | A2 | 2/2001 |
| WO | WO 01/38565 | A2 | 5/2001 |
| WO | WO 01/42493 | A2 | 6/2001 |
| WO | WO 01/76451 | A2 | 10/2001 |
| WO | WO 02/36821 | A2 | 5/2002 |
| WO | WO 02/38801 | | 5/2002 |
| WO | WO 02/46452 | | 6/2002 |
| WO | WO 02/072880 | | 9/2002 |
| WO | WO 02/097065 | | 12/2002 |
| WO | WO 03/008623 | A2 | 1/2003 |
| WO | WO 03/048732 | | 6/2003 |
| WO | WO 03/051901 | A2 | 6/2003 |
| WO | WO 03/052132 | A2 | 6/2003 |
| WO | WO 03/052133 | A2 | 6/2003 |
| WO | WO 03/052134 | A2 | 6/2003 |
| WO | WO 2004/015139 | | 2/2004 |
| WO | WO 2004/065625 | | 8/2004 |
| WO | WO 2004/090166 | | 10/2004 |
| WO | WO 2004/090166 | A | 10/2004 |
| WO | WO 2004/096825 | | 11/2004 |
| WO | WO 2004/111266 | | 12/2004 |
| WO | WO 2005/021778 | | 3/2005 |
| WO | WO 2005/056790 | A1 | 6/2005 |
| WO | WO 2005/113760 | A2 | 12/2005 |
| WO | WO 2006/058393 | | 6/2006 |
| WO | WO 2006/066353 | | 6/2006 |
| WO | WO 2006/113770 | A1 | 10/2006 |
| WO | WO 2007/106802 | A2 | 9/2007 |
| WO | WO 2008/109945 | | 9/2008 |
| WO | WO 2008/135512 | A2 | 11/2008 |
| WO | WO 2009/067743 | | 6/2009 |
| WO | WO 2009/070843 | | 6/2009 |
| WO | WO 2009/079703 | | 7/2009 |

OTHER PUBLICATIONS

Extended European Search Report issued in corresponding European Application No. 05821631.8, dated Nov. 7, 2008.

Extended European Search Report issued in corresponding European Application No. 05821631.8, dated Oct. 16, 2008.

Gu W. et al, Depletion of *Saccharomyces cerevisiae* tRNAHis Guanylyltransferase Thglp leads to uncharged tRNAH is with additional m5C, Mol Cell Biol. Sep. 2005; vol. 25, No. 18, pp. 8191-8201.

International Search Report issued for corresponding PCT Application No. PCT/AU2006/000755, dated Aug. 30, 2006.

International Search Report issued on corresponding PCT Application No. PCT/AU2008/000367, dated May 14, 2008.

Kalantari, Mina et al. "Conserved methylation patterns of human papillomavirus type 16 DNA in asymptomatic infection and cervical neoplasia," Journal of Virology, vol. 78, No. 23, Dec. 2004, pp. 12762-12772.

Kozak et al.: "Influence of secondary structure on binding and migration of 40S ribosomal subunits," Cell; vol. 19, 1980, pp. 79-90.

Nilsson et al., "Padlock Probes: Circularizing Oligonucleotides for localized DNA Detection", Science; 265:2085-2088 (1994).

Nousbaum, J. et al., "Prospective Characteristics of Full-Length Hepatitis C Virus NS5A Quasispecies during Induction and Combination Antiviral Therapy," Journal of Virology, 74, No. 19, pp. 9028-9038 (2000).

Office Action in U.S. Appl. No. 10/543,017 dated Dec. 8, 2008.

Office Action in U.S. Appl. No. 10/543,017 dated Jun. 20, 2008.

Office Action in U.S. Appl. No. 10/543,017 dated Oct. 19, 2007.

Office Action in U.S. Appl. No. 11/573,873 dated May 4, 2009.

Office Action in U.S. Appl. No. 11/573,873 dated Sep. 2, 2009.

Office Action in U.S. Appl. No. 11/660,586 dated Sep. 15, 2009.

Raizis et al., "A Bisulfite method of 5-methylcytosine mapping that minimizes template degradation", Anal. Biochem., 226: 161-166 (1995).

Ratushna V.G. et al.: "Secondary structure in the target as a confounding factor in synthetic oligomer microarray design," BMC Genomics, vol. 6, No. 1, Mar. 2005, p. 31.

Supplementary European Search Report issued on corresponding European Patent Application No. EP 05 81 3335, dated Mar. 12, 2009.

Yanagi et al., "Hepatitis C Virus: An Infectious Molecular Clone of a Second Major Genotype (2A) and Lack of Viability of Intertypic 1A and 2A Chimeras," Virology 262, pp. 250-263 (1999).

Zeschnigk et al., "A novel real-time PCR assay for quantitative analysis of methylated alleles (QAMA): analysis of the retinoblastoma locus," Nucleic Acid Research 2004, vol. 32, No. 16, pp. 1-5.

Widschwendter et al: "Analysis of aberrant DNA methylation and human papillomavirus DNA in cervicovaginal specimens to detect invasive cervical cancer and its precursors" Clinical Cancer Research, The American Association for Cancer Research, US, vol. 10, No. 10, May 15, 2004, pp. 3396-3400.

Badal Sushma et al: "The human papillomavirus-18 genome is efficiently targeted by cellular DNA methylation" Virology, vol. 324, No. 2, Jul. 1, 2004, pp. 483-492.

Badal V. et al: "CpG methylation of human papillomavirus type 16 DNA in cervical cancer cell lines and in clinical specimens: Genomic hypomethylation correlates with carcinogenic progression" Journal of Virology, The American Society for Microbiology, US, vol. 77, No. 11, Jun. 1, 2003, pp. 6227-6234.

Feng et al: "Detection of hypermethylated genes in women with and without cervical neoplasia." Journal of the National Cancer Institute Feb. 16, 2005, vol. 97, No. 4, Feb. 16, 2005, pp. 273-282.

Narayan Gopeshwar et al: "Frequent Promoter Methylation of CDH1, DAPK, RARB, and HIC1 Genes in Carcinoma of Cervix Uteri: Its Relationship to Clinical Outcome" Molecular Cancer, Biomed Central, London, GB, vol. 2, No. 1, May 13, 2003, p. 24.

Kim T Y et al: "DNA hypermethylation in gastric cancer" Alimentary Pharmacology & Therapeutics, vol. 20, No. Suppl. 1, Jul. 2004, pp. 131-142.

Eads C A et al: "MethyLight: a high-throughput assay to measure DNA methylation" Nucleic Acids Research, Oxford University Press, Surrey, GB, vol. 28, No. 8, Apr. 15, 2000, pp. E32.1-E32.8.

Malyukova A V et al: "Methylation of the Putative Tumor Suppressor Gene RASSF1A in Primary Cervical Tumors" Molecular Biology, Kluwer Academic Publishers-Plenum Publishers, NE, vol. 38, No. 6, Nov. 1, 2004, pp. 857-864.

Verma M: "Viral genes and methylation" Annals of the New York Academy of Sciences 200303 US, vol. 983, Mar. 2003, pp. 170-180.

Baleriola C et al: "Comparison of a novel HPV test with the Hybrid Capture II (hcII) and a reference PCR method shows high specificity and positive predictive value for 13 high-risk human papillomavirus infections" Journal of Clinical Virology, Elsevier, Amsterdam, NL, vol. 42, No. 1, May 1, 2008, pp. 22-26.
Ushijima Toshikazu et al: "Aberrant methylations in cancer cells: Where do they come from?" Cancer Science, vol. 96, No. 4, Apr. 2005, pp. 206-211.
The European Search Report issued in corresponding European Application No. 06774977, dated Jul. 28, 2009.
Christensen et al., "Intercalating nucleic acids containing insertions of 1-o-(1-pyrenylmethyl)glycerol: stabilization of dsDNA and discrimination of DNA over RNA." Nucleic Acid Res. vol. 30, No. 22, pp. 4918-4925, (2002).
Clark et al., "High sensitivity mapping methylated cytosines." Nucleic Acids Research, 22(15): 2990-2997 (1994).
Clark, et al., "Bisulphite genomic sequencing of methylated cytosines." Laboratory Methods for the Detection of Mutations and Polymorphisms in DNA. Graham R. Taylor, Ed. CRC Press, New York (1997), pp. 151-162.
NCBI Database Accession No. M24485, Dec. 5, 1994.
Dean et al., "Comprehensive human genome amplification using multiple displacement amplification." PNAS, 99(8): 5261-5266 (2002).
Eads et al., "MethyLight: a high-throughput assay to measure DNA methylation." Nucleic Acids Research, 28(8): e32 i-viii (2000).
Feil, et al., "Methylation analysis on individual chromosomes: improved protocol for bisulphite genomic sequencing." (1994) Nucleic Acids Research 22(4): 695-696.
Frommer et al., "A genomic sequencing protocol that yields a positive display of 5-methylcytosine residues in individual DNA strands," Proc. Natl. Acad. Sci. 89: 1827-1831 (1992).
Grigoriev et al., "A Triple Helix-forming Oligonucleotide-Intercalator Conjugate Acts as a Transcriptional Repressor via Inhibition of NFkB Binding to Interleukin-2 Receptor a-Regulatory Sequence." The Journal of Biological Chemistry, 267 (5): 3389-3395 (1992).
Grunau, et al., "Bisulfite genomic sequencing: systematic investigation of critical experimental parameters." Nucleic Acids Research, (2001) vol. 29, No. 13e65, pp. 1-7.
Hakelien et al., "Reprogramming fibroblasts to express T-cell functions using cell extracts." Nature Briotechnology, 20(5): 460-466 (2002).
Hakelien et al., "Novel Approaches to Transdifferentation" Cloning and Stem Cells, 4: 379-387 (2002).
Herman, et al., "Methylation-specific PCR: a novel PCR assay for methylation status of CpG islands." (1996) Proc. Natl. Acad. Sci. 93:9821-9826.
Hosono et al. "Unbiased Whole-Genome Amplification Directly from Clinical Samples." *Genome Research;* 13:954-964 (2003).
International Human Genome Sequencing Consortium, "Initial sequencing and analysis of the human genome," Nature, 409(6822): 860-921 (2001).
International Preliminary Report on Patentability issued on the corresponding PCT Application No. PCT/AU2006/000698, dated Apr. 20, 2007.
International Search Report Issued on the corresponding PCT Application No. PCT/AU2006/000698, dated Aug. 1, 2006.
Kinoshita et al., "Methylation of the androgen receptor minimal promoter silences transcription in human prostate cancer." Cancer Research, 60(13): 3623-3630 (Jul. 1, 2000).
Kono, "Nuclear transfer and reprogramming." Reviews of Reproduction, vol. 2 No. 2, pp. 74-80 (May 1997).
Millar et al., "A distinct sequence (ATAAA)n separates methylated and unmethylated domains at the 5'-end of the GSTPI CpG island," J. Biol. Chem., 275(32): 24893-24899 (2000).
Millar et al., "Detailed methylation analysis of the glutathione S-transferase pi (GSTPI) gene in prostate cancer," Oncogene 18(6): 1313-1324 (1999).
Monk, "Epigentic programming of differential gene expression in development and evolution" Dev. Genetics, vol. 17, pp. 183-197 (1995).
Newton et al., "The production of PCR products with 5' single-stranded tails using primers that incorporate novel phosphoramidite intermediates." Nucleic Acid Res. vol. 21 No. 5, pp. 1155-1162 (1993).

Office Action in U.S. Appl. No. 10/428,310 dated Aug. 31, 2006.
Office Action in U.S. Appl. No. 10/428,310 dated Jan. 4, 2006.
Office Action in U.S. Appl. No. 10/428,310 dated Jul. 5, 2006.
Office Action in U.S. Appl. No. 10/428,310 dated Nov. 3, 2006.
Office Action in U.S. Appl. No. 10/536,633 dated Apr. 4, 2007.
Office Action in U.S. Appl. No. 10/536,633 dated Jan. 25, 2007.
Okada, et al., "Sequence Determination of Rat U5 RNA Using a Chemical Modification Procedure for Counteracting Sequence Compression." (1982) J. Biochem. 91: 1281-1291.
Olek, et al. "A modified and improved method for bisulphate based cytosine methylation analysis." (1996) Nucleic Acids Research, 24(24): 2065-5066.
Paulin et al., "Urea improves efficiency of bisulphite-mediated sequencing of 5'-methylcytosine in genomic DNA." Nucleic Acid Research, 26(21): 5009-5010 (Nov. 1, 1998).
Pietrobono et al., "Quantitative analysis of DNA demethylation and transcriptional reactivation of the FMR1 gene in fragile X cellstreated with 5-azadeoxycytidine." Nucleic Acids Research, 30(14): 3278-3285 (2002).
Rein et al., "Identifying 5-methylcytosine and related modifications in DNA genomes." Nucleic Acids Research, 26 (10): 2255-2264 (May 15, 1998).
Robertson et al., "Methylation of the Epstein-Barr Virus Genome in normal Lymphocytes", Blood, 90: 4480-4484 (1997).
Robertson et al. "DNA methylation: past, present, and future directions." Carcinogenesis. 21(3): 461-467 (2000).
Sakaguchi et al. "Cautionary Note on the Use of dUMP-Containing PCR Primers with *Pfu* and Vent$_R$® DNA Polymerases." *Biotechniques;* 21(3):368 & 370 (1996).
Sakashita et al., "Dynamic DNA methylation change in the CpG island region of p15 during human myeloid development", J. Clin. Invest., 108: 1195-1204 (2001).
Shapiro et al., "Deamination of cytosine derivatives by bisulfite. Mechanism of the reaction," J. Am. Chem. Soc., 96: 906-912 (1974).
Specification and Preliminary Amendment from co-pending U.S. Appl. No. 10/555,465, filed Aug. 28, 2006.
Tada et al., "Embryonic germ cells induce epigenetic reprogramming of somatic nucleus in hybrid cells." The EMBO Journal, 16(21): 6510-6520 (1997).
Telenius et al. "Degenerate Oligonucleotide-Primed PCR: General Amplification of Target DNA by a Single Degenerate Primer." *Genomics;* 13(3):718-725 (1992).
Tohgi et al., "Decrease with age in methylcytosines in the promoter region of receptor for advanced glycated end products (RAGE) gene in autopsy human cortex", Molecular Brain Research, 65:124-128 (1999).
Venter et al., "The sequence of the human genome," Science, 291 (5523): 1304-1351.
Waranecke et al., "Detection and measurement of PCR bias in quantitative methylation analysis of bisulphite-treated DNA," Nucleic Acids Research, vol. 25 No. 21, pp. 4422-4426, (1997).
Xiong et al., "COBRA: a sensitive and quantitative DNA methylation assay." (1997) Nucleic Acids Research, 25 (12): 2532-2534.
Cohen, Y. et al, "Hypermethylation of CpG Island Loci of Multiple Tumor Suppressor Genes in Retinoblastoma", Experimental Eye Research, 2008, vol. 86, No. 2, pp. 201-206.
Cottrell et al., A real-time PCR assay for DNA-methylation-specific blockers. Nucleic Acid Research, 32(1):e10 (8 pages). Jan. 13, 2004.
Hitchcock, T.M. et al, "Cleavage of deoxyoxadenosine-containing oligodeoxyribonucleotides by bacterial endonuclease V", Nucleic Acids Research, 2004, vol. 32, No. 13, pp. 4071-4080.
International Preliminary Report on Patentability corresponding to PCT Application No. PCT/AU2008/000367, dated May 6, 2009.
International Search Report issued in corresponding PCT Application No. PCT/AU2008/001891, mailed Feb. 3, 2009.
International Search report issued in PCT Application No. PCT/AU2008/001751, mailed Feb. 18, 2009.
International Search report issued in PCT Application No. PCT/AU2008/001796, mailed Feb. 23, 2009.
Longo, M.C. et al., "Use of Uracil DNA Glycosylase to Control Carry-Over Contamination in Polymerase Chain Reactions", Gene, vol. 93, No. I, pp. 125-128, Sep. 1990.

Munson, K. et al. Recovery of bisulphite-converted genomic sequences in the methylation-sensitive QPCR. Nucleic Acids Research (2007) vol. 35, No. 9, pp. 2893-2903.
Notice of Allowance issued in U.S. Appl. No. 10/561,029 dated May 28, 2010.
Office Action in U.S. Appl. No. 10/561,029 dated Apr. 13, 2009.
Office Action in U.S. Appl. No. 11/573,873 dated Mar. 23, 2010.
Office Action in U.S. Appl. No. 11/660,586 dated Apr. 15, 2010.
Office Action in U.S. Appl. No. 11/756,534 dated Aug. 10, 2009.
Office Action in U.S. Appl. No. 11/756,534 dated Jun. 8, 2010.
Shibutani, S. et al., "Translesional Synthesis on DNA Templates Containing a Single Abasic Site", The Journal of Biological Chemistry, 1997; vol. 272, No. 21, pp. 13916-13922.
Shiraishi, M. et al. High Speed Conversion of Cytosine to Uracil in Bisulphite Genomic Sequencing Analysis of DNA Methylation; DNA Research (2004) vol. II, pp. 409-415.
Stratagene, 1988 Catalog, p. 39.
Triplett, J. W. et al., Carbon-13 NMR Investigation of the bisulphite induced changes in yeast RNA; Biochemical and Biophysical Research Communications (1977), vol. 77, No. 4, pp. 1170-1175.
Yao, M. et al, "Further Characterization of *Escherichia coli* Endonuclease V", Journal of Biological Chemistry, 1997, vol. 272, No. 49, pp. 30774-30779.
Notice of Allowance issued in U.S. Appl. No. 11/575,060, mailed Jun. 15, 2010.
Notice of Allowance issued in U.S. Appl. No. 11/573,873, mailed Jul. 1, 2010.
Asseline et al. Synthesis and binding properties of oligonucleotides covalently linked to an acridine derivative: New study of the influence of the dye attachment site. *Bioconjugate Chem.*, 7:369-379 (1996).
Bleczinski et al. Steroid-DNA interactions increasing stability, sequence-selectivity, DNA/RNA discrimination, and hypochromicity of oligonucleotide duplexes. *J. Am. Chem. Soc.* 121:10889-10894 (1999).
Burmeister et al. Synthesis of novel phosphoramidite derivatives bearing pyrenyl and dansyl groups. *Tetrahedron Letters.* 36(21):3667-3668 (1995).
Christensen et al. Intercalating nucleic acids containing insertions of 1-0(1-pyrenylmethyl) glycerol: stabilisation of dsDNA and discrimination of DNA over RNA. *Nucleic Acids Research.* 30(22):4918-4925 (2002).
D'Abbadie, et al., "Molecular Breeding of Polymerases for Amplification of Ancient DNA," *Nature Biotechnology*, (Aug. 2007) 25:939-943.
De Mesmaeker et al. Amide backbone modifications for antisense oligonucleotides carrying potential intercalating substituents: Influence on the thermodynamic stability of the corresponding duplexes with RNA- and DNA-complements. *Bioorganic & Medicinal Chemistry Letters.* 7(14):1869-1874 (1997).
Francois et al. Recognition of hairpin-containing single-stranded DNA by oligonucleotides containing internal acridine derivatives. *Bioconjugate Chern.*, 1999, 10:439-446.
Herman et al. UNIT 10.6 Methylation-Specific PCR, Current Protocols in Human Genetics, Published Online: May 1, 2001, pp. 10.6.1-10.6.10, DOI: 10.1002/0471142905.hg1006s16, Copyright @ 2003 by John Wiley and Sons, Inc: http://onlinelibrary.wiley.com/doi/10.1002/0471142905.hg1006s16/full.
Korshun et al. Reagent for introducing pyrene residues in oligonucleotides. *Bioconjugate Chern.*, 1992, 3:559-562.
Mann et al. Synthesis and properties of an oligodeoxynucleotide modified with a pyrene derivative at the 5'-phosphate. *Bioconjugate Chern.*, 1992, 3:554-558.
Masuko, et al. Fluorescence resonance energy transfer from pyrene to perylene labels for nucleic acid hybridization assays under homogeneous solution conditions. *Nucleic Acids Research*, 28(8):e34, 8 pages (2000).
Paris, et al. Probing DNA sequencs in solution with a monomer-excimer fluorescence color change. *Nucleic Acids Research*, 26(16):3789-3793 (1998).
Timofeev et al. Methidium intercalator inserted into synthetic oligonucleotides. *Tetrahedron Letters.* 37(47):8467-8470 (1996).

Toulme et al. Specific inhibition of Mrna translation by complementary oligonucleotides covalently linked to intercalating agents. *Proceedings of the National Academy of Sciences of USA.* 83:1227-1231 (1986).
Wang et al. Comparison of bisulfite modification of 5-methyldeoxycytidine and deoxycytidine residues, Nucleic Acids Research, vol. 8 No. 20, pp. 4777-4790, (1980).
Yamana et al. Synthesis and properties of oligonucleotides bearing a pendant pyrene group. *Nucleic Acids Research.* 16:169-172 (1985).
Yamana et al. Oligonucleotides having covalently linked anthracene at specific sugar residue: Differential binding to DNA and RNA and fluorescence properties. *Tetrahedron Letters.* 36(46):8427-8430 (1995).
Yamana et al. Incorporation of two anthraquinonylmethyl groups into the 2'-O-positions of oligonucleotides: Increased affinity and sequence specificity of anthraquinone-modified oligonucleotides in hybrid formation with DNA and RNA. *Bioconjugate Chem.*, 7:715-720 (1996).
Yamana et al. Synthesis of oligonucleotide derivatives containing pyrene labeled glycerol linkers: enhanced excimer fluorescence on binding to a complementary DNA sequence. *Tetrahedron Letters.* 38(34): 6051-6054 (1997).
Yamana et al. 2'-Pyrene modified oligonucleotide provides a highly sensitive fluorescent probe of RNA. *Nucleic Acids Research.* 27(11):2387-2392 (1999).
International Search Report issued in PCT Application No. PCT/AU2004/000083, mailed Feb. 24, 2004.
International Search Report issued in PCT Application No. PCT/AU2004/000549, mailed Jul. 23, 2004.
International Search Report issued in PCT Application No. PCT/AU2004/000722, mailed Jun. 29, 2004.
International Search Report issued in PCT Application No. PCT/AU2004/001196, mailed Sep. 27, 2004.
Extended European Search Report issued on Dec. 2, 2010 in European Patent Application No. EP 08853330.2.
Office Action in U.S. Appl. No. 10/561,029 dated Dec. 8, 2009.
Office Action in U.S. Appl. No. 10/555,465 dated Oct. 1, 2008.
Notice of Abandonment in U.S. Appl. No. 10/555,465 dated Jun. 2, 2009.
Notice of Allowance in U.S. Appl. No. 10/428,310 dated May 24, 2007.
Notice of Allowance in U.S. Appl. No. 10/428,310 dated Sep. 21, 2007.
Office Action in U.S. Appl. No. 12/413,380 dated Mar. 11, 2011.
Office Action in U.S. Appl. No. 12/413,380 dated Nov. 3, 2011.
Notice of Allowance in U.S. Appl. No. 12/413,380 dated Jan. 9, 2012.
Office Action in U.S. Appl. No. 10/416,637 dated May 4, 2006.
Notice of Abandonment in U.S. Appl. No. 10/416,637 dated Jun. 15, 2007.
Office Action in U.S. Appl. No. 10/499,479 dated Dec. 20, 2006.
Office Action in U.S. Appl. No. 10/499,479 dated Apr. 19, 2007.
Office Action in U.S. Appl. No. 10/499,479 dated Jan. 3, 2008.
Office Action in U.S. Appl. No. 10/499,479 dated May 2, 2008.
Office Action in U.S. Appl. No. 10/499,479 dated May 30, 2008.
Office Action in U.S. Appl. No. 10/499,479 dated Feb. 5, 2009.
Notice of Abandonment in U.S. Appl. No. 10/499,479 dated Nov. 6, 2009.
Office Action in U.S. Appl. No. 12/534,743 dated May 14, 2010.
Notice of Abandonment in U.S. Appl. No. 12/534,743 dated Jan. 5, 2011.
Office Action in U.S. Appl. No. 11/660,586 dated Aug. 6, 2010.
Office Action in U.S. Appl. No. 11/660,586 dated Jul. 20, 2011.
Notice of Abandonment in U.S. Appl. No. 11/660,586 dated Mar. 7, 2012.
Notice of Abandonment in U.S. Appl. No. 10/536,633 dated Jan. 18, 2008.
Office Action in U.S. Appl. No. 11/919,443 dated Feb. 2, 2012.
Office Action in U.S. Appl. No. 11/919,443 dated May 29, 2012.
Office Action in U.S. Appl. No. 10/543,017 dated Aug. 8, 2007.
Notice of Abandonment in U.S. Appl. No. 10/543,017 dated Jun. 26, 2009.
Office Action in U.S. Appl. No. 10/570,715 dated Dec. 14, 2009.
Office Action in U.S. Appl. No. 10/570,715 dated Apr. 15, 2010.

Notice of Allowance in U.S. Appl. No. 10/570,715 dated Jul. 30, 2010.
Office Action in U.S. Appl. No. 11/756,534 dated Feb. 22, 2010.
Office Action in U.S. Appl. No. 11/756,534 dated Oct. 20, 2010.
Notice of Abandonment in U.S. Appl. No. 11/756,534 dated May 12, 2011.
Office Action in U.S. Appl. No. 12/531,482 dated Jan. 17, 2012.
Notice of Abandonment in U.S. Appl. No. 12/227,962 dated Sep. 28, 2011.
Office Action in U.S. Appl. No. 12/747,483 dated Feb. 28, 2012.
Office Action in U.S. Appl. No. 12/747,483 dated Jun. 26, 2012.

* cited by examiner

Human GST PCR

HR-HPV PCR

Human GST PCR

HR-HPV PCR

Human GST PCR

HR-HPV PCR

SEQUENCE LISTING

<160> NUMBER OF SEQ ID NOS: 86

<210> SEQ ID NO 1
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 1
tatgtatgga gatatarrta tattgt                                          26

<210> SEQ ID NO 2
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 2
gttatgagta attaaatgat agttt                                           25

<210> SEQ ID NO 3
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 3
taaaacacac aattcctaat atac                                            24

<210> SEQ ID NO 4
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 4
cccattaata cctacaaaat caac                                            24

<210> SEQ ID NO 5
<211> LENGTH: 27
<212> TYPE: DNA
<213> ORGANISM: Artificial Sequence
<220> FEATURE:

```
<223> OTHER INFORMATION: Oligonucleotide primer

<400> SEQUENCE: 5
gaaagttatt atagttatgt atagagt                                    27

<210> SEQ ID NO 6
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 6
attagaatgt gtgtattgta agtaat                                     26

<210> SEQ ID NO 7
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 7
actacaatat aaatatatct ccatac                                     26

<210> SEQ ID NO 8
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 8
aaactatcat ttaattactc ataac                                      25

<210> SEQ ID NO 9
<211> LENGTH: 31
<212> TYPE: DNA
<213> ORGANISM: Artificial Sequence
<220> FEATURE:
<223> OTHER INFORMATION: Oligonucleotide primer

<400> SEQUENCE: 9
gaatatattt tgtgtagttt aaagatgatg t                               31

<210> SEQ ID NO 10
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 10
gttttatatt tgtgtttagt agt                                        23

<210> SEQ ID NO 11
<211> LENGTH: 31
<212> TYPE: DNA
<213> ORGANISM: Artificial Sequence
<220> FEATURE:
<223> OTHER INFORMATION: Oligonucleotide primer

<400> SEQUENCE: 11
ccttttaaat atactataaa tataatatta c                               31

<210> SEQ ID NO 12
```

```
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 12
cacacaatat acaatataca atac                                          24

<210> SEQ ID NO 13
<211> LENGTH: 28
<212> TYPE: DNA
<213> ORGANISM: Artificial Sequence
<220> FEATURE:
<223> OTHER INFORMATION: Oligonucleotide primer

<400> SEQUENCE: 13
gtatggattt aaggtaatat tgtaagat                                      28

<210> SEQ ID NO 14
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 14
gtatttagag ttttaaaatg aaattt                                        26

<210> SEQ ID NO 15
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 15
aacacacaaa aaacaaaata ttc                                           23

<210> SEQ ID NO 16
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 16
accattatta cttactacta aaatac                                        26

<210> SEQ ID NO 17
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 17
gatagtatat agtatgttgt atgtt                                         25

<210> SEQ ID NO 18
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 18
```

```
atttagattt tgtgtatgga gatat                                          25

<210> SEQ ID NO 19
<211> LENGTH: 28
<212> TYPE: DNA
<213> ORGANISM: Artificial Sequence
<220> FEATURE:
<223> OTHER INFORMATION: Oligonucleotide primer

<400> SEQUENCE: 19
atcttacaat attaccttaa atccatac                                       28

<210> SEQ ID NO 20
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 20
aaatttcatt ttaaaactct aaatac                                         26

<210> SEQ ID NO 21
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 21
gggaatatag gtaagtggga agtat                                          25

<210> SEQ ID NO 22
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 22
gattgtaatg attttatgtg tagtatt                                        27

<210> SEQ ID NO 23
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 23
aaataatata tctctataat aatc                                           24

<210> SEQ ID NO 24
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 24
ttcattacct acacctatcc aatacc                                         26

<210> SEQ ID NO 25
<211> LENGTH: 30
<212> TYPE: DNA
<213> ORGANISM: Artificial Sequence
<220> FEATURE:
```

<223> OTHER INFORMATION: Oligonucleotide primer

<400> SEQUENCE: 25
gatttatagt gtaatgagta attggatagt                                    30

<210> SEQ ID NO 26
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 26
ggttatagta agttagataa gt                                            22

<210> SEQ ID NO 27
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 27
tccccatcta taccttcaaa taac                                          24

<210> SEQ ID NO 28
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 28
cctatttttt tttctacaat tac                                           23

<210> SEQ ID NO 29
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 29
gtaattgatt tttattgtta tgagt                                         25

<210> SEQ ID NO 30
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 30
gttatagata gtttagttgg ataagt                                        26

<210> SEQ ID NO 31
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 31
ctaaatcaac cattataatt acaatc                                        26

<210> SEQ ID NO 32

```
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 32
cctatctatc tatcaattac tac                                         23

<210> SEQ ID NO 33
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 33
ttttgtatat ggaaatatat tagaat                                      26

<210> SEQ ID NO 34
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 34
taggtgtatt atatgttaaa gatt                                        24

<210> SEQ ID NO 35
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 35
cctcatctaa actatcactt aattac                                      26

<210> SEQ ID NO 36
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 36
taactaatta tacttatcca tctaac                                      26

<210> SEQ ID NO 37
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 37
aaataatgta ataaatagtt atgtt                                       25

<210> SEQ ID NO 38
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 38
```
gttgtgttta gttgaaaagt aaagat                                          26

<210> SEQ ID NO 39
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 39
ccatatatat actctataca cacaaac                                         27

<210> SEQ ID NO 40
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 40
aaacacacta ttccaaatat ac                                              22

<210> SEQ ID NO 41
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 41
ttaaagttta ttttgtagga aattg                                           25

<210> SEQ ID NO 42
<211> LENGTH: 28
<212> TYPE: DNA
<213> ORGANISM: Artificial Sequence
<220> FEATURE:
<223> OTHER INFORMATION: Oligonucleotide primer

<400> SEQUENCE: 42
gatttatgtt tttataatga aatatagt                                        28

<210> SEQ ID NO 43
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 43
ctaataaatc cataaacaac tac                                             23

<210> SEQ ID NO 44
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 44
cataacaaat tactaattta catttac                                         27

<210> SEQ ID NO 45
<211> LENGTH: 27
<212> TYPE: DNA
<213> ORGANISM: Artificial Sequence
<220> FEATURE:

```
<223> OTHER INFORMATION: Oligonucleotide primer

<400> SEQUENCE: 45
tattttgaat taattgattt attttgt                                        27

<210> SEQ ID NO 46
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 46
atgagtaatt atgtgatagt tt                                             22

<210> SEQ ID NO 47
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 47
atacatatac ccataaacaa ctac                                           24

<210> SEQ ID NO 48
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 48
ttattactat acacaactaa aac                                            23

<210> SEQ ID NO 49
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 49
gatattttga ttatgttgga tatgt                                          25

<210> SEQ ID NO 50
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 50
gttgaagaag aaattaaata agat                                           24

<210> SEQ ID NO 51
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 51
tactatcaca tccacaacaa caaatc                                         26

<210> SEQ ID NO 52
```

```
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 52
ctctaatatc tatttctata cactac                                              26

<210> SEQ ID NO 53
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 53
gttatgagta attagaagat agt                                                 23

<210> SEQ ID NO 54
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 54
attattaaat attgatttgt tgt                                                 23

<210> SEQ ID NO 55
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 55
atacctataa tatactctac tataac                                              26

<210> SEQ ID NO 56
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 56
caaaatttta taaatatac ctatc                                                25

<210> SEQ ID NO 57
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 57
gtatatagtg gagaaagaaa ttggat                                              26

<210> SEQ ID NO 58
<211> LENGTH: 28
<212> TYPE: DNA
<213> ORGANISM: Artificial Sequence
<220> FEATURE:
<223> OTHER INFORMATION: Oligonucleotide primer

<400> SEQUENCE: 58
```
gaataataaa ttagatgtgt tttgtgtt                                             28

<210> SEQ ID NO 59
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 59
ccaattattc ataacaatac aaatc                                                25

<210> SEQ ID NO 60
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 60
acttaatcat cttcatctaa ac                                                   22

<210> SEQ ID NO 61
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 61
tagtgtaygg ggttagtttg gaagt                                                25

<210> SEQ ID NO 62
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 62
atttgattta ttaataaggt gt                                                   22

<210> SEQ ID NO 63
<211> LENGTH: 28
<212> TYPE: DNA
<213> ORGANISM: Artificial Sequence
<220> FEATURE:
<223> OTHER INFORMATION: Oligonucleotide primer

<400> SEQUENCE: 63
ctataatata ttataaaaat attaatac                                             28

<210> SEQ ID NO 64
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 64
caattactca taacattaca aatc                                                 24

<210> SEQ ID NO 65
<211> LENGTH: 29
<212> TYPE: DNA
<213> ORGANISM: Artificial Sequence
<220> FEATURE:

```
<223> OTHER INFORMATION: Oligonucleotide primer

<400> SEQUENCE: 65
gatggkgata tgrtdsatrt wggdtwtgg                                        29

<210> SEQ ID NO 66
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 66
taartatttw gattatwtdd raatg                                            25

<210> SEQ ID NO 67
<211> LENGTH: 28
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: 4, 5
<223> OTHER INFORMATION: n = A,T,C or G

<400> SEQUENCE: 67
tatnntawcc ytahrchywh tahaacca                                         28

<210> SEQ ID NO 68
<211> LENGTH: 29
<212> TYPE: DNA
<213> ORGANISM: Artificial Sequence
<220> FEATURE:
<223> OTHER INFORMATION: Oligonucleotide primer

<400> SEQUENCE: 68
amaaahamht aatthyhmma acawayacc                                        29

<210> SEQ ID NO 69
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 69
gatttdkwdt gtwatgagta att                                              23

<210> SEQ ID NO 70
<211> LENGTH: 23
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: 12, 13
<223> OTHER INFORMATION: n = A,T,C or G

<400> SEQUENCE: 70
grkttdkwdt gnnrkgarta att                                              23

<210> SEQ ID NO 71
<211> LENGTH: 17
<212> TYPE: DNA
<213> ORGANISM: Artificial Sequence
<220> FEATURE:
```

```
<223> OTHER INFORMATION: Oligonucleotide primer

<400> SEQUENCE: 71
rryrrkttag abgadga                                                    17

<210> SEQ ID NO 72
<211> LENGTH: 17
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: 12
<223> OTHER INFORMATION: n = A,T,C or G

<400> SEQUENCE: 72
rrhrrkttwg ankwdga                                                    17

<210> SEQ ID NO 73
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 73
ydatacctwc wmawwhvdcc at                                              22

<210> SEQ ID NO 74
<211> LENGTH: 22
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: 8, 9, 17
<223> OTHER INFORMATION: n = A,T,C or G

<400> SEQUENCE: 74
ydataccnnh whhdwhndcc at                                              22

<210> SEQ ID NO 75
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 75
achhhaaacc ahcchhwaca hcc                                             23

<210> SEQ ID NO 76
<211> LENGTH: 14
<212> TYPE: DNA
<213> ORGANISM: Artificial Sequence
<220> FEATURE:
<223> OTHER INFORMATION: Oligonucleotide primer

<400> SEQUENCE: 76
atatatatat atat                                                       14

<210> SEQ ID NO 77
<211> LENGTH: 14
<212> TYPE: DNA
<213> ORGANISM: Artificial Sequence
<220> FEATURE:
```

<223> OTHER INFORMATION: Oligonucleotide primer

<400> SEQUENCE: 77
aaaaaaattt tttt                                                         14

<210> SEQ ID NO 78
<211> LENGTH: 10
<212> TYPE: DNA
<213> ORGANISM: Artificial Sequence
<220> FEATURE:
<223> OTHER INFORMATION: Oligonucleotide primer

<400> SEQUENCE: 78
ggggaaattc                                                              10

<210> SEQ ID NO 79
<211> LENGTH: 10
<212> TYPE: DNA
<213> ORGANISM: Artificial Sequence
<220> FEATURE:
<223> OTHER INFORMATION: Oligonucleotide primer

<400> SEQUENCE: 79
gaatttcccc                                                              10

<210> SEQ ID NO 80
<211> LENGTH: 10
<212> TYPE: DNA
<213> ORGANISM: Artificial Sequence
<220> FEATURE:
<223> OTHER INFORMATION: Oligonucleotide primer

<400> SEQUENCE: 80
ggggaaattu                                                              10

<210> SEQ ID NO 81
<211> LENGTH: 10
<212> TYPE: DNA
<213> ORGANISM: Artificial Sequence
<220> FEATURE:
<223> OTHER INFORMATION: Oligonucleotide primer

<400> SEQUENCE: 81
gaatttuuuu                                                              10

<210> SEQ ID NO 82
<211> LENGTH: 10
<212> TYPE: DNA
<213> ORGANISM: Artificial Sequence
<220> FEATURE:
<223> OTHER INFORMATION: Oligonucleotide primer

<400> SEQUENCE: 82
ggggaaattt                                                              10

<210> SEQ ID NO 83
<211> LENGTH: 10
<212> TYPE: DNA
<213> ORGANISM: Artificial Sequence
<220> FEATURE:
<223> OTHER INFORMATION: Oligonucleotide primer

<400> SEQUENCE: 83
gaattttttt                                                              10

<210> SEQ ID NO 84

```
<211> LENGTH: 10
<212> TYPE: DNA
<213> ORGANISM: Artificial Sequence
<220> FEATURE:
<223> OTHER INFORMATION: Oligonucleotide primer

<400> SEQUENCE: 84
aaatttcccc                                                          10

<210> SEQ ID NO 85
<211> LENGTH: 10
<212> TYPE: DNA
<213> ORGANISM: Artificial Sequence
<220> FEATURE:
<223> OTHER INFORMATION: Oligonucleotide primer

<400> SEQUENCE: 85
aaaaaaattc                                                          10

<210> SEQ ID NO 86
<211> LENGTH: 10
<212> TYPE: DNA
<213> ORGANISM: Artificial Sequence
<220> FEATURE:
<223> OTHER INFORMATION: Oligonucleotide primer

<400> SEQUENCE: 86
gaattttttt                                                          10
```

ASSAY FOR SCREENING FOR POTENTIAL CERVICAL CANCER

RELATED APPLICATIONS

This application is the U.S. National Phase filing under 35 U.S.C. §371 of PCT/AU2006/001349, filed Sep. 14, 2006, which designated the United States and was published in English, which claims priority under 35 U.S.C. §119(e) to U.S. Provisional Application No. 60/717,148, filed Sep. 14, 2005. The contents of these applications are incorporated herein by reference in their entireties.

TECHNICAL FIELD

The invention relates generally to the detection of the presence of a virus together with the detection of a genomic marker(s) in a sample as an assay for determining the health state of a subject. The invention is suitable as a risk assessment test that has prognostic value.

BACKGROUND ART

A number of procedures are presently available for the detection of specific nucleic acid molecules. These procedures typically depend on sequence-dependent hybridisation between the target nucleic acid and nucleic acid probes which may range in length from short oligonucleotides (20 bases or less) to sequences of many kilobases (kb).

The most widely used method for amplification of specific sequences from within a population of nucleic acid sequences is that of polymerase chain reaction (PCR) (Dieffenbach, C and Dveksler, G. eds. PCR Primer: A Laboratory Manual. Cold Spring Harbor Press, Plainview N.Y.). In this amplification method, oligonucleotides, generally 20 to 30 nucleotides in length on complementary DNA strands and at either end of the region to be amplified, are used to prime DNA synthesis on denatured single-stranded DNA. Successive cycles of denaturation, primer hybridisation and DNA strand synthesis using thermostable DNA polymerases allows exponential amplification of the sequences between the primers. RNA sequences can be amplified by first copying using reverse transcriptase to produce a complementary DNA (cDNA) copy. Amplified DNA fragments can be detected by a variety of means including gel electrophoresis, hybridisation with labelled probes, use of tagged primers that allow subsequent identification (eg by an enzyme linked assay), and use of fluorescently-tagged primers that give rise to a signal upon hybridisation with the target DNA (eg Beacon and TaqMan systems).

As well as PCR, a variety of other techniques have been developed for detection and amplification of specific nucleotide sequences. One example is the ligase chain reaction (Barany, F. et al., Proc. Natl. Acad. Sci. USA 88, 189-193, 1991).

Another example is isothermal amplification which was first described in 1992 (Walker G T, Little M C, Nadeau J G and Shank D. Isothermal in vitro amplification of DNA by a restriction enzyme/DNA polymerase system. PNAS 89: 392-396 (1992) and termed Strand Displacement Amplification (SDA). Since then, a number of other isothermal amplification technologies have been described including Transcription Mediated Amplification (TMA) and Nucleic Acid Sequence Based Amplification (NASBA) that use an RNA polymerase to copy RNA sequences but not corresponding genomic DNA (Guatelli J C, Whitfield K M, Kwoh D Y, Barringer K J, Richmann D D and Gingeras T R. Isothermal, in vitro amplification of nucleic acids by a multienzyme reaction modeled after retroviral replication. PNAS 87: 1874-1878 (1990): Kievits T, van Gemen B, van Strijp D, Schukkink R, Dircks M, Adriaanse H, Malek L, Sooknanan R, Lens P. NASBA isothermal enzymatic in vitro nucleic acid amplification optimized for the diagnosis of HIV-1 infection. J Viral Methods. 1991 December; 35(3):273-86).

Other DNA-based isothermal techniques include Rolling Circle Amplification (RCA) in which a DNA polymerase extends a primer directed to a circular template (Fire A and Xu S Q. Rolling replication of short circles. PNAS 92: 4641-4645 (1995), Ramification Amplification (RAM) that uses a circular probe for target detection (Zhang W, Cohenford M, Lentrichia B, Isenberg H D, Simson E, Li H, Yi J, Zhang D Y. Detection of *Chlamydia trachomatis* by isothermal ramification amplification method: a feasibility study. J Clin Microbiol. 2002 January; 40(1):128-32.) and more recently, Helicase-Dependent isothermal DNA amplification (HDA), that uses a helicase enzyme to unwind the DNA strands instead of heat (Vincent M, Xu Y, Kong H. Helicase-dependent isothermal DNA amplification. EMBO Rep. 2004 August; 5(8):795-800.)

Recently, isothermal methods of DNA amplification have been described (Walker G T, Little M C, Nadeau J G and Shank D. Isothermal in vitro amplification of DNA by a restriction enzyme/DNA polymerase system. PNAS 89: 392-396 (1992). Traditional amplification techniques rely on continuing cycles of denaturation and renaturation of the target molecules at each cycle of the amplification reaction. Heat treatment of DNA results in a certain degree of shearing of DNA molecules, thus when DNA is limiting such as in the isolation of DNA from a small number of cells from a developing blastocyst, or particularly in cases when the DNA is already in a fragmented form, such as in tissue sections, paraffin blocks and ancient DNA samples, this heating-cooling cycle could further damage the DNA and result in loss of amplification signals. Isothermal methods do not rely on the continuing denaturation of the template DNA to produce single stranded molecules to serve as templates from further amplification, but on enzymatic nicking of DNA molecules by specific restriction endonucleases at a constant temperature, or unwinding the DNA duplex by the use of helicase enzymes.

The technique termed Strand Displacement Amplification (SDA) relies on the ability of certain restriction enzymes to nick the unmodified strand of hemi-modified DNA and the ability of a 5'-3' exonuclease-deficient polymerase to extend and displace the downstream strand. Exponential amplification is then achieved by coupling sense and antisense reactions in which strand displacement from the sense reaction serves as a template for the antisense reaction (Walker G T, Little M C, Nadeau J G and Shank D. Isothermal in vitro amplification of DNA by a restriction enzyme/DNA polymerase system. PNAS 89: 392-396 (1992). Such techniques have been used for the successful amplification of *Mycobacterium tuberculosis* (Walker G T, Little M C, Nadeau J G and Shank D. Isothermal in vitro amplification of DNA by a restriction enzyme/DNA polymerase system. PNAS 89: 392-396 (1992), HIV-1, Hepatitis C and HPV-16 Nuovo G. J., 2000), *Chlamydia trachomatis* (Spears P A, Linn P, Woodard D L and Walker G T. Simultaneous Strand Displacement Amplification and Fluorescence Polarization Detection of *Chlamydia trachomatis*. Anal. Biochem. 247: 130-137 (1997).

The use of SDA to date has depended on modified phosphorthioate nucleotides in order to produce a hemi-phosphorthioate DNA duplex that on the modified strand would be resistant to enzyme cleavage, resulting in enzymic nicking instead of digestion to drive the displacement reaction. Recently, however, several "nickase" enzyme have been engineered. These enzymes do not cut DNA in the traditional manner but produce a nick on one of the DNA strands. "Nickase" enzymes include N.Alw1 (Xu Y, Lunnen K D and Kong H. Engineering a nicking endonuclease N.Alw1 by domain swapping. PNAS 98: 12990-12995 (2001), N.BstNB1 (Morgan R D, Calvet C, Demeter M, Agra R, Kong H. Characterization of the specific DNA nicking activity of restriction endonuclease N.BstNBI. Biol Chem. 2000 November; 381 (11):1123-5.) and Mly1 (Besnier C E, Kong H. Converting Mly1 endonuclease into a nicking enzyme by changing its oligomerization state. EMBO Rep. 2001 September; 2(9): 782-6. Epub 2001 Aug. 23). The use of such enzymes would thus simplify the SDA procedure.

In addition, SDA has been improved by the use of a combination of a heat stable restriction enzyme (Ava1) and Heat stable Exo-polymerase (Bst polymerase). This combination has been shown to increase amplification efficiency of the reaction from a $10^8$ fold amplification to $10^{10}$ fold amplification so that it is possible, using this technique, to the amplification of unique single copy molecules. The resultant amplification factor using the heat stable polymerase/enzyme combination is in the order of $10^9$ (Milla M. A., Spears P. A., Pearson R. E. and Walker G. T. Use of the Restriction Enzyme Ava1 and Exo-Bst Polymerase in Strand Displacement Amplification Biotechniques 1997 24:392-396).

To date, all isothermal DNA amplification techniques require the initial double stranded template DNA molecule to be denatured prior to the initiation of amplification. In addition, amplification is only initiated once from each priming event.

For direct detection, the target nucleic acid is most commonly separated on the basis of size by gel electrophoresis and transferred to a solid support prior to hybridisation with a probe complementary to the target sequence (Southern and Northern blotting). The probe may be a natural nucleic acid or analogue such as peptide nucleic acid (PNA) or locked nucleic acid (LNA) or intercalating nucleic acid (INA). The probe may be directly labelled (eg with $^{32}$P) or an indirect detection procedure may be used. Indirect procedures usually rely on incorporation into the probe of a "tag" such as biotin or digoxigenin and the probe is then detected by means such as enzyme-linked substrate conversion or chemiluminescence.

Another method for direct detection of nucleic acid that has been used widely is "sandwich" hybridisation. In this method, a capture probe is coupled to a solid support and the target nucleic acid, in solution, is hybridised with the bound probe. Unbound target nucleic acid is washed away and the bound nucleic acid is detected using a second probe that hybridises to the target sequences. Detection may use direct or indirect methods as outlined above. Examples of such methods include the "branched DNA" signal detection system, an example that uses the sandwich hybridization principle (1991, Urdea, M. S., et al., Nucleic Acids Symp. Ser. 24, 197-200). A rapidly growing area that uses nucleic acid hybridisation for direct detection of nucleic acid sequences is that of DNA microarrays, (2002, Nature Genetics, 32, [Supplement]; 2004, Cope, L. M., et al., Bioinformatics, 20, 323-331; 2004, Kendall, S. L., et al., Trends in Microbiology, 12, 537-544). In this process, individual nucleic acid species, that may range from short oligonucleotides, (typically 25-mers in the Affymetrix system), to longer oligonucleotides, (typically 60-mers in the Applied Biosystems and Agilent platforms), to even longer sequences such as cDNA clones, are fixed to a solid support in a grid pattern or photolithographically synthesized on a solid support. A tagged or labelled nucleic acid population is then hybridised with the array and the level of hybridisation to each spot in the array quantified. Most commonly, radioactively- or fluorescently-labelled nucleic acids (eg cRNAs or cDNAs) are used for hybridisation, though other detection systems can be employed, such as chemiluminescence.

Currently, there is much interest in harnessing molecular methods for the diagnosis of infectious disease, since such newer methods hold the promise of sensitive and specific detection of pathogenic organisms. In this context, the present invention deals with human papilloma virus (HPV), whose DNA genome exists at the populational level as a variable gene pool with individual HPV types differing both at the nucleotide sequence level as well as in the sizes of their genomes. Detecting and accurately identifying different HPV types in various clinical samples via molecular tests is hampered by the limitations of the various molecular tests. In addition, a large number of 'genotypes', 'variants', 'subtypes' and 'types' exist within the umbrella grouping that defines HPV. For example, there are now over 100 recognized types of HPV some of which are strongly correlated with human disease. The so called high- and medium-risk types are implicated in the progression to cancer and their detection via the most accurately available molecular methods is an urgent clinical priority.

The major problem is that detection of HPV alone is not necessarily a very good indicator of progression to cancer. Although Cervical Intraepithelial Neoplasia (CIN) can progress to an invasive form, many lesions either regress or persist but without progressing to carcinoma. Seventy percent of women will clear an HPV infection within two years (1998, Journal of Pediatrics, 132, 277-284; Moscicki, A. B., et al.). However, the finding of CIN and its progression is so variable that even untreated, it may return to normalcy or lead to a full blown carcinoma. Approximately one third to one half of CINI and CINII cases spontaneously regress (1990, Australian and New Zealand Journal of Obstetrics and Gynaecology, 30, 1-23., Channen, W et al.), The time taken to progress from CINI to CINII is of the order of a decade, but in some females can be two decades or more. (2000, Cancer Research, 60, 6027-6032., Ylitalo, E et al.).

Viral infection of a cell, tissue or organ can cause the genome methylation signature of these entities to be altered, as in the case of Epstein-Barr virus and it's association with gastric carcinoma (2002, American J. Pathology, 160, 787-794, Kang, G. H., et al). Since methylation or demethylation is a stable change inherited over many cell divisions, and in some cases, generations of organisms, an alteration of the usually stable methylome can be predictive of the pre-cancerous or cancerous state.

It has been challenging to implement reliable and robust DNA-based detection systems that recognise all the different HPV types in a single assay, since not only are there cross hybridization problems between different HPV genomic types, but the exact classification of what constitutes an HPV type is dependent upon genomic sequence similarities which have significant bioinformatic limitations. Thus, while new HPV types have been defined as ones where there is less than 90% sequence similarity with previous HPV types, finer taxonomic subdivisions are more problematic to deal with. Thus, a new HPV 'subtype' is defined when the DNA sequence similarity is in the 90-98% range relative to previous subtypes. A new 'variant' is defined when the sequence similarity is between 98-100% of previous variants (1993, Van Rast, M. A., et al., Papillomavirus Rep, 4, 61-65; 1998, Southern, S. A.

and Herrington, C. S. Sex. Transm. Inf. 74, 101-109). This spectrum can broaden further to the point where variation could be measured based on comparing single genomes from single isolated viral particles. In such a case, a 'genotype' would be any fully sequenced HPV genome that minimally differs by one base from any other fully sequenced HPV genome. This includes all cases where a single base at a defined position can exist in one of four states, G, A, T or C, as well as cases where the base at that given position has been altered by deletion, addition, amplification or transposition to another site.

For the above reasons, all the bioinformatic comparisons used in the present patent specification application are made relative to the HPV16 genome (using positions 1 to 7904 of HPV16 as the standard comparator), and using prior art BLAST methodologies, (1996, Morgenstern, B., et al., Proc. Natl. Acad. Sci. USA. 93, 12098-12103). The standard HPV 'type' utilized herein for reference purposes is HPV16 of the Papillomaviridae, a papillomavirus of 7904 base pairs (National Center for Biotechnology Information, NCBI locus NC_001526; version NC_001526.1; GI:9627100; references, Medline, 91162763 and 85246220; PubMed 1848319 and 2990099).

The difficulties faced by existing HPV detection systems in the context of disease risk assessment are largely threefold. First limitations of the technology systems themselves. Secondly, limitations of the pathological interpretations of diseased cell populations. Thirdly, limitations at the clinical level of assessing disease progression in different human populations that are subject to differences in genetic background as well as contributing cofactors.

HPV of certain types are implicated in cancers of the cervix and contribute to a more poorly defined fraction of cancers of the vagina, vulvae, penis and anus. The ring of tissue that is the cervical transformation zone is an area of high susceptibility to HPV carcinogenicity, and assessment of its state from complete cellular normalcy to invasive carcinoma has been routinely evaluated using visual or microscopic criteria via histological, cytological and molecular biological methodologies. The early detection of virally-induced abnormalities at both the viral level and that of the compromised human cell, would be of enormous clinical relevance if it could help in determining where along a molecular trajectory, from normal to abnormal tissue, a population of cells has reached. However, despite the use of the Pap smear for half a century, a solid early risk assessment between abnormal cervical cytological diagnoses and normalcy is currently still problematical. Major problems revolve around the elusive criteria on which to define 'precancer', such as the various grades of Cervical Intraepithelial Neoplasia, (CIN1, CIN2 and CIN3) and hence on the clinical decisions that relate to treatment options. Precancer definitions are considered by some clinicians to be a pseudo-precise way in which to avoid using CIN2, CIN3 and carcinoma in situ. There is great heterogeneity in microscopic diagnoses and even in the clinical meaning of CIN2, (2003, Schiffman, M., J. Nat. Cancer Instit. Monog. 31, 14-19). Some CIN2 lesions have a bad microscopic appearance but will nevertheless be overcome by the immune system and disappear, whereas other lesions will progress to invasive carcinoma. Thus CIN2 is considered by some as a buffer zone of equivocal diagnosis although the boundary conditions of such a zone remain controversial. Some clinicians consider it to be poor practice to combine CIN2 and CIN3, whereas others will treat all lesions of CIN2 or worse. Finally, the literature indicates that between a third and two thirds of CIN3 assigned women will develop invasive carcinoma, but even this occurs in an unpredictable time-dependent fashion, (2003, Schiffman, M., J. Nat. Cancer. Instit. Monog. 31, 14-19; 1978, Kinlen, L. J., et al., Lancet 2, 463-465; 1956, Peterson, O. Am. J. Obstet. Gynec. 72, 1063-1071).

The central problem still confronting physicians today is that defining low grade cytological abnormalities such as atypical squamous cells of undetermined significance, (ASCUS), or squamous intraepithelial lesions (SILs) is difficult. 'In fact, ASCUS is not a proper diagnosis but rather is a "wastebasket" category of poorly understood changes', (1996, Lorincz, A. T., 1996, J. Obstet. Gyncol. Res. 22, 629-636). The whole spectrum of precancerous lesions is difficult to interpret owing to cofactor effects from oral contraceptive use, smoking, pathogens other than HPV such as Chlamydia trachomatis and Herpes Simplex Virus type 2, antioxidant nutrients and cervical inflammation, all of which are claimed to modulate the risk of progression from high grade squamous intraepithelial lesions (HSILs) to cervical cancer (2003, Castellsague, X. J. Nat. Cancer Inst. Monog. 31, 20-28). The introduction of the Bethesda system of classification and its revision in 2001 has done little to reduce the confusion among clinicians, since it was initially found unhelpful to include koilocytotic atypia with CIN1 into the newer category of low-grade squamous intraepithelial lesions, (LSILs). The result of the introduction of the Bethesda system was that many clinicians would not carry out colposcopy on koilocytotic atypia, but felt compelled do so on patients with CIN1', (1995, Hatch, K. D., Am. J. Obstet. Gyn. 172, 1150-1157). It was clear that although colposcopic expertise required many years of training, subjective cytological criteria still lead to inconsistencies and non-reproducibilities, (1994, Sherman, M. E., Am. J. Clin. Pathology, 102, 182-187; 1988, Giles, J. A., Br. Med. J., 296, 1099-1102).

The continuing diagnostic hurdle is that vague diagnoses such as 'atypia' can account for 20% or more of diagnoses in some settings, (1993, Schiffman, M. Contemporary OB/GYN, 27-40). This is illustrated by a test designed specifically to evaluate the level of independent diagnostic agreement of pathologists on smears that were 'atypical'. It was found that exact agreement between five professional pathologists on an identical set of samples occurred in only 29% of cases, (1994, Sherman, M. E., et al., Am. J. Clin. Pathology, 102, 182-187). The net result is that cervical cytology continues to have high false negative rates (termed low sensitivity) and high false positive rates, (termed low specificity). The cytological interpretations of various pathologists yield a false negative rate of up to 20% or so and a false positive rate of up to 15% (1993, Koss, L. G., Cancer, 71, 1406-1412). False positive results lead to unnecessary colposcopic examinations, biopsies and treatments, all of which add to the health care cost burden. False negative results lead to potential malpractice law suits with their associated costs. It was into this arena that molecular diagnoses of early stages of cervical abnormalities using tests for HPV offer a less subjective test than cytological ones.

Genomic indicators of a lack of well being in an organism are intimately tied to changes in genomic methylation status at a number of levels. Dietary supplementation can have unintended and deleterious consequences on methylation and metabolic well being, (Waterland, R. A., 2003, Molecular and Cellular Biology, 23, 5293-5300) and aberrant methylation of certain genomic promoter regions, such as that of the reelin locus, are implicated in various psychiatric conditions such as schizophrenia (2002, Chen, Y., et al., Nucleic Acids Research, 30, 2930-2939; Miklos, G. L. G., and Maleszka, R., 2004, Nature Biotechnology, 22, 615-621). The single largest area of methylation investigation is in cancer research, where both hypermethylation and hypomethylation of genomic regions, is extensively documented (French, S. W., et al., 2002, Clinical Immunology, 103, 217-230; Frigola, J., et al., 2005, Human Molecular Genetics, 14, 319-326; Belinsky S. A., et al., Nature Reviews Cancer, 4, 1-11). Some of these studies aim at uncovering prognostic biomarkers (Baker, M., 2005, Nature Biotechnology, 23, 297-304) for indications of cancer, but the biomarker field is riddled with inconsistent results. In addition, rarely are such genomic studies interfaced with other sources of perturbations to cells and tissues that arise from infections with microorganisms and viruses. In addition, cancer genomes generally contain massive genomic upheavals, such as chromosomal aneuploidy, segmental aneuploidy, deletions, amplifications, inversions, translocations and multiple mutations (Duesberg, P., 2004, Cell Cycle, 3, 823-828; Miklos, G. L. G., 2005, Nature Biotechnology, 23, 535-537) and the importance of these for early detection, in the context of methylation changes, has not yet been very deeply explored, (Vogelstein, B., et al., 2004, Nature Medicine, 10, 789-799; Lucito, R., at al., 2003, Genome Research, 13, 2291-2305).

Given all the problems and shortcomings outlined above, there is still controversy as regards the clinical impact of DNA methodologies particularly in screening for pre-neoplastic lesions. Sensitive early molecular prognostic indicators of cellular abnormalities would be extremely valuable. The present inventors have developed new methods, kits and integrated bioinformatic platforms for detecting viruses and genomic targets for use in determining the health state of an individual.

DISCLOSURE OF INVENTION

In a general aspect, the present invention relates to an assay for determining a health state of a subject using a combination of detecting the presence of a virus and detecting the presence, absence or status of a genomic target or marker indicative of a health state. The invention can be carried out if required on only one sample in the same test, vessel, or reaction.

In a first aspect, the present invention provides an assay for determining a health state of a subject comprising:
(a) treating a sample from a subject with an agent that is capable of modifying unmethylated cytosines in nucleic acid, wherein viral nucleic acid and genomic nucleic acid in the sample are treated to form derivative viral nucleic acid and derivative genomic nucleic acid;
(b) assaying for the presence of derivative viral nucleic acid in the treated sample; and
(c) determining status of a genomic target in the derivative genomic nucleic acid in the treated sample, wherein the presence of one or more of derivative viral nucleic acid and the status of the genomic target is indicative of a health state.

In one preferred form, the assay further comprises:
amplifying at least part of the derivative viral nucleic acid and derivative genomic nucleic acid prior to the assaying and determining steps.

In a second aspect, the present invention provides an assay for determining a health state of a subject comprising:
(a) treating a sample from the subject containing viral nucleic acid and genomic nucleic acid with an agent that modifies unmethylated cytosine to form derivative viral nucleic acid and derivative genomic nucleic acid having a reduced number of cytosines but having substantially the same total number of bases as the corresponding untreated viral nucleic acid and untreated genomic nucleic acid;
(b) obtaining a virus-specific nucleic acid molecule;
(c) obtaining a nucleic acid molecule having a genomic target;
(d) testing for the presence of a virus-specific nucleic acid molecule; and
(e) determining status of the genomic target in the treated and amplified sample, wherein detection of one or more of the virus-specific nucleic acid molecules and the status of the target is indicative of a health state of the subject.

Preferably, the virus-specific nucleic acid molecule and the nucleic acid molecule having a genomic target are obtained by amplifying the derivative viral nucleic acid and the derivative genomic nucleic acid.

In a third aspect, the present invention provides an assay for determining a health state of a subject comprising:
(a) treating a sample from a subject with an agent that modifies unmethylated cytosine to form derivative nucleic acid;
(b) providing primers capable of allowing amplification of a desired viral nucleic acid molecule to the derivative nucleic acid;
(c) providing primers capable of allowing amplification of a target genomic nucleic acid molecule to the derivative nucleic acid;
(d) carrying out an amplification reaction on the derivative nucleic acid; and
(e) assaying for the presence of amplified desired viral nucleic acid and amplified target genomic nucleic acid, wherein presence or absence of one or more amplified products is indicative of a health state of the subject.

In one preferred form, step (e) comprises assaying for the presence of an amplified nucleic acid product containing the desired virus-specific nucleic acid molecule, wherein detection of the desired virus-specific nucleic acid molecule is indicative of the presence of the virus in the sample.

In another preferred form, step (e) further comprises assaying for the presence of an amplified nucleic acid product containing the target nucleic acid molecule, wherein detection of the target nucleic acid molecule is indicative of a genomic or gene state in the sample.

In a fourth aspect, the present invention provides an assay for determining a health state of a subject comprising:
(a) treating a sample from a subject with a bisulphite reagent under conditions that cause unmethylated cytosines in viral and genomic nucleic acid to be converted to uracil forming derivative viral nucleic acid and derivative genomic nucleic acid;
(b) providing primers capable of binding to regions of derivative viral nucleic acid to the sample, the primers being capable of allowing amplification of a desired viral-specific nucleic acid molecule in the derivative viral nucleic acid;
(c) providing primers capable of binding to regions of derivative genomic nucleic acid to the sample, the primers being capable of allowing amplification of a desired target genomic-specific nucleic acid molecule in the derivative genomic nucleic acid;
(d) carrying out an amplification reaction on the treated sample; and
(e) assaying for the presence of an amplified viral nucleic acid product and an amplified genomic nucleic acid target, wherein detection of one or both of the product and target is indicative of a health state of the subject.

In a preferred form, the assay further includes:
(f) testing a sample having a virus present to determine the type, subtype, variant or genotype of the virus in the sample.

Amplification can be carried out by any suitable means such as PCR or isothermal amplification.

If the virus has a DNA genome, then treatment with the agent will produce a derivative nucleic acid. If, however, the virus has an RNA genome, then the genome can be converted to DNA via a reverse transcriptase methodology. Conversion can be carried out either before or after treatment with the agent. Preferably, to ensure that there is no conversion of any other RNA to cDNA, virus specific primers are used.

The subject may be any higher life form that has genomic methylation at a significant frequency. Typically, the present invention is suitable for animals or humans, and for virally infected plant species. Preferably, the animals are farmed or domesticated mammals, but they may be wild populations whose health state needs to be monitored. The human can be a healthy individual or a sick person.

The desired viral nucleic acid molecule can be specific for a virus family per se, or a lower taxonomic category, such as genus or species, a type or sub-type, or variant or genotype of virus, whether indicative of disease or not.

Methylation of some genomic regions typically causes expression of associated genes to be turned 'off'. In certain situations, however, some genes may have associated methylated regions, but gene expression is still "on". Thus, in a preferred form, methylation or unmethylation can be used as a prognostic indicator, rather than for gene expression per se. It is also possible to block amplification of specific nucleic acid regions so as to determine or target desired methylation states.

The target genomic nucleic acid can be specific for a gene or genes or regulatory region such as a promoter or enhancer, or any coding or non coding, or static or mobile, region of a genome. Preferably, the target has a methylation characteristic that is useful for diagnostic or prognostic purposes. This includes mobile or once mobile elements, such as those exemplified by the LINE family of repetitive DNA sequences (Long INterspersed Elements; also known as Long Interspersed Nuclear Elements, an abundant retrotransposon family within the human genome; 1996, Smit, A. F. A., Current Opinion in Genetics and Development, 6, 743-748; 2003, Han, J. S., et al., Nature, 429, 268-274; 2004, Brouha, B., et al., Proc. Natl. Acad. Sci. USA. 100, 5280-5285, and the SINE family (Short INterspersed Elements also known as Short Interspersed Nuclear Elements; Batzer, M. A., et al.), which together make up nearly half of the human genome. More preferably, the target genomic nucleic acid is indicative of a methylated or unmethylated region of genomic nucleic acid.

Preferably, the assay is repeated with primers specific for a given type or group of types of virus, wherein the presence of an amplified product is indicative of the type or group of types of virus.

Typically, after amplification, each derivative nucleic acid forms a simplified nucleic acid molecule having a reduced total number of cytosines compared with the corresponding untreated nucleic acid, wherein the simplified nucleic acid molecule preferably includes a nucleic acid sequence specific for the virus or the target.

For double stranded DNA which contains no methylated cytosines, the treating step results in two derivative nucleic acids, each containing the bases adenine, guanine, thymine and uracil. The two derivative nucleic acids are produced from the two single strands of the double stranded DNA. The two derivative nucleic acids have no cytosines but still have the same total number of bases and sequence length as the original untreated DNA molecule. Importantly, the two derivatives are not complimentary to each other and form a top and a bottom strand. One or more of the strands can be used as the target for amplification to produce the simplified nucleic acid molecule.

Typically, the simplified nucleic acid sequence specific for the virus does not occur naturally in an untreated viral genome.

The virus strain or type can confer a high, medium or low level oncogenic or other disease status on a given tissue in a particular human or animal ethnic lineage. Examples include high risk HPV types 16, 18, 45 and 56; medium risk HPV types 30, 31, 33, 35, 39, 51, 52, 58, 59, and 68; and low risk HPV types 6, 11, 42, 43, 44, 53, 54, and 55.

The viruses can be from any of the described families of human viruses, such as from the:

Poxviridae which includes, cowpox, monkeypox, VAccinia and Variola virus. Depending on the virus, these can give rise to skin and mucous membrane lesions, eczema, and contagious pustular dermatitis. The various human diseases are summarized in the 2003, International Statistical Classification of Diseases and Related Health Problems, (ICD), $10^{th}$ revision.

Paramyxoviridae which includes Nipah virus, parainfluenza and Mumps and is associated with various respiratory illnesses, mumps, meningitis, pancreatitis, encephalitis and measles. Nipah virus was only recognised first in 1999 and it causes fatal encephalitis in 70% of infected patients and has an extremely broad host range including humans, dogs, cats, pigs, horses, hamsters, bats and guinea pigs. It is a critical threat to global health and economies (2005, Nature, 436, 401-405; Negrete, O. A., et al,);

Flaviviridae which includes Dengue, Yellow Fever, Hepatitis C and G and is associated with encephalitis, hepatitis and shock syndrome. Hep C for example, is an RNA virus with six main genotypes, is a major cause of chronic liver disease with over 170 million individuals infected worldwide and with no available vaccine, (2005, Science, 309, 623-626; Lindenbach, B. D., et al,);

Herpesviridae which includes human herpesvirus 1 through 8. These viruses can give rise to oral infections, ulceration of the cornea, genital tract infections, meningitis, chickenpox, pneumonia, shingles, cytomegaloviral mononucleosis and encephalitis. Human Cytomegalovirus causes severe and fatal diseases in immunocompromised individuals, including organ transplant individuals. In addition HHV8 has been implicated as the causative agent in the AIDS related condition Kaposi sarcoma. (2003, Nature, 424, 456-461; Wang, X., et al,);

Adenoviridae which includes human adenoviruses A through F. These viruses can give rise to respiratory diseases, infection of the kidney, conjunctivitis and diarrhoea;

Papillomaviridae which includes the Human papilloma virus types introduced above. These cause viral warts and neoplasms of the cervix, larynx and bladder;

Parvoviridae which includes the B19 virus and gives symptoms of Rubella without complication;

Hepadnaviridae which includes Hepatitis B, and which is associated with cirrhosis of the liver, and primary hepatocellular carcinoma;

Retroviridae which includes HTLV 1 and 2, HIV 1 and 2, associated with acute infections and various malignant neoplasms such as human T-cell leukemias;

Reoviridae which includes rotavirus and associated with diarrhoea, gastroenteritis and upper respiratory tract illness;

Filoviridae which includes Marburg and Ebola type viruses and associated with hemorrhagic fever;

Rhabdoviridae which includes vesicular stomatitis and Rabies and is associated with fever and Rabies;

Orthomyxoviridae which includes influenza A, B and C and is associated with the common cold and pneumonia;

Bunyaviridae which includes Crimean-Congo hemorrhagic fever virus, New York virus, and Hantavirus and is associated with acute fevers and pulmonary syndromes;

Arenaviridae which includes Lassa virus, lymphocytic choriomeningitis virus and is associated with encephalitis, meningitis and hemorrhagic fever;

Coronaviridae which includes human coronavirus and is associated with common cold symptoms and gastrointestinal symptoms;

Picornaviridae which includes human enteroviruses A through D and polio virus and is associated with bronchitis, meningitis, and paralysis;

Caliciviridae which includes Norwalk-like and Sapporo-like viruses and is associated with acute gaAroenteritis;

unassigned "Hepatitis E-like viruses" (HEV) associated with acute hepatitis;

Astroviridae which includes human astrovirus and is associated with enteritis and gastroenteritis; and Togaviridae which includes Ross River and Rubella and is associated with encephalitis, leucopenia and rash. Using the present invention, it is possible that viruses clinically classified as low risk actually may be high risk in individuals or animals of a particular genotype or ethnic lineage.

The nucleic acid molecules can be detected by any suitable detection means. Examples include, but not limited to:

providing a detector ligand capable of binding to a region of the nucleic acid molecule and allowing sufficient time for the detector ligand to bind to the region; and measuring binding of the detector ligand to the nucleic acid molecule to detect the presence of the nucleic acid molecule. It will be appreciated that the nucleic acid molecule can be detected by any suitable means known to the art.

When a virus-specific nucleic acid molecule has been obtained or identified for any given virus, probes or primers can be designed to ensure amplification of the region of interest in an amplification reaction. It is important to note that both strands of a treated and thus converted genome, (hereafter termed "derivative") can be analyzed for primer design, since treatment or conversion leads to asymmetries of sequence, (see below), and hence different primer sequences are required for the detection of the 'top' and 'bottom' strands of the same locus, (also known as the 'Watson' and 'Crick' strands). Thus, there are two populations of molecules, the converted genome as it exists immediately after conversion, and the population of molecules that results after the derivative is replicated by conventional enzymological means (PCR) or by methods such as isothermal amplification. Primers are typically designed for the converted top strand for convenience but primers can also be generated for the bottom strand. Thus, it will be possible to carry out clinical or scientific assays on samples to detect a given type of virus and target in the genome of the organism.

The present invention can use probes or primers that are indicative of representative types of virus which can be used to determine whether any virus is present in a given sample. Further virus type-specific probes can be used to actually detect or identify a given, type, subtype, variant and genotype examples of virus.

The present invention can use probes or primers that are indicative of targets such as methylation which can be used to determine whether the target is present in a given sample. Further target-specific probes can be used to actually detect or identify targets in the genome.

A real and unexpected advantage of the present invention is that it can be carried out in the one reaction tube or vessel. Not only is the virus assayed but also genomic targets or targets can be identified. The combination of the two test parameters in the one assay allows the assignment of a health state to the subject. The health state can be a disease such as cancer, pre-cancerous state, high risk for disease state, and the like. The present invention may be used as an early indication of a disease state or potential disease state that will allow early medical or veterinary or horticultural intervention to prevent further progression or cure the disease.

The present invention is particularly suitable of detecting viruses that have been implicated in disease states such as cancer. Examples include, but not limited to human papilloma virus, hepatitis, human immunodeficiency virus (HIV), and members of the various families of viruses described above.

The present invention is particularly suitable of detecting genomic targets in cells that have been implicated in disease states such as cancer. Depending on the disease or health state, potentially any gene, regulatory region or non-coding region in a genome, or its extranuclear or extracellular components, is a potential marker for use in the present invention.

The present inventors have obtained data that demonstrate that the methylation state of some genomic regions is indicative of cancer progression and that the progression is far more reliable in the case where the virus is present.

Using clinical samples and cell lines, the present inventors have examined methylation patterns in regulatory regions in the vicinity of nearly 400 human genes and have found over 60 genomic markers that have methylation changes when in a cancerous state together with the presence of HPV. Examples include, but not limited to, one or more of the following genomic regions CD14, ENDRB, HEC, RARB1, PGR, SFRS8, TMSB10, ABCG2, MFNG, LAMR1, RAGE, ABL1, CRBP, GPR37, HRK, RARA, SYK, ECE1, MME, TEM, NF2, XIAP, RARRES1, FLI1, HTLF, LDHB, RB1, TGD, CDK4, MMP14, RAB32, BARD1, NF1, LIM2, MMP2, DAB2, BMP6, CDKN1C, DAB2IP, LMNB1, MMP28, HAI2, SOCS1, HIC2, MSH6, RIN2, HMGA1, JUN, S100P*, SRF, VDR, DKK3, KRAS2, PLAU, TNFRSF10B, CDH1, MAC30, DDB2, PAX6, AXL, EIF4A2, SLIT2, RECK, TERC, GATA5, STAT1. Other regions include those shown in Table 8 below.

From the data obtained by the present inventors with HPV, it will be appreciated that each and every disease or health state may have particular genomic regions that could be used as markers in the present invention. The fact that about approximately 15% of genomic markers tested were only positive (methylated) when the sample was positive for HPV and was derived from a cancerous or pre-cancerous state indicates that there may be a large number of possible targets for any given disease or health state. Given that there are about 25,000 protein coding loci in the human genome, then 15% rate would predict about 4000 possible targets just using the regulatory regions of genes. There would be many more potential targets as specific CpG regions may be methylated in a particular disease or health state. The invention therefore encompasses all such possible markers. It will be appreciated that the present teaching can be used by a person skilled in the art to determine any useful genomic marker for any disease or health state.

In a fifth aspect, the present invention provides an assay for screening for potential cervical cancer in a subject comprising:

(a) treating a sample from the subject with bisulphite reagent under conditions that cause unmethylated cytosines in human papilloma virus (HPV) and genomic nucleic acid to be converted to uracil to form derivative HPV nucleic acid and derivative genomic nucleic acid;

(b) providing primers capable of binding to regions of derivative HPV nucleic acid, the primers being capable of allowing amplification of a desired HPV-specific nucleic acid molecule of the derivative HPV nucleic acid;

(c) providing primers capable of binding to regions of derivative genomic nucleic acid, the primers being capable of allowing amplification of a desired genomic-specific nucleic acid molecule of the derivative genomic nucleic acid;

(d) carrying out an amplification reaction on the derivative HPV nucleic acid and derivative genomic nucleic acid; and (e) assaying for the presence of an amplified HPV nucleic acid product and an amplified genomic nucleic acid product, wherein detection of one or both products is indicative of progression to a cervical cancer state in the subject.

In a preferred form, the assay further includes:

(f) testing a sample having the presence of a HPV to determine the type, subtype, variant or genotype of the HPV in the sample.

For HPV16 detection for example, primers capable of binding to the derivative HPV16 viral nucleic acid can be prepared. It will be appreciated that derivative HPV nucleic acid can be determined for all other HPV types by changing all cytosines to uracils in the respective genome sequences as carried out for HPV16. Such a conversion depicts the result of treating the viral nucleic acid in a sample carried out in step a of the assays according to the present invention.

It will be appreciated that other suitable primers or probes can be devised that are capable of binding to derivative HPV viral nucleic acid from other HPV types.

In a sixth aspect, the present invention provides a kit for use in an assay for determining a health state in a subject comprising probes or primers for a virus-specific nucleic acid molecule and probes or primers for a genome-specific nucleic acid molecule together with one or more reagents or components for an amplification reaction such as PCR.

The sample includes, but not limited to, swab, biopsy, smear, Pap smear, surface scrape, spatula, and fluid samples, as well as samples from different storage media such as frozen material, paraffin blocks, glass slides, forensic collection systems and archival material.

Any population of organisms, including animals and humans, as well as plants, will have individuals that are resistant to long term viral effects. Hence, the combination of viral presence and genomic marker such as genomic methylation should distinguish whether an organism will have or is likely to have a disease state. The present invention is suitable for human applications as well as veterinary and other organism-based endeavours. For example, the present invention may have uses in all domestic live-stock where there is sufficient indication that genomic methylation occurs, and even as a management tool for monitoring wildlife populations.

In essence, the invention relates to assaying at two levels: one is for the presence of a virus, and the other is for the presence, absence or status of a genomic or nucleic acid target inferred from a particular amplification product or lack of amplification. The target can be a methylation status, nucleic acid sequence, or lack of a nucleic acid sequence, or altered nucleic acid sequence. In some advanced cancers, the genomic target may be completely deleted, and hence the lack of its presence will be diagnostic. This in itself may be an excellent diagnostic tool and is covered by the present invention. In addition, many cancers have extra-chromosomal amplicons termed double-minutes, and hence they are not strictly genomic, in that they do not reside in one of the 46 chromosomes. Similarly, any mitochondrial DNAs, or DNAs contained with cytoplasmic or nuclear organelles are covered by the present invention.

The present inventors have developed a combinational technology which when used in a single tube, for example, is far more powerful than either technologies used alone in assessing the risk for progression of a population of cells proceeding towards the cancerous trajectory. Typically the genomic methylation of one or a small number of genomic targets would be done in the one tube. The assay is powerful when the patient samples containing both viral genomes and host genomic DNA (or RNA) are converted by the use of sodium bisulphite into a simplified forms that can be used simultaneously for the detection of both viral presence and altered host methylation profiles.

Modifying nucleic acid can be the conversion of an unmethylated cytosine to another nucleotide. Preferably, the agent modifies unmethylated cytosine to uracil which is then replaced as a thymine during amplification of the derivative nucleic acid. Preferably, the agent used for modifying unmethylated cytosine is sodium bisulfite. Other agents that similarly modify unmethylated cytosine, but not methylated cytosine can also be used in the assays of the invention. Examples include, but not limited to bisulfite, acetate or citrate. Preferably, the agent is sodium bisulfite, a reagent, which in the presence of acidic aqueous conditions, modifies cytosine into uracil.

Sodium bisulfite ($NaHSO_3$) reacts readily with the 5,6-double bond of cytosine to form a sulfonated cytosine reaction intermediate which is susceptible to deamination, and in the presence of water gives rise to a uracil sulfite. If necessary, the sulfite group can be removed under mild alkaline conditions, resulting in the formation of uracil. Thus, potentially all cytosines will be converted to uracils. Any methylated cytosines, however, cannot be converted by the modifying reagent due to protection by methylation.

Throughout this specification, unless the context requires otherwise, the word "comprise", or variations such as "comprises" or "comprising", will be understood to imply the inclusion of a stated element, integer or step, or group of elements, integers or steps, but not the exclusion of any other element, integer or step, or group of elements, integers or steps.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia before the priority date of each claim of this specification.

In order that the present invention may be more clearly understood, preferred embodiments will be described with reference to the following drawings and examples.

MODE(S) FOR CARRYING OUT THE INVENTION

Definitions

Figure 1A:
FIG. 1 shows High-Risk HPV testing and HPV typing of various human samples including; the HeLa cell line; samples from two individuals, (1 and 2), designated as having High Grade Squamous Intraepithelial Lesions, (designated HSIL-1 and HSIL-2); two individuals with normal cytology, (designated as Normal-1 and Normal-2); and an individual with no cytological indications of a cancerous state, (designated HPV+Nor), but nevertheless inferred to have an HPV infection on the basis of cellular phenotype as determined by an expert pathologist. A. Determination of High-Risk HPV types in six different samples using a Universal primer for high-medium risk HPV types; B. Test for HPV using complexity reduced primer sets specific for HPV types 16, 18, 31, 33, 35, 39, 45, 51, 52, 56, 58 and 59 and primer sets 42, 43, 44, 53, 54, 55, 66, 68, 73, 82, 83 and 84 in the case of the normal tissue sample.

The term "subject" as used herein means refers to an organism that has genomic methylation at cytosines. This typically includes Mammalia such as animals and humans as well as many plant species.

The term "health state" as used herein means the degree to which an individual differs from that of the general population in terms of a readily definable disease or affliction. For humans this is defined by the World Heath Organization with its International Classification of Diseases which is the standard diagnostic classification for all general epidemiological and health management purposes. In clinical terms the health state can be assayed using criteria set out in Harrisons; Principles of Internal Medicine, Braunwald, E et al., eds, McGraw Hill, Medical Publishing Division, 15$^{th}$ and later editions.

The term 'status of a genomic target' as used herein can include the presence or absence of a target nucleic acid (chromosomal or extra-chromosomal), methylation or non-methylation of a genomic target, where that target can be a nucleic acid that is a normal or polymorphic resident of a particular cell type within that population of organisms, or a target that has been introduced via an infectious microorganism or virus, or a target that has responded by amplification, mobilization, inversion or translocation as a result of an external perturbogen.

The term "modifies" as used herein means the conversion of an unmethylated cytosine to another nucleotide. Preferably, the agent modifies unmethylated cytosine to uracil which is then replaced as a thymine during amplification of the modified nucleic acid.

The term 'complexity-reduction' as used herein in the broad sense, means that a DNA genome, whether occurring naturally in a eukaryotic, prokaryotic, or viral/viroid life form, or being synthetically manufactured, (or if occurring naturally as an RNA virus/viroid genome then after copying to a cDNA form), which contains the four common bases G, A, T and C, undergoes an increase in the frequency of Ts and a decrease in the frequency of Cs as a result of the bisulphite modification. This transition changes what was once a normal genome to a sequence of polymers, termed the 'derivatives', that have no functional biological significance and consist of 'genomic ghosts'.

The term 'Complexity-reduction' used herein does not refer to the order in which bases occur in a derivative population, such as any mathematical complexity difference between a sequence that is ATATATATATATAT (SEQ ID NO: 76) versus one of the same length that is AAAAAAATTTTTTT (SEQ ID NO: 77). 'Complexity-reduction' as used herein refers to an unchanged position of bases in two entities, (one a real genome and the other a derivative), that are accessed by molecular probes or primers with both the original genome and its converted derivative having bases of interest at invariant positions 1 to n. In the case of the 3 billion base pair haploid human genome of a particular human female, the invariant positions on the 'top' strand are defined as being from 1 to n, where n is position 3,000,000,000. If in the sequence 1 to n, the i$^{th}$ base is a C in the 'top strand' of the original genome, then the i$^{th}$ base is a U in the converted human derivative. In the case of the 7904 base pair HPV16 viral genome, the invariant positions are defined as being from 1 to 7904, where n is 7904. If in the sequence 1 to n, the i$^{th}$ base is a C in the 'top' strand of the original genome, then the i$^{th}$ base is a U in the converted HPV derivative. It will be appreciated that when different types of HPV derivatives or types are used for alignments and when those viral derivatives differ in length, then determining the correct i$^{th}$ base requires careful bioinformatic multiple alignments, as instantiated by Morgenstern, B. et al., Proc. Natl. Acad. Sci. USA. 93, 12098-12103 for normal multiple genomic alignments.

An example clarifies the consequences of such a conversion process when applied to individual viral genomes, or to a mixture of viral genomes that occurs in a clinical sample containing both human cells and viral genomes, or parts thereof.

A normal 10 base genomic sequence which is 5' GGGGAAATTC 3' (SEQ ID NO: 78) (the 'top' strand) will have a complementary 'bottom' strand that is 5' GAATTTCCCC 3' (SEQ ID NO: 79). Following denaturation and bisulphite treatment, the 'top' strand becomes 5' GGGGAAATTU 3' (SEQ ID NO: 80) and the 'bottom' strand becomes 5' GAATTTUUUU 3' (SEQ ID NO: 81). Since cytosines have been converted to uracils, and uracils are equivalent to thymines in terms of recognition by DNA polymerse machinery ex vivo, the top strand derivative is essentially 5' GGGGAAATTT 5' GGGGAAATTT 3' (SEQ ID NO: 82) and the bottom strand derivative is 5' 5' GAATTTTTTT 3' (SEQ ID NO: 83). Thus an initially normal genome has been converted from one in which the top and bottom strands between them had 5 Cs and 5 Ts, to a derivative population of polymers in which the top and bottom strands between them now have no Cs and 10 Ts. The normal genome has been reduced from a four base entity to a three base derivative. It has been 'complexity-reduced". In addition, a 'locus' in a derivative population refers only to positional coordinates within that derivative. After bisulphite conversion for example, a locus is stripped of all functional biological characteristics at any network level. If it was previously coding, regulatory or structural, it is now biological gibberish in both strands. A derivative population is thus a collection of functionless chemical polymers that now represent two non-complementary ghosts of the previously complementary strands of a genome that is now informationally impotent. Furthermore, the derivatives are unique and do not represent, except by statistical accident, sequences generated by normal evolutionary processes in any cellular, (or viral or viroid), life forms.

Probes and Complexity-Reduction

In the formal sense of molecular probes, the present inventors define herein 'complexity-reduction' in terms of the increase in probe length (IPL) that is required to achieve the same specificity and level of hybridization of a probe to a specific locus, under a given set of molecular conditions in two entities of the same size, the first being the normal genome and the second being the 'converted' entity, (the derivative). For the purposes of molecular utility, IPL is an integer equal to or greater than 1. Each locus remains in the same location in the normal genome as well as the converted derivative.

In practical terms, 'complexity-reduction' can be measured in probe lengths. For example, on average, an 11-mer oligonucleotide probe will have a unique location to which it will hybridize perfectly in a set of normal genomes of 4,194,304 bases consisting of the four bases G, A, T and C ($4^{11}$ equals 4,194,304). However, once such an initial genome of 4,194,304 bases has been converted by the HGS bisulphite methodology, the converted derivative is now T-enriched and is less complex. However, the consequence of this decrease in complexity is that the previously unique 11-mer probe no longer has a unique site to which it can hybridize within the complexity-reduced derivative, since other newly arisen locations of 11 base sequences will have arisen de novo as a consequence of the bisulphite conversion. These newly arisen sequences are referred to herein as decoy loci. It will thus now require an approximately 14-mer probe to find and hybridize to the original locus. In this example, the increase in probe length is approximately from zero to 3 bases.

Although it may appear counter intuitive, an increased oligonucleotide probe length may be required to detect the original locus in what is now a T-enriched derivative. Thus the reduced-complexity of a derivative means longer probes may need to be designed for the 'top' and 'bottom' strands of a locus to find the original unique site in the derivative. However, as shown below, the use of Intercalating Nucleic Acid (INA) probes allows for much shorter probes than conventional oligonucleotides, and so overcomes this requirement for increased lengths.

'Complexity-reduction' as used herein also applies to the different structures of probe sequences that can be used in determining the presence of HPV in a sample. In addition, such probes may have non-conventional backbones, such as that of PNA, or they can have modified additions to a backbone such as those described in INA. Thus a derivative is considered to have reduced-complexity irrespective of whether the probe has additional components such as intercalating pseudonucleotides (as in INA). Examples include, but are not limited to, DNA, RNA, locked nucleic acid (LNA), peptide nucleic acid (PNA), MNA, altritol nucleic acid (ANA), hexitol nucleic acid (HNA), intercalating nucleic acid (INA), cyclohexanyl nucleic acid (CNA) and mixtures thereof and hybrids thereof, as well as phosphorous atom modifications thereof, such as but not limited to phosphorothioates, methyl phospholates, phosphoramidites, phosphorodithiates, phosphoroselenoates, phosphotriesters and phosphoboranoates. Non-naturally occurring nucleotides include, but not limited to the nucleotides comprised within DNA, RNA, PNA, INA, HNA, MNA, ANA, LNA, CNA, CeNA, TNA, (2'-NH)-TNA, (3'-NH)-TNA, a-L-Ribo-LNA, a-L-Xylo-LNA, 1'-D-Xylo-LNA, a-D-Ribo-LNA, [3.2.1]-LNA, Bicyclo-DNA, 6-Amino-Bicyclo-DNA, 5-epi-Bicyclo-DNA, a-Bicyclo-DNA, Tricyclo-DNA, Bicyclo [4.3.0]-DNA, Bicyclo[3.2.1]-DNA, Bicyclo[4.3.0]amide-DNA, β-D-Ribopyranosyl-NA, a-L-Lyxopyranosyl-NA, 2'-R-RNA, a-L-RNA or a-D-RNA, β-D-RNA. In addition non-phosphorous containing compounds may be used for linking to nucleotides such as but not limited to methylimino-methyl, formacetate, thioformacetate and linking groups comprising amides. In particular nucleic acids and nucleic acid analogues may comprise one or more intercalator pseudonucleotides (IPN). The presence of IPN is not part of the complexity description for nucleic acid molecules, nor is the backbone part of that complexity, such as in PNA.

By 'INA' is meant an intercalating nucleic acid in accordance with the teaching of WO 03/051901, WO 03/052132, WO 03/052133 and WO 03/052134 (Human Genetic Signatures Pty Ltd) incorporated herein by reference. An INA is an oligonucleotide or oligonucleotide analogue comprising one or more intercalator pseudonucleotide (IPN) molecules.

By 'HNA' is meant nucleic acids as for example described by Van Aetschot et al., 1995.

By 'MNA' is meant nucleic acids as described by Hossain et al, 1998.

'ANA' refers to nucleic acids described by Allert at al, 1999.

'LNA' may be any LNA molecule as described in WO 99/14226 (Exiqon). Preferably, LNA is selected from the molecules depicted in the abstract of WO 99/14226. More preferably, LNA is a nucleic acid as described in Singh et al, 1998, Koshkin et al, 1998 or Obika et al., 1997.

'PNA' refers to peptide nucleic acids as for example described by Nielsen et al, 1991.

The principle of complexity-reduction, defined in terms of probe lengths and different probe sequences for 'top' and 'bottom' strands at a locus, is a relative term applicable to different structural or modified probes and primers in different molecular milieu. An example for INAs clarifies this relativity. The significant advantages of INAs over the standard oligonucleotide probes are that INAs can be made much shorter than conventional oligonucleotides and still achieve equivalent hybridization results, (INA length<oligonucleotide length). This is due to the high affinity of INA for complementary DNA owing to the Intercalating Pseudo Nucleotides, IPNs, that are a structural component of INAs. Thus if it requires an INA of length X nucleotides, with a given number of IPNs, to achieve successful and specific hybridization to an unconverted genome, it will still require an INA of length>X to hybridize to the same locus in a bisulphite converted genome under the same molecular conditions.

It is also particularly important to note that in the case of host-pathogen interactions, (where both viral and host genomes co-exist in the same clinical sample but in very different concentrations), 'complexity-reduction' and the use of INAs introduce new advantageous conditions into hybridization protocols, particularly since INAs have a preference for hybridizing to nucleic acid sequences that are AT-enriched. For example, in a pure solution of unconverted HPV DNA, the approximate length of a viral probe or primer that is required to find and hybridize to a unique locus in the 7904 base HPV16 genome is approximately a 6-mer probe/primer, ($4^6$ equals 4096 bases). Following bisulphite treatment to generate a T-enriched HPV derivative, it now requires an approximately 8-mer probe or primer to find this unique location, ($3^8$ equals 6561 bases) under the same molecular conditions.

However, when two grossly unequally sized genomes are initially present in a sample, such as the HPV genome of 7904 base pairs and the human genome of approximately 3,000,000,000 base pairs, and both genomes are 'complexity-reduced' to their respective derivatives, the probes or primers for a unique viral sequence now hybridize to their derivative targets in a solution that is overwhelmingly dominated by the T-enriched human derivative. If, for example, there was one HPV derivative for each human derivative in the sample, then viral probes or primers are hybridizing to a 3,000,007,904 base pair derivative. Hence assaying for a unique viral sequence now requires approximately 14-mer probes or primers, to avoid hybridization signals emanating from viral decoy loci that have newly arisen in human sequences.

In addition to 'complexity-reduction' issues involving probe and primer lengths, there are also important changes to the kinetics of hybridization and the ability to detect PCR products when the number of degenerate primers used in a PCR reaction is modest. Owing to the extensive genomic variation between HPV types, prior art amplifications have required the use of a large number of degenerate primers to produce relevant amplified nucleic acid products or amplicons from multiplex PCR reactions. However, the greater the degeneracy in the probe/primer pool, the lower is the concentration of any individual relevant probe or primer in solution. Such a situation has analogies to the kinetics and fidelity of hybridizations in the driver-tracer reactions carried out on complex eukaryotic genomes, and first introduced into the scientific literature in 1966 by Waring, M. & Britten R. J. Science, 154, 791-794; and in 1968 by Britten, R. J and Kohne D E., Science, 161, 529-540, (and earlier references therein that stem from the Carnegie Institution of Washington Yearbook reports).

In addition, when HPV PCR primers are in high concentration relative to human derivatives, the dominant force in the hybridization reaction is the HPV primer. For example, if the viral load in a sample is high, (say of the order of 100,000 HPV genomes to a single human genome), then the kinetics of hybridization of viral primers would be a 100,000 times faster than if there were only one HPV derivative per human derivative. In the former case the viral component behaves in solution as if it were a highly repetitive component of a genome. However, in order to detect different HPV types of different risk in a clinical sample by means of a single PCR reaction, different primers are typically required from each HPV type necessitating the use of degenerate entities. The net result is that the primer population can be combinatorially staggering in a conventional multiplex PCR reaction on mixed normal genomes. There can literally be thousands of different primers competing for hybridization sites with the net result that PCR amplifications fail, or the amplified nucleic acid product distribution becomes heavily biased in favor of a particular HPV type present in the sample. This presents a major problem for the generation of data from clinical samples in which conventional unconverted genomes are present.

The present invention of 'complexity-reduction', combined with the optional use of INA probes and primers overcomes many of the difficulties of these prior art problems.

Primers and Complexity-Reduction

It should be noted that complexity-reduction differs depending upon whether the population of molecules that has been converted, (the derivatives), remains in the converted state, or is subjected to further amplification. In the examples discussed above, the derivative population remained unamplified, as it would exist in a clinical sample. Recall that the top strand (5' GGGGAAATTC 3') (SEQ ID NO: 78), and the bottom strand (5' GAATTTCCCC 3') (SEQ ID NO: 79), were converted to 5' GGGGAAATTU 3' (SEQ ID NO: 80) and 5' GAATTTUUUU 3' (SEQ ID NO: 81) respectively. Since cytosines have been converted to uracils, and uracils are equivalent to thymines in terms of recognition by DNA polymerse machinery ex vivo, the top strand derivative is essentially 5' GGGGAAATTT 3' (SEQ ID NO: 82) and the bottom strand derivative is 5' GAATTTTTTT 3' (SEQ ID NO: 83). However, if the derivative population is now replicated ex vivo by enzymological means, four distinct derivative populations ensue, these being [5' GGGGAAATTT 3' (SEQ ID NO: 82)], [5' AAATTTCCCC 3' (SEQ ID NO: 84)], [5' AAAAAAATTC 3' (SEQ ID NO: 85)] and [5' GAATTTTTTT 3' (SEQ ID NO: 86)]. These derivatives are indeed complexity reduced, but not to the same extent as the original unreplicated derivatives that exist immediately after conversion. Hence when PCR primers are made to the original non-replicated derivative strands, it is necessary to judiciously decide which amplified nucleic acid products one wishes to examine, as the choice of primers to either the top or bottom strands will influence the output. The differences between dealing with two non-complementary derivative populations that constitute the output of a converted genome, versus the four derivative populations that exist after replication are not intuitively clears, but can have important implications for primer design.

Finally, the issue of longer probes or primers that was introduced earlier to formalize and quantitated 'complexity-reduction' only assumes relevance when searching for a unique sequence within a derivative population of molecules. An important foundation of the present invention, however, can be the choice of derivative loci that are maximally similar between virus types, allowing all virus types to be assayed in one initial test, if required. These chosen loci will vary depending upon whether the top or bottom strand derivatives are chosen and such loci will be in different regions in the top strand as compared to the bottom strand.

The practical importance of the requirement for longer probes and primers in derivative populations is overshadowed by the practical advantages that are gained for virus detection owing to the generation of loci that are rendered more sequence similar by conversion using the HGS bisulphite treatment in the present invention. They are also overshadowed by the optional use of INAs that allow for shorter probe and primer molecules than is the case for conventional oligonucleotides. In addition, application of the nested PCR approach to derivative populations requires two primers to bind in the same neighbourhood in order to allow for amplified nucleic acid product production. If one of the PCR primers has sequence similarity to a decoy locus that is outside the targeted neighbourhood, it is unlikely that the other member of its primer pair would also have a decoy locus nearby in the same non-targeted region. It is even more unlikely that the inner primers of such a nested PCR approach would again have decoy loci in the same non-targeted region as the first round primers. The probability of spurious amplification is extremely unlikely.

The term "viral-specific nucleic acid molecule" as used herein means a molecule which has been determined or obtained which has one or more sequences specific to a virus or virus type.

The term 'taxonomic level of the virus' as used herein includes type, subtype, variant and genotype. The fluidity of viral genomes is recognized. Different viral populations may furthermore be polymorphic for single nucleotide changes or be subject to hyper- or hypo-mutability if they reside within certain cancerous cells where normal DNA repair processes are no longer functioning.

The term "virus-specific nucleic acid molecule" as used herein means a specific nucleic acid molecule present in treated or converted viral DNA which can be indicative of the virus or virus type.

The term "virus type" as used herein refers to any existing or new virus populations where there is less than 90% sequence similarity with previously isolated and characterized virus types.

The term "virus subtype" as used herein refers to any existing or new virus populations where the sequence similarity is in the 90-98% range relative to previous subtypes.

The term "virus variant" as used herein refers to any existing or new virus populations where the sequence similarity is between 98-100% of previous variants.

The term "HPV genotype" as used herein is as follows. A genotype is any fully sequenced HPV genome that minimally differs by one base from any other fully sequenced HPV genome including whether that single base exists as either a G, A, T or C, or whether the base at a given position in the standard comparator, (namely HPV16 from position 1 to position 7904) has been altered by deletion, addition, amplification or transposition to another site. The present inventors compared all other HPV genotypes relative to the HPV16 standard using prior art BLAST methodologies.

The term "HPV-specific nucleic acid molecule" as used herein means a specific nucleic acid molecule present in treated or converted viral DNA which can be indicative of the virus or virus type.

The term "HPV type" as used herein refers to any existing or new HPV population where there is less than 90% sequence similarity with previously isolated and characterized HPV types, (1993, Van Rast, M. A., et al., Papillomavirus Rep, 4, 61-65; 1998, Southern, S. A. and Herrington, C. S., Sex. Transm. Inf. 74, 101-109).

The term "HPV subtype" as used herein refers to any existing or new HPV population where the sequence similarity is in the 90-98% range relative to previous subtypes, (1993, Van Rast, M. A., et al., Papillomavirus Rep, 4, 61-65; 1998, Southern, S. A. and Herrington, C. S., Sex. Transm. Inf. 74, 101-109).

The term "HPV variant" as used herein refers to any existing or new HPV population where the sequence similarity is between 98-100% of previous variants, (1993, Van Rast, M. A., et al., Papillomavirus Rep, 4, 61-65; 1998, Southern, A. and Herrington, C. S. Sex. Transm. Inf. 74, 101-109).

The term "HPV genotype" as used herein is as follows. A genotype is any fully sequenced HPV genome that minimally differs by one base from any other fully sequenced HPV genome including whether that single base exists as either a G, A, T or C, or whether the base at a given position in the standard comparator, (namely HPV16 from position 1 to position 7904) has been altered by deletion, addition, amplification or transposition to another site. The present inventors compared all other HPV genotypes relative to the HPV16 standard using prior art BLAST methodologies.

Table 1 provides a list of oligonucleotide primers that have produced HPV-specific products from liquid based cytology samples from human patients. All primers are directed to the top strand derivatives of the different HPV types. The designations of the primers are as follows:

HPV type-derivative region-primer number as per design below.

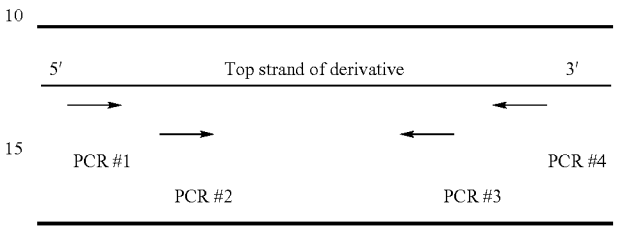

For example the top row illustrates primer #1 for HPV16 in the E7 derivative region.

The HPV-Uni and HPV-HM designations represent the degenerate oligonucleotide primers. Non standard designations are as defined previously.

TABLE 1

| Designation | Sequence | SEQ ID NO: |
|---|---|---|
| HPV16-E7-1 | TATGTATGGAGATATATTTATATTGT | 1 |
| HPV16-E7-2 | GTTATGAGTAATTAAATGATAGTTT | 2 |
| HPV16-E7-3 | TAAAACACACAATTCCTAATATAC | 3 |
| HPV16-E7-4 | CCCATTAATACCTACAAAATCAAC | 4 |
| HPV16-E6-1 | GAAAGTTATTATAGTTATGTATAGAGT | 5 |
| HPV16-E6-2 | ATTAGAATGTGTGTATTGTAAGTAAT | 6 |
| HPV16-E6-3 | ACTACAATATAAATATATCTCCATAC | 7 |
| HPV16-E6-4 | AAACTATCATTTAATTACTCATAAC | 8 |
| HPV16-E4-1 | GAATATATTTTGTGTAGTTTAAAGATGATGT | 9 |
| HPV16-E4-2 | GTTTTATATTTGTGTTTAGTAGT | 10 |
| HPV16-E4-3 | CCTTTTAAATATACTATAAATATAATATTAC | 11 |
| HPV16-E4-4 | CACACAATATACAATATACAATAC | 12 |
| HPV18-E7-1 | GTATGGATTTAAGGTAATATTGTAAGAT | 13 |
| HPV18-E7-2 | GTATTTAGAGTTTTAAAATGAAATTT | 14 |
| HPV18-E7-3 | AACACACAAAAAACAAAATATTC | 15 |
| HPV18-E7-4 | ACCATTATTACTTACTACTAAAATAC | 16 |
| HPV18-E6-1 | GATAGTATATAGTATGTTGTATGTT | 17 |
| HPV18-E6-2 | ATTTAGATTTTGTGTATGGAGATAT | 18 |
| HPV18-E6-3 | ATCTTACAATATTACCTTAAATCCATAC | 19 |
| HPV18-E6-4 | AAATTTCATTTTAAAACTCTAAATAC | 20 |
| HPV18-E4-1 | GGGAATATAGGTAAGTGGGAAGTAT | 21 |
| HPV18-E4-2 | GATTGTAATGATTTTATGTGTAGTATT | 22 |
| HPV18-E4-3 | AAATAATATATCTCTATAATAATC | 23 |

TABLE 1-continued

| Designation | Sequence | SEQ ID NO: |
|---|---|---|
| HPV18-E4-4 | TTCATTACCTACACCTATCCAATACC | 24 |
| HPV56-E7-1 | GATTTATAGTGTAATGAGTAATTGGATAGT | 25 |
| HPV56-E7-2 | GGTTATAGTAAGTTAGATAAGT | 26 |
| HPV56-E7-3 | TCCCCATCTATACCTTCAAATAAC | 27 |
| HPV56-E7-4 | CCTATTTTTTTTCTACAATTAC | 28 |
| HPV31-E7-1 | GTAATTGATTTTATTGTTATGAGT | 29 |
| HPV31-E7-2 | GTTATAGATAGTTTAGTTGGATAAGT | 30 |
| HPV31-E7-3 | CTAAATCAACCATTATAATTACAATC | 31 |
| HPV31-E7-4 | CCTATCTATCTATCAATTACTAC | 32 |
| HPV33-E7-1 | TTTTGTATATGGAAATATATTAGAAT | 33 |
| HPV33-E7-2 | TAGGTGTATTATATGTTAAAGATT | 34 |
| HPV33-E7-3 | CCTCATCTAAACTATCACTTAATTAC | 35 |
| HPV33-E7-4 | TAACTAATTATACTTATCCATCTAAC | 36 |
| HPV35-E7-1 | AAATAATGTAATAAATAGTTATGTT | 37 |
| HPV35-E7-2 | GTTGTGTTTAGTTGAAAAGTAAAGAT | 38 |
| HPV35-E7-3 | CCATATATATACTCTATACACACAAAC | 39 |
| HPV35-E7-4 | AAACACACTATTCCAAATATAC | 40 |
| HPV39-E7-1 | TTAAAGTTTATTTTGTAGGAAATTG | 41 |
| HPV39-E7-2 | GATTTATGTTTTTATAATGAAATATAGT | 42 |
| HPV39-E7-3 | CTAATAAATCCATAAACAACTAC | 43 |
| HPV39-E7-4 | CATAACAAATTACTAATTTACATTTAC | 44 |
| HPV58-E7-1 | TATTTTGAATTAATTGATTTATTTTGT | 45 |
| HPV58-E7-2 | ATGAGTAATTATGTGATAGTTT | 46 |
| HPV58-E7-3 | ATACATATACCCATAAACAACTAC | 47 |
| HPV58-E7-4 | TTATTACTATACACAACTAAAAC | 48 |
| HPV6-E7-1 | GATATTTTGATTATGTTGGATATGT | 49 |
| HPV6-E7-2 | GTTGAAGAAGAAATTAAATAAGAT | 50 |
| HPV6-E7-3 | TACTATCACATCCACAACAACAAATC | 51 |
| HPV6-E7-4 | CTCTAATATCTATTTCTATACACTAC | 52 |
| HPV11-E7-1 | GTTATGAGTAATTAGAAGATAGT | 53 |
| HPV11-E7-2 | ATTATTAAATATTGATTTGTTGT | 54 |
| HPV11-E7-3 | ATACCTATAATATACTCTACTATAAC | 55 |
| HPV11-E7-4 | CAAAATTTTATATAATATACCTATC | 56 |
| HPV42-E7-1 | GTATATAGTGGAGAAAGAAATTGGAT | 57 |
| HPV42-E7-2 | GAATAATAAATTAGATGTGTTTTGTGTT | 58 |
| HPV42-E7-3 | CCAATTATTCATAACAATACAAATC | 59 |
| HPV42-E7-4 | ACTTAATCATCTTCATCTAAAC | 60 |
| HPV53-E7-1 | TAGTGTAYGGGGTTAGTTTGGAAGT | 61 |
| HPV53-E7-2 | ATTTGATTTATTAATAAGGTGT | 62 |
| HPV53-E7-3 | CTATAATATATTATAAAAATATTAATAC | 63 |
| HPV53-E7-4 | CAATTACTCATAACATTACAAATC | 64 |
| HPV-Uni-1 | GATGGKGATATGRTDSATRTWGGDTWTGG | 65 |
| HPV-Uni-2 | TAARTATTTWGATTATWTDDRAATG | 66 |
| HPV-Uni-3 | TATTWTAWCCYTAHRCHYWHTAHAACCA | 67 |
| HPV-Uni-4 | AMAAAHAMHTAATTHYHMMAACAWAYACC | 68 |
| HPV-HM-1 | GATTTDKWDTGTWATGAGTAATT | 69 |
| HPV-HML-1 | GRKTTDKWDTGTWRKGARTAATT | 70 |
| HPV-HM-2 | RRYRRKTTAGABGADGA | 71 |
| HPV-HML-2 | RRHRRKTTWGANKWDGA | 72 |
| HPV-HM-3 | YDATACCTWCWMAWWHVDCCAT | 73 |
| HPV-HML-3 | YDATACCTWHWHHDWHNDCCAT | 74 |
| HPV-HML-4 | ACHHHAAACCAHCCHHWACAHCC | 75 |

Virus Assay

The virus detection used as the first part of assay according to the present invention can also be combined with other assays of quite different types for the evaluation of changed cellular status within a cell population, for risk assessment underpinned by deranged transcriptomic, proteomic, metabolite or methylomic networks within infected cells, for monitoring the progression of an infection and for evaluating a therapeutic regimen such as antiviral therapy.

For example, a molecular assay measuring virus specific nucleic acid molecules can be combined with:

assays using pattern recognition and high throughput robotic imaging technology such as the Multi-Epitope-Ligand-Kartographie (MELK) system for automated quantitation of fluorescent signals in tissue sections, assays using light, confocal, transmission or electron microscopic analyses for Fluorescent in Situ Hybridizations (FISH), cytological or histological analyses that detect gross levels of chromosomal disturbance within cells, such as aneuploidy, or abnormal organelles (in terms of number, type or morphological appearance), assays using nucleic acid or polypeptide aptamers; Spiegelmers, (mirror image high-affinity oligonucleotide ligands); multicoloured nanocrystals (quantum dot bioconjugates), for ultrasensitive non-isotopic detection of molecules, or biomarkers for cell surface or internal components; combinatorial chemistry approaches involving Systematic Evolution of Ligands by Exponential Enrichment (SELEX) and high affinity aptamer ligands targeted to different cellular components, assays using laser-capture of cells or immunomagnetic cell enrichment technologies, or microsphere-based technologies interfaced with flow cytometry, or optical bar-coding of colloidal suspensions containing various nucleic acid or peptide/protein moieties, assays using single cell comparative genomic hybridization aimed at detecting gross genomic imbalances such as duplications, deficiencies, transpositions, rearrangements and their associated in situ technologies, assays reporting on transcriptomic modulations, such as robogenomic microarray technologies including Serial Analysis of Gene Expression (SAGE), Total Gene Expression Analyses, (TOGA), randomly ordered addressable high density fiber-optic sensor arrays, Massively Parallel Signature Sequencing (MPSS) on microbeads, assays reporting on proteomic modulations using various technologies including cellular analyses via protein microarrays, Matrix Assisted Laser Desorption Ionization-Time of Flight (MALDI-TOF) methods, Fourier Transformed Ion Cyclotron Resonance Mass Spectrometry, (FTICR), LC MS-MS and Rapid Evaporative cooling Mass Spectrometry, (RapEvap MS), assays using Multi Photon Detection (MPD) technologies where the detection levels approach zeptomole ($10^{-21}$) sensitivity, assays using methylomic technologies to interrogate the methylome of cells from clinical samples to determine the position of a the cell population along a given trajectory from normalcy to cervical cancer; preferably to determine the altered methylation signature of genomic loci in cells which are affected by viral infection, or immune cells which have been recruited to the site of infection or inflammation.

Some of the above technologies have been previously evaluated (2001, Miklos and Maleszka, Proteomics, 1, 30-41).

Data Collection, Integration and Management Systems

The data collection and the data management systems for the disclosed material associated with the present invention can be combined with clinical patient data and analysed using specialized algorithmic methods. Robotic platform management and data collection can be automatically stored and the collected data combined with an informatics infrastructure and software tools that interface with gene ontologies, (GO), with disease ontologies as exemplified by the National Library of Medicine's Medical Subject Headings (MeSH) thesaurus, the Online Mendelian Inheritance in Man, (OMIM), or with knowledge databases such the Human Genome Mutation Database (HGMD) or PubMed. Software pipelines that interface with the latest human genome assemblies and provide access to, and downloading of, information from sources such as Genbank and RefSeq, can be combined with assays reporting on the genomic status of cells that are HPV infected, or that have been influenced by cells owing to HPV presence elsewhere in the body.

The database infrastructure integrating HPV data with clinical and relevant bioinformatics data can, for example, utilize a loosely-coupled modular architecture which facilitates better software engineering and database management. A relational database management system (RDBMS), (such as Postgresql version 7.3) is open source and robust, and serves as an example of part of an integrated system to evaluate and better predict clinical outcomes in the HPV arena. Additional features involving web based Graphical User Interfaces (GUI) would allow for integrated cytological and histological analysis to be combined with molecular HPV data together with therapeutic and pharmaceutical data available in very diverse formats. The integration of enhanced digital technology for image analysis, remote image sharing by pathologists and automated visualization systems is envisaged as an integrated part of an automated molecular kit platform.

Cell Sampling

Virus detection protocols can be implemented on samples from any portion of the body, including samples from pre-blastocyst stages, embryonic tissues, perinatal material, cadavers or forensic sources. Preferably they are from cervicovaginal areas such as the cervix and vagina but can also be from cutaneous sources. Preferably they are from the cervical transformation zone. The samples can be collected using the CervexBrush, Therapak Corp, Irwindale, Calif., USA; Digene Cervical sampler cervical brush, Digene Corp. Gaithersburg, Md., USA; a plastic spatula/brush combination, Cooper Instruments, Hollywood, Fla., USA; or using dacron swabs or any suitable material for obtaining samples from the ano-genital area in both male and female patients or by any standard biopsy procedure such as a needle biopsy. The samples can be placed in various media, such as PreserveCyte, Cytyc Corp. MA, USA or AutoCyte PREP from TriPath Imaging Burlington, N.C., USA. Preferably, initial tests are conducted on Liquid based Cytology, but planar platforms such as paraffin sections and slides are also suitable.

Kits

The present invention can be implemented in the form of various kits, or combination of kits and instantiated in terms of manual, semi automated or fully robotic platforms. In a preferred form, the MethyEasy™ or HighThroughput MethylEasy™ kits (Human Genetic Signatures Pty Ltd, Australia) allow conversion of nucleic acids in 96 or 384 plates using a robotic platform such as EpMotion.

Human Papilloma Virus (HPV)

Mature human papilloma virus DNA is encapsulated within an icosahedral capsid coat consisting of two virally encoded proteins. The double stranded circular DNA genome is 7904 base pairs in length for HPV16, but among the common medium-risk types varies from 7808 base pairs of HPV51 to 7942 base pairs of HPV52. The regions of the viral genome are presented below in the order in which they occur on the circular molecule. The virus has a non-coding region termed URR followed by number of coding regions denoted, E6, E7, E1, E2, E4, E5, L2 and L1. Some viral types may lack a functional E5 region. The E4 region produces multiple protein products which cause disturbances of the cytoplasmic keratin network, leading to a cytoplasmic 'halo effect" termed koilocytosis. The different HPV types are epitheliotopic and after infection can lead to koilocytosis, dyskeratosis, multinucleation, abnormalities such as nuclear enlargement and low grade squamous intraepithelial lesions (SILs), all of these changes applying only to the cervix. Viral infection and chromosome abnormalities can be correlated in cervical carcinoma, but the multiparametric changes observed in neoplastic lesions, and their association with viral infection, viral gene expression, viral integration, cellular differentiation and genomic abnormalities is very poorly understood (1998, Southern, S. A. et al., Sex Transm Inf., 74, 101-109). It is for this reason that detection of different viral types and their differing effects in different genetic backgrounds is of such critical importance.

Additionally, although the designation of HPV types into cutaneous and mucosal categories and into high-, medium- and low-risk categories is accepted in the prior art, these categories exhibit some fraying and overlap even between the cutaneous and mucosal subcategories of HPV. For example HPV7 has been associated with cutaneous warts as well as oral lesions. HPV26 has been isolated in the context of generalized verrucosis as well as anogenital lesions. Furthermore, although HPV6 and HPV11 have been classified as low-risk types, they have been isolated from Buschke-Lowenstein tumors as well as laryngeal and vulval carcinomas and condylomata acuminate, (1986, Boshart, M. et al., J. Virology, 58, 963-966; 1992, Rubben, A., et al., J Gen Virol., 73, 3147-3153).

Viral integration into the host genome leads to linearization between the E1 and L1 gene regions with retention of the URR, E6 and E7 regions, but with deletion of gene regions such as E1, L1 and L2 and inactivation or deletion of E2. The E6 and E7 regions are generally retained in cervical carcinoma whereas E2 protein expression is absent. E2 damage has been associated with poor prognosis and shortened survival.

Patient Samples

Cell samples were collected by family physicians from the surface of the uterine cervix using a cervix sampling device supplied by Cytyc Corporation USA. The patients had given consent for the sample to be taken as part of a routine cancer screening program or as a monitoring test for previous cervical disease. The physicians transferred the cells from the collection device to a methanol/water solution for preservation of the cells and transport to the laboratory for testing. The cell sample was assessed for changes due to pre-cancer or viral infections using routine morphological preparations. A separate aliquot of the cell sample was used for DNA testing as outlined in this specification.

Extraction of DNA

Viral DNA can be obtained from and suitable source. Examples include, but not limited to, cell cultures, broth cultures, environmental samples, clinical samples, bodily fluids, liquid samples, solid samples such as tissue. Viral DNA from samples can be obtained by standard procedures. An example of a suitable extraction for paraffin fixed material is as follows. The sample of interest is placed in 400 µl of 7 M Guanidinium hydrochloride, 5 mM EDTA, 100 mM Tris/HCl pH 6.4, 1% Triton-X-100, 50 mM Proteinase K (Sigma), 100 µg/ml yeast tRNA. The sample is thoroughly homogenised with disposable 1.5 ml pestle and left for 48 hours at 60° C. After incubation the sample is subjected to five freeze/thaw cycles of dry ice for 5 minutes/95° C. for 5 minutes. The sample is then vortexed and spun in a microfuge for 2 minutes to pellet the cell debris. The supernatant is removed into a clean tube, diluted to reduce the salt concentration then phenol:chloroform extracted, ethanol precipitated and resuspended in 50 µl of 10 mM Tris/0.1 mM EDTA.

Surprisingly, it has been found by the present inventors that there is no need to separate the viral DNA from other sources of nucleic acids. The treatment step can be used for an vast mixture of different DNA types and yet a viral-specific nucleic acid can be still identified by the present invention. It is estimated that the limits of detection in a complex DNA mixtures are that of the limits of standard PCR detection which can be down to a single copy of a target viral nucleic acid molecule.

High Throughput HPV Assay

The present invention can be used step by step in a high throughput manner using a 96 well plate in which many samples are simultaneously tested for HPV. This is illustrated by instructions for a potential commercial kit as follows.

Contents of an HPV High Throughput DNA Bisulphite Modification Kit

| Component Name | Contents |
|---|---|
| Lysis Buffer | 1 × 1023 ml |
| Proteinase K | 2 × 1 × 2 ml |
| Binding Buffer | 1 × 35 ml |

-continued

| Component Name | Contents |
|---|---|
| Reagent 1 | 1 × 20.8 ml |
| Reagent 2 | 1 × 8 g |
| Elution bufferReagent 3 | 1 × 725 ml |
| Reagent 4 | 1 × 7 ml |
| Control Sample 1 | 1 × 40 µl |
| Control Sample 2 | 1 × 1620 µl |
| Control Primers 3A & 3B | 2 × 40 µl |
| Purification platePlate 1: Incubation plate | 1 × 96 well |
| WashPlate 2: Conversion plate | 1 × 96 well |
| ElutionPlate 3: Purification plate | 1 × 96 well |
| Base sealing mat Plate 4: Wash plate | 1 × mat 96 well |
| Sealing filmPlate 5: Elution plate | 41 × film 96 well |
| Sealing caps | 36 × 8 cap strips |
| Plate 6: High Risk HPV primersplate | 2 × 220 µl 96 well |
| Carrier DNAPlate 7: HPV Typing Plate | 18 × 100 µl 96 well |
| HPV TypingPlate 8: Control Plate | 82 × 96 well |

NB. Individual High-Risk Typing primers sets are available from Human Genetic Signatures (enquire at <hpv@geneticsignatures.com>)

Note:
Control Samples/Primers 1, 2, 3A and 3B should be stored at -20° C. upon receipt.

Materials and Equipment Required (Not Supplied)
Either a vacuum manifold or a centrifuge is used as follows:

A vacuum manifold for 96 well plates with a pump to apply at least −10 in Hg (4.9 psi) pressure. (In-house testing was carried out using the Biorad Aurum Manifold but other manifolds may be adapted for use.)

or

A centrifuge with a rotor compatible with a high clearance 96 well format plate. (In-house testing was carried out using an Eppendorf 5810).

Heated lid PCR Thermal Cycler compatible for 96 well format 0.2 ml low profile plates Heated lid PCR Thermal Cycler compatible for 384 well format (for HPV typing)

80% isopropanol (molecular biology grade)

Water (molecular biology grade)

NaOH pellets (Analytical Grade)

2×PCR master-mix (Promega Cat# M7505 1000rxn)

E-Gel System Mother E-Base™ device (Invitrogen EB-M03)

E-gels 96 High-Throughput 2% Agarose (Invitrogen Cat# G7008-02)

E-gel Low range marker (Invitrogen Cat#12373031)

Reagent reservoirs×5

Standard laboratory Equipment (Not Supplied)

Multi-channel pipette, up to 1 ml volume (200 µl-1000 µl)

Multi-channel pipette, up to 200 µL volume (20 µl-200 µl)

Multi-channel pipette, up to 10 µL volume (1 µl-10 µl)

Lint-free tissue

Timer

Aerosol barrier tips (10 µl-1000 µl)

Transilluminator

Gel Documentation system

Gilson P1000

Gilson P200

Gilson P20

Methods

If using HPV High Throughput DNA Bisulphite Modification Kit for the first time, it is highly recommended that the detailed methodology in the User Guide be read before carrying out the bisulphite conversion method.

Using the HPV High Throughput DNA Bisulphite Modification Kit eliminates the need for pre-digestion of genomic DNA prior to conversion.

This kit is optimized for starting DNA concentrations from 1 ng up to 4 µg of genomic DNA.

Sample Preparation

Combine the total volume of Reagent 1 to the Reagent 2 bottle and mix by gentle inversion. Place combined reagents at 72° C. for 10 minutes or until fully dissolved. Note: Once mixed Reagents 1 and 2 are stable for up to 1 month at 4° C. in the dark. All reagents are stable at room temperature for 1 year from the date of manufacture.

Place Binding Buffer in oven or incubator at 72° C. up to 1 hr before beginning the protocol.

Make a fresh 0.3M NaOH solution each time (eg. 0.6 g NaOH in 50.0 ml water).

Place the purification plate on top of the wash plate.

Add 5 µL of Control Sample 1 to 495 µL of water (molecular biology grade) and treat in parallel with the test samples. Control Sample 1 contains an unconverted HPV template that acts as a process control, and as a sensitivity control. This should be placed into well H10.

Always perform a "No DNA Control" where 500 µL of water is treated with the rest of the test samples, This should be placed into well H11.

Shake the Liquid Based Sample (PreservCyt®) vial vigorously by hand to resuspend any sedimented cells and ensure the sample is well mixed.

Transfer 300 µl of the resuspended cells to the appropriate wells in the purification plate/wash plate combo (Do not use wells H10, H11 or H12). Make detailed records of which well the samples were placed into.

Protocol

Centrifuge the purification plate/wash plate combo at 2000×rcf for 1 minute and discard the flow through. NB do not discard the wash plate.

Seal the spouts of the purification plate with the base-sealing mat, making sure all spouts are well sealed. Be sure to align the cut corner of the sealing mat with the cut corner of the purification plate at all times.

Add 2 ml of Proteinase K to lysis buffer and mix by inversion.

Add 100 µl of lysis buffer to each well of the purification plate (use a 12-channel pipette).

Take 10.5 ml of Binding Buffer to a new tube and add 100 µl Carrier DNA. Mix by inversion and add 100 µl of binding buffer to each well of the purification plate (use a 12-channel pipette) then seal the top of the purification plate with the plate sealing film provided.

Incubate at 55° C. for 60 minutes.

Carefully remove the base-sealing mat from the purification plate and quickly place the purification plate on top of the wash plate. Remove the sealing film from the purification plate then centrifuge at 2000×rcf for 1 minute and discard the flow through. NB Do not discard the wash plate.

Replace the base-sealing mat onto the purification plate.

Add 50 µl of fresh 0.3M NaOH solution to each well of the Conversion plate and seal the top of the purification plate with a fresh sealing film (provided).

Incubate at 55° C. for 15 minutes.

Remove the sealing film and add 220 µl of the combined Reagent 1 and Reagent 2 into each well of the Conversion plate, using a multi-channel pipette and seal the top of the purification plate with a fresh sealing film (provided).

Incubate the Conversion plate at 55° C. for 3 hours.

Following incubation remove the sealing film and add 240 µl of Binding buffer (Refer to Important Protocol Preparation) to each well of the Conversion plate, and mix by pipetting, and seal the top of the purification plate with a fresh sealing film (provided).

Carefully remove the base-sealing mat from the purification plate and quickly place the purification plate on top of the wash plate.

Remove the sealing film and centrifuge at 2000×rcf for 1 minute and discard the flow through.

Add 500 µl of 80% isopropanol to each well and centrifuge at 2000×rcf for 1 minute at room temperature.

Remove the Wash plate, discard the flow-through then replace and centrifuge at 2,000×rcf for 1 minute at room temperature.

Discard the Wash plate and place the Purification plate on top of the Elution plate ensuring the tips of the Purification plate are correctly aligned into the Elution plate. Stand plates at room temperature for 5 minutes.

Add 30 µl of Elution Buffer to each sample well of the Purification plate using a multi-channel pipette, placing the pipette tip close to the membrane surface without touching it.

Incubate at room temperature/1 minute.

Repeat above step once more to bring total elution volume to 60 µl

Centrifuge the Purification plate/Elution plate combination at 1000×rcf at room temperature/1 minute.

Remove the Elution plate and seal with the sealing caps provided.

Incubate the plate in a heated lid PCR machine at 95° C./30 minutes in a heated lid thermo-cycler. Spin briefly before removing caps.

Shake the Liquid Based Sample (PreservCyt®) vial vigorously by hand to resuspend any sedimented cells and ensure the solution is homogeneous.

Transfer 4 ml of the resuspended cells to a 15 ml Costar centrifuge tube. If there is less than 4 ml of media transfer all the material to a 15 ml Costar centrifuge tube and make the volume to 4 ml with sterile distilled water. A minimum volume of 1 ml sample is required for accurate testing.

Centrifuge the tubes in a swing-out bucket rotor at 3000× g/15 minutes.

Carefully decant and discard the supernatant without disturbing the pelleted cellular material.

Resuspend the pelleted cells in 200 µl of lysis buffer and mix well until the solution is homogeneous.

Add 20 µl of Proteinase K and incubate to each well of the incubation plate.

Transfer 80 µl of the sample to the Incubation plate (Plate 1) cover with sealing caps and incubate at 55° C./1 hour.

Protocol Preparation

Combine the total volume of Reagent 1 to the Reagent 2 bottle and mix by gentle inversion. Note: Once mixed Reagents 1 and 2 are stable for up to 1 month at 4° C. in the dark. Reagents 1, 2, 3 and 4 are stable at room temperature for 1 year from the date of manufacture.

Make a fresh NaOH solution each time (eg. 1 g NaOH in 8.3 ml water) and add 5 µl to each well of the Conversion plate (Plate 2).

Add 5 µl of Control Sample 1 to 15 µl of water (molecular biology grade) and treat in parallel with the test samples.

Transfer 20 µl of the cell lysate to the Conversion plate (Plate 2) and mix gently.

Seal the Conversion plate (Plate 2) with the sealing film provided and incubate in an oven at 37° C./15 minutes. After incubation, centrifuge the plate briefly before removing the film to precipitate any condensation on the film.

Seal the Incubation plate (Plate 1) with sealing caps provided and store at −20° C.

Ensure that Reagent 3 has not formed a solid precipitate. If so, warm the solution (not higher than 80° C.) and mix.

Centrifugation Protocol

Add 220 µl of the combined Reagent 1 and Reagent 2 into each well of the Conversion plate (Plate 2), using a multi-channel pipette then mix by gentle pipetting and seal the plate with the 8 strip sealing caps provided.

Incubate the Conversion plate (Plate 2) in an oven at 55° C./3 hours.

Bisulphite treatment can be carried out in as little as one hour, however, reducing incubation time can result in regional non-conversion within the amplicon. Incubation times of less than 3 hours are therefore not recommended.

Following incubation add 240 µl of Reagent 3 (Refer to Important Protocol Preparation) to each well of the Conversion plate (Plate 2).

Place the Purification plate (Plate 3) on top of the Wash plate (Plate 4).

Transfer the samples from the Conversion plate (Plate 2) to the corresponding wells of the Purification plate (Plate 3) and cover with the sealing film provided.

Place the Purification plate (Plate 3)/Wash plate (Plate 4) combination into the centrifuge and spin at 1,000 rcf at room temperature 14-5 minutes.

Discard the flow-through from the Wash plate (Plate 4) then replace it under the Purification plate (Plate 3). Add 0.8 ml of 80% isopropanol (molecular biology grade) to each well of the Purification plate (Plate 3).

Centrifuge at 1,000 rcf at room temperature/1 minute.

Remove the Wash plate (Plate 4), discard the flow-through then replace and centrifuge at 1,000 rcf/2 minutes at room temperature.

Place the Purification plate (Plate 3) on top of the Elution plate (Plate 5) ensuring the tips of the Purification plate (Plate 3) are positioned within the appropriate wells of the Elution plate (Plate 5).

Add 50 µl of Reagent 4 to each sample well of the Purification plate (Plate 3) using a multi-channel pipette, placing the pipette tip close to the membrane surface without touching it.

Incubate at room temperature/1-2 minute.

Centrifuge the Purification plate (Plate 3)/Elution plate (Plate 5) combination at 1,000 rcf at room temperature/1 minute.

Remove the Elution plate (Plate 5) and seal with the sealing caps provided.

Incubate the plate in a heated lid PCR machine at 95° C./30 minutes

The DNA samples are now converted and ready for PCR amplification. After incubation centrifuge the plate briefly to remove any condensation from the sealing caps.

Internal Control PCR Reaction

Genomic DNA and control PCR primers have been provided to allow for easy troubleshooting. Control Samples 1 (purple) and 2 (green) are provided as process controls. Control Sample 1 is untreated DNA with sufficient material provided for 8 conversion reactions. Control Sample 2 is bisulphite treated DNA with sufficient material provided for 20 PCR amplifications. Control Primers 3A (yellow) and 3B (red) are PCR primers and may be used to check the integrity of the recovered DNA (sufficient for 20 PCR amplifications provided).

'Nested' PCR primers are used to further improve the sensitivity of the detection that is achieved with HPV High Throughput DNA Bisulphite Modification Kit. The control primers are conventional bisulphite PCR primers and have been optimised for two rounds of PCR amplification. The use of these PCR primers for single round PCR is not recommended as in most cases no visible amplicon band will be seen following agarose gel electrophoresis.

Note: This protocol is based on the use of a heated-lid thermal cycler. If a heated-lid thermal cycler is unavailable, overlay reactions with mineral oil.

Control Reactions:

Control Sample 1 (purple) contains untreated HPV genomic DNA (50 ng/µl)

Control Sample 2 (green) contains bisulphite treated HPV human DNA (20 ng/µl)

Control Primers 3A (yellow) contains First round PCR primers

Control Primers 3B (red) contains Second round PCR primers

Control PCR

Control Primers 3A (First round PCR primers) and Control Primers 3B (Second round PCR primers) are validated 'nested' primers with sufficient volume supplied for up to 20 control PCR reactions. These primer samples have been supplied to facilitate the trouble-shooting process if required, and may also be used to assess the quality of your modified DNA.

Note: The Second round PCR Reactions may be prepared in parallel with the First round PCR Reactions and frozen until required.

High-Risk PCR Amplification

First Round Amplification

For each reaction, add 12.5 µl of PCR Master Mix (for example, Promega Master Mix) and 9.5 µl water (molecular biology grade) in the High-Risk PCR plate provided. If you are setting up 96 samples combine 1.25 ml Master mix, 850 µl of water and 200 µl of primer mix in an appropriate tube and mix well. Then using a multi channel pipette add 23 of the reaction mix to each well in the High-Risk HPV plate (Plate 6) provided.

Add 2 µl of Control Primers 3A to the appropriate well to control well H10 and H11.

Add 2 µl of the required modified DNA from the Elution plate (Plate 5) to the High-Risk HPV plate (Plate 6) provided and 2 µl of Control Sample 2 to well H11 then store the remainder at −20° C. for subsequent HPV typing (see below for High-Risk plate lay-out).

Run the following PCR program.

| | |
|---|---|
| 95° C./3 min | 1 cycle |
| 95° C./1 min | 30 cycles |
| 42° C./2 min | |
| 60° C./2 min | |
| 65° C./10 min | 1 cycle |

Second Round Amplification

Add 2 µl of the first round amplified DNA to second round mixes, prepared exactly the same as for the first round amplifications.

Run the following PCR program

| | |
|---|---|
| 95° C./3 min | 1 cycle |
| 95° C./1 min | 30 cycles |
| 42° C./2 min | |
| 60° C./2 min | |
| 60° C./10 min | 1 cycle |

Electrophoresis

Remove the 96 well 2% E-gel from the foil wrapper and remove the red 96 well comb.

Add 10 µl of sterile water to each well of the gel using a multi-channel pipette.

Add 10 µl of DNA marker to the marker wells.

Transfer 10 µl of amplified product to each well of the E-gel using a multichannel pipette.

Set the E-base for 5-7 minutes and press pwr/prg.

Record the results using an UV transilluminator and gel documentation software.

HPV Typing

First Round Amplification

The High-Risk Typing plate (Plate 8) contains strain specific primers directed against the following high-risk HPV types: 16, 18, 31, 33, 35, 39, 45, 51, 52, 56, 58, 59 and 68.

There is sufficient DNA remaining in the Elution plate (Plate 5) to type each sample for all high-risk strains.

Remove the Elution plate (Plate 5) from the −20° C. freezer.

Any samples positive by the high-risk universal amplification can now be typed using the strain specific primers (see below for typing plate set-up)

For each reaction, add 12.5 µl of PCR Master Mix (for example, Promega Master Mix) and 8.5 µl water into each well of the PCR plate provided. If you have 6 samples to type add 1187.5 µl of Master Mix and 807.5 µl of water into an appropriate tube, mix well then add 21 µl to each well of the HPV Typing plate (Plate 7) as indicated below.

Add 2 µl of the appropriate primer set to each well as indicated below.

If the typing is being carried out in 384 well format and 24 samples are available for typing add 4.5 ml of Master Mix and 3.42 ml of water into an appropriate tube, mix well then add 21 µl to each well of the 384 well plate as indicated below. Then add 2 µl of the appropriate primer set to each well as indicated below.

Add 2 µl of High-Risk positive sample (from Elution plate, Plate 5) to the appropriate wells of the typing plate.

Set up sufficient tubes for each of your samples and a 'no template' (negative) control.

Run the following PCR program.

| | |
|---|---|
| 95° C./3 min | 1 cycle |
| 95° C./1 min | 30 cycles |
| 45° C./2 min | |
| 65° C./2 min | |
| 65° C./10 min | 1 cycle |

Second Round Amplification

Add 2 µl of the First round amplified DNA to Second round mixes, prepared exactly the same as for the First round amplifications.

Run the following PCR program

| | |
|---|---|
| 95° C./3 min | 1 cycle |
| 95° C./1 min | 30 cycles |
| 45° C./2 min | |
| 65° C./2 min | |
| 65° C./10 min | 1 cycle |

Electrophoresis

Remove the 96 well 2% E-gel from the foil wrapper and remove the red 96 well comb.

Add 10 µl of sterile water to each well of the gel using a multi-channel pipette.

Add 10 µl of DNA marker to the marker wells.

Transfer 10 µl of amplified product to each well of the E-gel using a multichannel pipette.

Set the E-base for 5-7 minutes and press run.

Record the results using an UV transilluminator and gel documentation software.

The sample has now been typed.

Troubleshooting

| PROBLEMS | POSSIBLE SOLUTIONS |
|---|---|
| No PCR product was found for any sample | PCR has failed - make sure all the components were added to the tube and that the PCR cycle was correct. Confirm that the polymerase is within its storage date and that it retains its activity. |
| No PCR product was found for any sample except for Control Sample 2 | Modification has failed - check that the NaOH solution was fresh and that combined Reagent # 1 and Reagent 2 was no older than 4 weeks. Make sure that all the steps in the modification and clean up protocols were followed. DNA was degraded during modification - check that all reagents and tubes used during the procedure were of molecular biology quality (ie DNase free). Modification was incomplete. Return the samples to 95° C. for a further 15 minutes. Sample DNA was degraded before modification- check that the DNA has been stored/handled correctly. |
| PCR products were present only in the control reactions | Check that the DNA concentration is not too dilute. Check that the PCR-grade water and not the template was added to the negative control. |
| PCR products were present in all the lanes including the 'no-template' (negative) control | Make sure that the PCR is being set up in a separate area with dedicated reagents and equipment to prevent cross contamination. |

Bisulfite-treated HPV DNA from sources, when amplified using genomically simplified primers, be they oligonucleotides or modified nucleic acids such as INAs provide an unsurpassed detection system for finding HPV of any type within a sample, be that sample from human clinical material or at another extreme from an environmental source. The present invention has been developed for a clinically relevant virus (HPV) believed to be causative for a human cancer.

The practical implications of the detection assay according to the present invention can be varied. While the principles described in detail above have been demonstrated using PCR for amplification, readouts can be engaged via any methodology known in the art. With the current emphasis on microarray detection systems, one would be able to detect a great diversity of HPV using genomically simplified DNA since the bisulfite treatment reduces the genomic complexity and hence allows for more types of HPV to be tested on microarrays with a smaller number of detectors (features).

In summary, the HGS genomically simplified primer methodology yields consistent data sets that has been correlated with the clinical phenotypes of a number of patients.

Bisulphite Treatment

An exemplary protocol for effective bisulphite treatment of nucleic acid is set out below. The protocol results in retaining substantially all DNA treated. This method is also referred to herein as the Human Genetic Signatures (HGS) method. It will be appreciated that the volumes or amounts of sample or reagents can be varied.

Preferred method for bisulphite treatment can be found in U.S. Ser. No. 10/428,310 or WO 2004/096825 (PCT/AU2004/000549) in the name of Human Genetic Signatures Pty Ltd, incorporated herein by reference.

To 2 μg of DNA, which can be pre-digested with suitable restriction enzymes if so desired, 2 μl (1/10 volume) of 3 M NaOH (6 g in 50 ml water, freshly made) was added in a final volume of 20 μl. This step denatures the double stranded DNA molecules into a single stranded form, since the bisulphite reagent preferably reacts with single stranded molecules. The mixture was incubated at 37° C. for 15 minutes. Incubation at temperatures above room temperature can be used to improve the efficiency of denaturation.

After the incubation, 208 μl 2 M Sodium Metabisulphite (7.6 g in 20 ml water with 416 ml 10 N NaOH; BDH AnalaR #10356.4D; freshly made) and 12 μl of 10 mM Quinol (0.055 g in 50 ml water, BDH AnalR #103122E; freshly made) were added in succession. Quinol is a reducing agent and helps to reduce oxidation of the reagents. Other reducing agents can also be used, for example, dithiothreitol (DTT), mercaptoethanol, quinone (hydroquinone), or other suitable reducing agents. The sample was overlaid with 200 μl of mineral oil. The overlaying of mineral oil prevents evaporation and oxidation of the reagents but is not essential. The sample was then incubated overnight at 55° C. Alternatively the samples can be cycled in a thermal cycler as follows: incubate for about 4 hours or overnight as follows: Step 1, 55° C./2 hr cycled in PCR machine; Step 2, 95° C./2 min. Step 1 can be performed at any temperature from about 37° C. to about 90° C. and can vary in length from 5 minutes to 8 hours. Step 2 can be performed at any temperature from about 70° C. to about 99° C. and can vary in length from about 1 second to 60 minutes, or longer.

After the treatment with Sodium Metabisulphite, the oil was removed, and 1 μl tRNA (20 mg/ml) or 2 μl glycogen were added if the DNA concentration was low. These additives are optional and can be used to improve the yield of DNA obtained by co-precitpitating with the target DNA especially when the DNA is present at low concentrations. The use of additives as carrier for more efficient precipitation of nucleic acids is generally desired when the amount nucleic acid is <0.5 μg.

An isopropanol cleanup treatment was performed as follows: 800 μl of water were added to the sample, mixed and then 1 ml isopropanol was added. The water or buffer reduces the concentration of the bisulphite salt in the reaction vessel to a level at which the salt will not precipitate along with the target nucleic acid of interest. The dilution is generally about 1/4 to 1/1000 so long as the salt concentration is diluted below a desired range, as disclosed herein.

The sample was mixed again and left at 4° C. for a minimum of 5 minutes. The sample was spun in a microfuge for 10-15 minutes and the pellet was washed 2× with 70% ETOH, vortexing each time. This washing treatment removes any residual salts that precipitated with the nucleic acids.

The pellet was allowed to dry and then resuspended in a suitable volume of T/E (10 mM Tris/0.1 mM EDTA) pH 7.0-12.5 such as 50 μl. Buffer at pH 10.5 has been found to be particularly effective. The sample was incubated at 37° C. to 95° C. for 1 min to 96 hr, as needed to suspend the nucleic acids.

Amplification

PCR amplifications were performed in 25 μl reaction mixtures containing 2 μl of bisulphite-treated genomic DNA, using the Promega PCR master mix, 6 ng/μl of each of the primers. Strand-specific nested primers are used for amplification. 1st round PCR amplifications were carried out using PCR primers 1 and 4 (see below). Following 1st round amplification, 1 μl of the amplified material was transferred to 2nd round PCR premixes containing PCR primers 2 and 3 and amplified as previously described. Samples of PCR products were amplified in a ThermoHybaid PX2 thermal cycler under the conditions: 1 cycle of 95° C. for 4 minutes, followed by 30 cycles of 95° C. for 1 minute, 50° C. for 2 minutes and 72° C. for 2 minutes; 1 cycle of 72° C. for 10 minutes.

A representation of the fully nested PCR approach is shown below:

Multiplex Amplification

One μl of bisulphite treated DNA is added to the following components in a 25 μl 20 reaction volume, xl Qiagen multiplex master mix, 5-100 ng of each 1st round INA or oligonucleotide primer 1.5-4.0 mM MgSO4, 400 μM of each dNTP and 0.5-2 units of the polymerase mixture. The components are then cycled in a hot lid thermal cycler as follows. Typically there can be up to 200 individual primer sequences in each amplification reaction:

Step 1; 94° C. 15 minute 1 cycle
Step 2; 94° C. 1 minute; 50° C. 3 minutes 35 cycles; 68° C. 3 minutes.
Step 3 68° C. 10 minutes 1 cycle A second round amplification is then performed on a 1 μl aliquot of the first round amplification that is transferred to a second round reaction tube containing the enzyme reaction mix and appropriate second round primers. Cycling is then performed as above.

HGS 'Complexity-Reduced' Primers and Probes

Any suitable PCR primers or probes can be used for the present invention as well as specially designed primers and probes for non-PCR amplification involving isothermal amplification methodologies. A primer or probe typically has a complementary sequence to a sequence which will be amplified. Primers or probes are typically oligonucleotides but can be nucleotide analogues such as INAs. Primers to the 'top' and 'bottom' strands will differ in sequence.

Probes and Primers

A probe or primer may be any suitable nucleic acid molecule or nucleic acid analogue. Examples include, but not limited to, DNA, RNA, locked nucleic acid (LNA), peptide nucleic acid (PNA), MNA, altritol nucleic acid (ANA), hexitol nucleic acid (HNA), intercalating nucleic acid (INA), cyclohexanyl nucleic acid (CNA) and mixtures thereof and hybrids thereof, as well as phosphorous atom modifications thereof, such as but not limited to phosphorothioates, methyl phospholates, phosphoramidites, phosphorodithiates, phosphoroselenoates, phosphotriesters and phosphoboranoates. Non-naturally occurring nucleotides include, but not limited to the nucleotides comprised within DNA, RNA, PNA, INA, HNA, MNA, ANA, LNA, CNA, CeNA, TNA, (2'-NH)-TNA, (3'-NH)-TNA, α-L-Ribo-LNA, α-L-Xylo-LNA, β-D-Xylo-LNA, α-D-Ribo-LNA, [3.2.1]-LNA, Bicyclo-DNA, 6-Amino-Bicyclo-DNA, 5-epi-Bicyclo-DNA, a-Bicyclo-DNA, Tricyclo-DNA, Bicyclo[4.3.0]-DNA, Bicyclo[3.2.1]-DNA, Bicyclo[4.3.0]amide-DNA, β-D-Ribopyranosyl-NA, α-L-Lyxopyranosyl-NA, 2'-R-RNA, a-L-RNA or a-D-RNA, β-D-RNA. In addition non-phosphorous containing compounds may be used for linking to nucleotides such as but not limited to methyliminomethyl, formacetate, thioformacetate and linking groups comprising amides. In particular nucleic acids and nucleic acid analogues may comprise one or more intercalator pseudonucleotides.

The probes or primers can be DNA or DNA oligonucleotides containing one or more internal IPNs forming INA.

Detection Methods

Numerous possible detection systems exist to determine the status of the desired sample. Detection systems include, but not limited to:

I. Hybridization of appropriately labelled DNA to a microarray type device which could select for 10->200,000 individual components. The arrays could be composed of either INAs, PNAs or nucleotide or modified nucleotides arrays onto any suitable solid surface such as glass, plastic, mica, nylon, bead, magnetic bead, fluorescent bead or membrane;

II. Southern blot type detection systems;

III. Standard PCR detection systems such as agarose gel, fluorescent read outs such as Genescan analysis. Sandwich hybridisation assays, DNA staining reagents such as ethidium bromide, Sybr green, antibody detection, ELISA plate reader type devices, fluorimeter devices; IV. Real-Time PCR quantitation of specific or multiple genomic amplified fragments or any variation on that;

V. Any of the detection systems outlined in the WO 2004/065625 such as fluorescent beads, enzyme conjugates, radioactive beads and the like;

VI. Any other detection system utilizing an amplification step such as ligase chain reaction or Isothermal DNA amplification technologies such as Strand Displacement Amplification (SDA).

VII. Biosensor technology such as U.S. Pat. No. 6,426,231 and U.S. Pat. No. 6,916,665 in the name of The Texas A&M University System, U.S. Pat. No. 6,824,659 in the name of University of Massachusetts, incorporated herein by reference, would be suitable for the present invention.

Intercalating Nucleic Acids

Intercalating nucleic acids (INA) are non-naturally occurring polynucleotides which can hybridize to nucleic acids (DNA and RNA) with sequence specificity. INA are candidates as alternatives/substitutes to nucleic acid probes and primers in probe-, or primer-based, hybridization assays because they exhibit several desirable properties. INAs are polymers which hybridize to nucleic acids to form hybrids which are more thermodynamically stable than a corresponding naturally occurring nucleic acid/nucleic acid complex. They are not substrates for the enzymes which are known to degrade peptides or nucleic acids. Therefore, INAs should be more stable in biological samples, as well as having a longer shelf-life than naturally occurring nucleic acid fragments. Unlike nucleic acid hybridization which is very dependent on ionic strength, the hybridization of an INA with a nucleic acid is fairly independent of ionic strength and is favoured at low ionic strength under conditions which strongly disfavour the hybridization of naturally occurring nucleic acid to nucleic acid. The binding strength of INA is dependent on the number of intercalating groups engineered into the molecule as well as the usual interactions from hydrogen bonding between bases stacked in a specific fashion in a double stranded structure. Sequence discrimination is more efficient for INA recognizing DNA than for DNA recognizing DNA.

Preferably, the INA is the phosphoramidite of (S)-1-O-(4, 4'-dimethoxytriphenylmethyl)-3-O-(1-pyrenylmethyl)-glycerol.

INAs are synthesized by adaptation of standard oligonucleotide synthesis procedures in a format which is commercially available. Full definition of INAs and their synthesis can be found in WO 03/051901, WO 03/052132, WO 03/052133 and WO 03/052134 (Human Genetic Signatures Pty Ltd) incorporated herein by reference.

There are indeed many differences between INA probes and primers and standard nucleic acid probes and primers. These differences can be conveniently broken down into biological, structural, and physico-chemical differences. As discussed above and below, these biological, structural, and physico-chemical differences may lead to unpredictable results when attempting to use INA probes and primers in applications were nucleic acids have typically been employed. This non-equivalency of differing compositions is often observed in the chemical arts.

With regard to biological differences, nucleic acids are biological materials that play a central role in the life of living species as agents of genetic transmission and expression. Their in vivo properties are fairly well understood. INA, however, is a recently developed totally artificial molecule, conceived in the minds of chemists and made using synthetic organic chemistry. It has no known biological function.

Structurally, INAs also differ dramatically from nucleic acids. Although both can employ common nucleobases (A, C, G, T, and U), the composition of these molecules is structurally diverse. The backbones of RNA, DNA and INA are composed of repeating phosphodiester ribose and 2-deoxyribose units. INA differs from DNA or RNA in having one or more large flat molecules attached via a linker molecule(s) to the polymer. The flat molecules intercalate between bases in the complementary DNA stand opposite the INA in a double stranded structure.

The physico/chemical differences between INA and DNA or RNA are also substantial. INA binds to complementary DNA more rapidly than nucleic acid probes or primers bind to the same target sequence. Unlike DNA or RNA fragments, INA bind poorly to RNA unless the intercalating groups are located in terminal positions. Because of the strong interactions between the intercalating groups and bases on the complementary DNA strand, the stability of the INA/DNA complex is higher than that of an analogous DNA/DNA or RNA/DNA complex.

Unlike other nucleic acids such as DNA or RNA fragments or PNA, INAs do not exhibit self aggregation or binding properties.

In summary, as INAs hybridize to nucleic acids with sequence specificity, INAs are useful candidates for developing probe-, or primer-based assays and are particularly adapted for kits and screening assays. INA probes and primers, however, are not the equivalent of nucleic acid probes and primers. Consequently, any method, kits or compositions which could improve the specificity, sensitivity and reliability of probe-, or primer-based assays would be useful in the detection, analysis and quantitation of DNA containing samples. INAs have the necessary properties for this purpose.

HPV and Cancer Genomic Markers

Using clinical samples and cell lines, the present inventors have looked at methylation patterns in regulatory regions of nearly 400 genes and have found over 60 genomic markers that have methylation changes when in a cancerous state together with the presence of HPV. Examples include, but not limited to, one or more of the following genomic regions within, or near to, the transcription units, (genes) denoted CD14, ENDRB, HIC, RARB1, PGR, SFRS8, TMSB10, ABCG2, MFNG, LAMR1, RAGE, ABL1, CRBP, GPR37, HRK, RARA, SYK, ECE1, MME, TEM, NF2, XIAPHSX11, RARRES1, FLI1, HTLF, LDHB, RB1, TGD, CDK4, MMP14, RAB32, BARD1, NF1, LIM2, MMP2, DAB2, BMP6, CDKN1C, DAB2IP, LMNB1, MMP28, HAI2, SOCS1, HIC2, MSH6, RIN2, HMGA1, JUN, S100P*, SRF, VDR, DKK3, KRAS2, PLAU, TNFRSF10B, CDH1, MAC30, DDB2, PAX6, AXL, EIF4A2, SLIT2, RECK, TERC, GATA5, STAT1.

Disease States

The present inventors have used HPV and methylation of selected human genomic regions in cervical cancer as an example of demonstrating the present invention. It will be appreciated that other states such as various forms of dementia, (Alzheimers), may have an infectious component such as Herpes simplex virus type 1, (2004, Neurobiology of Aging, 25, 619-627; Itzhaki, R. F., et al.); the clinical progression and viral load associated with coronavirus-associated SARS pneumonia, (2003, The Lancet, 361, 1767-1772, Peiris, J. S. M. m et al.,); human immunodeficiency virus HIV, and immune system compromise and several viral-based hemorraghic fevers, (2004, Nature Medicine, 10, 570-576, Weiss, R. A., et al.,); the viruses of the family Paramyxoviridae which include Nipah virus, parainfluenza and Mumps and are associated with various respiratory illnesses, mumps, meningitis, pancreatitis, encephalitis and measles. Nipah virus was only recognised first in 1999 and it causes fatal encephalitis in 70% of infected patients and has an extremely broad host range including humans, dogs, cats, pigs, horses, hamsters, bats and guinea pigs. It is a critical threat to global health and economies (2005, Nature, 436, 401-405; Negrete, O. A., et al,); viruses of the Flaviviridae, which include Dengue, Yellow Fever, Hepatitis C and G and are associated with encephalitis, hepatitis and shock syndrome. Hep C for example, is a major cause of chronic liver disease with over 170 million individuals infected worldwide and with no available vaccine, (2005, Science, 309, 623-626; Lindenbach, B. D., et al,); and finally viruses of the family Herpesviridae, which include human herpesvirus 1 through 8. These viruses can give rise to oral infections, ulceration of the cornea, genital tract infections, meningitis, chickenpox, pneumonia, shingles, cytomegaloviral mononucleosis and encephalitis. Human Cytomegalovirus causes severe and fatal diseases in immunocompromised individuals, including organ transplant individuals, (2003, Nature, 424, 456-461; Wang, X., et al) would also be candidates for the present invention in humans as well as various animals as progression of the Health State can be monitored by a combination of viral presence and methylation state of the DNA of the host. Similar examples are available for plant viruses and viroids.

EXAMPLES

HPV

To demonstrate the present invention, HPV and cervical cancer will be used in the following examples. It will be appreciated that other viruses and disease states, as outlined above can also be assayed by the present invention.

To reiterate the foundations on which the present inventors have based their bioinformatic analyses in silico, the standard HPV type utilized herein for reference purposes is HPV16 of the Family Papovaviridae, Genus Papillomavirus, originally designated as such by the International Committee on Taxonomy of Viruses, ICTV, (1993, Van Rast, M. A., et al., Papillomavirus Rep, 4, 61-65; see also, 1998 Southern, S. A. and Herrington, C. S. Sex. Transm. Inf. 74, 101-109), although taxonomic upgrades to the Papillomaviridae are sometimes used interchangeably in the prior art. To avoid ambiguity, the present inventors used the fully sequenced 7904 base pair genome of HPV16 as a standard comparator (National Center for Biotechnology Information, NCBI locus NC_001526; version NC_001526.1; GI:9627100; references, Medline, 91162763 and 85246220; PubMed 1848319 and 2990099).

In addition, the present inventors used the fully sequenced genomes of the so called high-risk HPV types 16, 18, 45 and 56 with NCBI accession numbers of NC-001526, NC-001357, NC-001590 and NC-001594 respectively.

The present inventors used the fully sequenced genomes of the so called medium risk HPV types 30, 31, 33, 35, 39, 51, 52, 58 and 66 with NCBI accession numbers of NC-001585, NC-001527, NC-001528, NC-001529, NC-001535, NC-001533, NC-001592, NC-001443 and NC-001695 respectively.

The present inventors used use the fully sequenced genomes of the so called low risk HPV types 6, 11, 42, 43, 44, 53, 54 and 55 with NCBI accession numbers of NC-000904, NC-001525, NC-001534, NC-005349, NC-001689, NC-001593, NC-001676 and NC-001692 respectively.

As the present inventors have demonstrated, the detection of human papilloma viral DNA in various clinical samples via conventional DNA tests is hampered by a number of technical, methodological and clinical problems. The present invention provides a solution to many of the difficulties encountered in the prior art, since the bisulphite conversion of HPV DNA reduces the complexity of the HPV derivative sequence pool. This complexity-reduction allows for a more efficient initial screening of the different HPV types within a sample and hence for a more appropriate and accurate interface with the clinical data.

Examples of the detection of HPV in a sample using methods developed by the applicant can be found in WO 2006/066353 (PCT/AU2005/001963) in the name of Human Genetic Signatures Pty Ltd, incorporated herein by reference.

FIG. 1 shows the results of testing various normal individuals, as well as those with High Grade Squamous Intraepithelial Lesions, and a cell line for the presence of HPV. The data provided complement the data of FIG. 1 from patients who have been tested for HPV as well as the methylation status of 400 human genomic regions.

TABLE 2

Expected fragment sizes in base pairs of amplified nucleic acid products generated from different HPV derivatives of the three major risk types.

HPV Risk Category PCR product band size (bp)

| High | Size | Medium | Size | Low | Size |
| --- | --- | --- | --- | --- | --- |
| HPV16 | 205 | HPV30 | 302 | HPV6 | 353 |
| HPV18 | 231 | HPV31 | 216 | HPV11 | 268 |
| HPV45 | 217 | HPV33 | 234 | HPV42 | 228 |
| HPV56 | 272 | HPV35 | 351 | HPV43 | 251 |
|  |  | HPV39 | 230 | HPV44 | 246 |

TABLE 2-continued

Expected fragment sizes in base pairs of amplified nucleic acid products generated from different HPV derivatives of the three major risk types.

HPV Risk Category PCR product band size (bp)

| High | Size | Medium | Size | Low | Size |
|---|---|---|---|---|---|
| | | HPV51 | 251 | HPV53 | 207 |
| | | HPV52 | 259 | HPV54 | 248 |
| | | HPV58 | 182 | HPV55 | 303 |
| | | HPV66 | 255 | | |

The Dual Presence of HPV and the Methylation Status of Various Human Genomic Regions The experiments were devised to demonstrate that the presence of HPV together with the methylation status of specific genomic regions is a more powerful prognostic indicator of health state than either characteristic alone. In this manner, a large number of genomic regions have been assayed for their methylation status in samples from individuals whose cervical cytology is normal; individuals whose cervical cytology is characteristic of High Grade Intraepithelial Lesions, and an individual whose cervical cytology is normal as regards cancerous indicators of cell morphology, but who is inferred to be positive for HPV on the basis of cytological characteristics.

FIG. 1A shows that a HeLa cell line, two patients exhibiting HSIL as determined by a pathologist, (denoted HSIL-1 and HSIL-2), and one patient with normal cervical morphology but with the presence of HPV inferred from the pathological phenotype (denoted HPV+Nor) were positive for the presence of HPV as determined by appropriate PCR amplification technology. Two patients with normal cervical morphology (denoted Normal-1 and Normal-2) were molecularly negative for the presence of High-Risk HPV types.

Figure 1B:
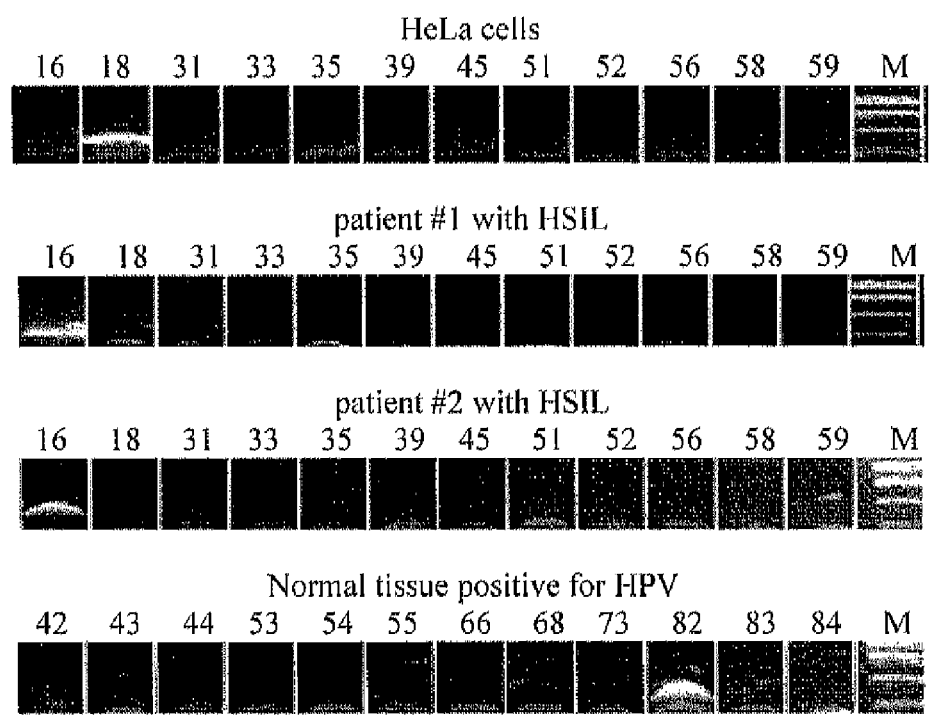

FIG. 1B shows the presence of a band, (an amplicon), in the HeLa cell line, (panel 1), and this contains HPV18 type DNA sequences. The two HSIL samples, (panels 2 and #), contain HPV16 as assayed molecularly. The cervical tissue which was determined to be morphologically normal by a pathologist, but some cells of which had characteristic cytoplasmic features that were indicative of HPV infection, was found to be positive for HPV type 82, (panel 4).

These clinical samples were then tested at each genomic locus for the presence of methylation, (denoted pos), or non-methylation, (denoted neg). The crucial prognostic indicators are, for example, when patients with normal pathology have a non-methylated locus whereas patients with High grade Intraepitheial Lesions have methylation at the same region; in short, the associated gene region has been silenced in the progression to the cancerous state. (The converse of course applies. Individuals with normal cytology may have a locus that is methylated in a particular cell type, and that locus becomes unmethylated in the cancerous state).

Since methylation of a given genomic region varies with cell type, some genomic regions will of necessity be uninformative as regards progression to the cancerous state in that particular cell type. These regions will either be completely unmethylated in all samples, or completely methylated in all clinical samples.

Table 3A and 3B show the HPV status of a number of clinical samples, as well as that of a HeLa cell line, and the methylation status of 53 individual human genomic regions.

As can be seen from Tables 3A and 3B both the HeLa cervical cancer cell line and the High grade Squamous Interepithelial Lesions (HSIL) were positive for the presence of HPV DNA as determined molecularly. One non-cancerous cervical tissue sample, but with an HPV infection as inferred pathologically, (denoted HPV+Nor) was also found to be positive for the presence of HPV. The two normal cervical tissue samples from different individuals were found to be negative for the presence of HPV DNA sequences as determined molecularly.

Each of the above regions was PCR amplified and the resulting amplicons digested with appropriate restriction enzymes (and/or sequenced) to determine the methylation status of that particular genomic region (Tables 3A and 3B).

First, there are genomic regions that are uninformative as regards being prognostic indicators. These are unmethylated in all samples, (13 genomic regions ABCG2 to VHL), or methylated in all samples, (4 genomic regions, CD34, MAGEA2, MAGEA3 and MINT31). Of particular interest from the results in Tables 3A and 3B are genomic regions denoted CD14, ENDRB, HIC and RARB. All of these regions were methylated in the HeLa cervical cancer cell line and both HSIL samples. Interestingly, none of these regions was methylated in either the normal cervical tissues tested or in the non-cancerous cervical tissue sample infected with HPV.

Finally, 32 genomic regions ANAX7 through TNFRS10B, show variable methylation patterns between normal individuals and those with HSIL. This variation very likely reflects a mixture of the genetic background of individual patients and the differing stabilities of the methylation status at individual loci of the human genome.

The results indicate that although the presence of HPV has been detected in almost all HSIL and cervical cancers, the presence of HPV alone is not a reliable indicator of high grade abnormalities of the cervix. However, when the presence of HPV is linked with a change in the methylation profile of cervical DNA samples this gives a much better prognostic indicator of disease state.

TABLE 3A

| | HeLa | HSIL-1 | HSIL-2 | Norm-1 | Norm-2 | HPV +Nor |
|---|---|---|---|---|---|---|
| HPV Status | Pos | Pos | Pos | Neg | Neg | Pos |

TABLE 3B

| | Methylation | | | | | |
|---|---|---|---|---|---|---|
| Gene | HeLa | HSIL-1 | HSIL-2 | Norm-1 | Norm-2 | HPV +Nor |
| ABCG2 | Neg | Neg | Neg | Neg | Neg | Neg |
| ABO | Neg | Neg | Neg | Neg | Neg | Neg |
| CDKN1A | Neg | ND | Neg | Neg | Neg | Neg |
| EZH2-L | Neg | Neg | Neg | Neg | Neg | Neg |
| HPRT | Neg | Neg | Neg | Neg | Neg | ND |
| MGMT | Neg | Neg | Neg | Neg | Neg | Neg |
| MIF | Neg | Neg | Neg | Neg | Neg | Neg |
| P14 | Neg | Neg | Neg | Neg | Neg | Neg |
| PTGS2 | Neg | Neg | Neg | Neg | Neg | Neg |
| THRB | Neg | Neg | Neg | Neg | Neg | Neg |
| TIMP3 | Neg | Neg | Neg | Neg | Neg | Neg |
| TP53 | Neg | Neg | Neg | Neg | Neg | Neg |
| VHL | Neg | Neg | ND | Neg | Neg | Neg |
| CD14 | Pos | Pos | Pos | Neg | Neg | Neg |
| ENDRB | Pos | Pos | Pos | Neg | Neg | Neg |
| HIC | Pos | Pos | Pos | Neg | Neg | Neg |
| RARB1 | Pos | Pos | Pos | Neg | Neg | Neg |
| CD34 | Pos | Pos | Pos | Pos | Pos | Pos |
| MAGEA2 | Pos | Pos | Pos | Pos | Pos | Pos |
| MAGEA3 | Pos | Pos | Pos | Pos | Pos | Pos |
| MINT31 | Pos | Pos | Pos | Pos | Pos | Pos |
| ANAX7 | Neg | Neg | Neg | Neg | Neg | Pos |
| APC | Pos | Pos | Neg | Neg | Neg | Neg |
| APP | Pos | Neg | Pos | Pos | Neg | Pos |
| BRCA2 | Neg | Neg | Neg | Neg | Neg | Neg |
| CALCA | Pos | Neg | Neg | Neg | Neg | Neg |
| CCNA1 | Pos | Neg | Neg | Neg | Neg | ND |
| CDH13 | Pos | Pos | Pos | Pos | Neg | Neg |
| CDKN2Av2 | Pos | Neg | Pos | Pos | Pos | Pos |

TABLE 3B-continued

| Gene | | | | | | |
|---|---|---|---|---|---|---|
| CFTR | Pos | Neg | Neg | Neg | Neg | Neg |
| CXCL2 | Neg | Pos | Pos | Pos | Neg | Neg |
| DBCCR1 | Pos | Pos | Neg | Neg | Neg | Neg |
| DNAJB9 | Neg | Neg | Pos | Neg | Neg | Neg |
| EFNA4 | Neg | Pos | Pos | Pos | Pos | Pos |
| GP9 | Pos | ND | Neg | Pos | Pos | Pos |
| GSTP1 | Pos | Neg | Pos | Neg | Neg | Neg |
| GUS | Neg | Neg | Neg | Neg | Neg | Neg |
| HOXB5 | Pos | Neg | Neg | Neg | Neg | Neg |
| HOXD13 | Pos | ND | Neg | Neg | Neg | ND |
| LIM2 | Pos | Neg | Neg | Neg | Neg | Neg |
| MYB | Neg | Pos | Pos | Pos | Pos | Pos |
| MYOD1 | Pos | ND | Neg | Neg | Neg | Neg |
| N33 | Pos | Neg | Pos | Neg | Neg | Neg |
| NNAT | Pos | Neg | Neg | Pos | Neg | Neg |
| PSEN | Neg | Neg | Neg | Neg | Neg | Pos |
| RUNX3 | Pos | Neg | Neg | Neg | Neg | Neg |
| SCGB3A1 | Pos | Neg | Neg | Neg | Neg | Neg |
| SFN1 | Neg | Pos | Neg | Pos | Neg | Pos |
| SOD1 | Neg | Neg | Pos | Neg | Neg | Neg |
| SOX4 | Neg | Neg | Pos | Neg | Neg | Neg |
| SRF | Neg | Pos | Neg | Neg | Neg | Neg |
| TERT | Pos | Pos | ND | Neg | Pos | ND |
| TNFRS10B | Neg | Neg | Pos | Neg | Neg | Neg |

ND = not determined

In addition to methylation of genomic regions CD14, ENDRB, HIC and RARB the present inventors have also identified a further 62 DNA genomic regions that show a similar methylation profile as CD14, ENDRB, HIC and RARB in HSIL samples but not in normal cervical tissue or normal cervical tissue infected with HPV from a panel of 384 candidate genes. These markers are listed in Table 4.

Figure 3:
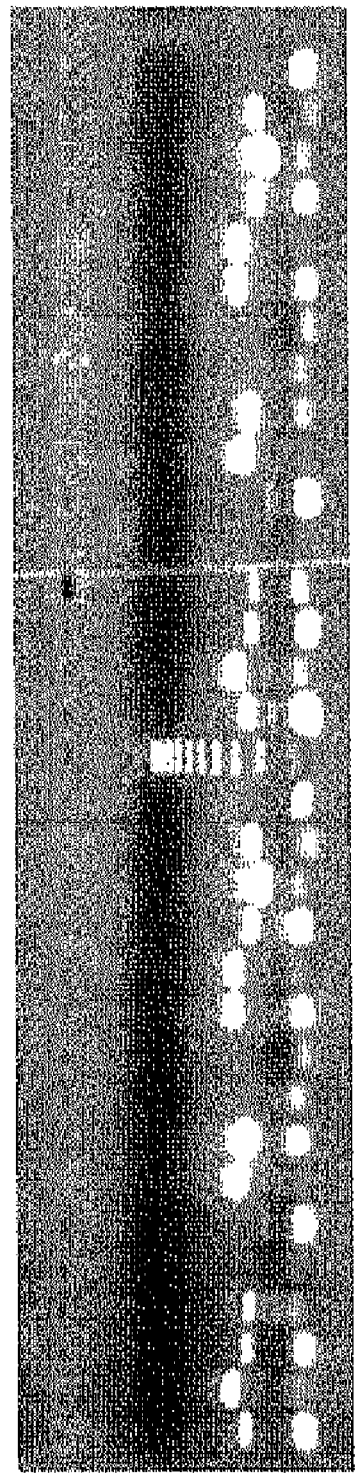
FIG. 3 shows a representative gel of normal cervical samples amplified at 16 different genomic loci, digested with a combination of BstU1 and TaqaI restriction endonuclease, and electrophoresed on an agarose gel. DNA was extracted from liquid based cytology specimens (numbers 28 and 29 here), sodium bisulphite modified and amplified with nested primers to genes identified for further analysis. These genes were, from left to right, 1) TEM 2) MME 3) ECE1 4) SYK 5) RARA 6) HRK 7) GPR37 8) CRBP 9) ABL1 10) RAGE 11) LAMR1 12) MFNG 13) ABCG2 14) TMSBIO 15) SFRS8 and 16) PGR.

FIG. 3 shows a representative gel of normal cervical samples amplified at 16 different genomic loci, digested with a combination of BstU1 and TaqaI restriction endonuclease, and electrophoresed on an agarose gel. DNA was extracted from liquid based cytology specimens (numbers 28 and 29 here), sodium bisulphite modified and amplified with nested primers to genes identified for further analysis. These genes were, from left to right, 1) TEM 2) MME 3) ECE1 4) SYK 5) RARA 6) HRK 7) GPR37 8) CRBP 9) ABL1 10) RAGE 11) LAMR1 12) MFNG 13) ABCG2 14) TMSBIO 15) SFRS8 and 16) PGR.

The pathology and HPV infection profile of the samples were assessed by an expert pathologist. When the CpG dinucleotides within the amplicon were unmethylated, bisulphite modification converts the unmethylated cytosines to a uracil base and after amplification to a thymine base. The unmethylated CpG dinucleotide and the restriction site, is not retained and therefore not recognized by BstU1 (recognises CGCG, which will be converted to TGTG after amplification if the sample is unmethylated but will remain CGCG if the sample contains methylated sequences) or TaqaI (recognises TCGA, which will be converted to TTGA after amplification if the sample is unmethylated but will remain TCGA if the sample contains methylated sequences) endonucleases. Detection of a single band, representing undigested PCR product, therefore implies that the CpG dinucleotide within the amplicon is unmethylated. Methylated CpG dinucleotide is resistant to bisulphite modification so restriction sites recognized by the restriction endonucleases are retained. Consequently the PCR products are digested into multiple frag-

TABLE 4

Genomic regions tested as potential markers together with their corresponding Genbank numbers.

| Genomic | Genbank | Genomic | Genbank | Genomic | Genbank | Genomic | Genbank |
|---|---|---|---|---|---|---|---|
| PGR | AY525610 | NF2 | AF165426 | BMP6 | AF083030 | KRAS2 | M30539 |
| SFRS8 | | XIAPHSX11 | | CDKN1C | U48869 | PLAU | X02419 |
| TMSB10 | M92383 | RARRES1 | | DAB2IP | AL357936 | TNFRSF10B | AB054004 |
| ABCG2 | | FLI1 | AF275879 | LMNB1 | L37737 | CDH1 | |
| MFNG | | HTLF | AC091485 | MMP28 | AF336346 | MAC30 | |
| LAMR1 | | LDHB | X13794 | HAI2 | | DDB2 | |
| RAGE | | RB1 | AF551763 | SOCS1 | DQ086801 | PAX6 | |
| ABL1 | U07563 | TGD | AF545435 | HIC2 | | AXL | |
| CRBP | X07437 | CDK4 | AF507942 | MSH6 | AY082894 | EIF4A2 | |
| GPR37 | AC004925 | MMP14 | AY795074 | RIN2 | AL049538 | SLIT2 | |
| HRK | | RAB32 | AL133539 | HMGA1 | L17131 | RECK | |
| RARA | | BARD1 | AC016708 | JUN | J04111 | TERC | |
| SYK | AL354862 | NF1 | | S100P* | | GATA5 | |
| ECE1 | AL031005 | LIM2 | AF305941 | SRF | AL133375 | STAT1 | |
| MME | M26605 | MMP2 | AY738117 | VDR | AY342401 | | |
| TEM | AL035608 | DAB2 | U41111 | DKK3 | AB035182 | | |

Figure 2:
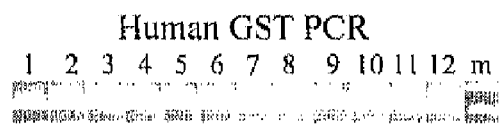
FIG. 2 shows simultaneous detection of Human Genomic DNA and HPV DNA in the same LBC samples
Figure 2:
Figure 2:
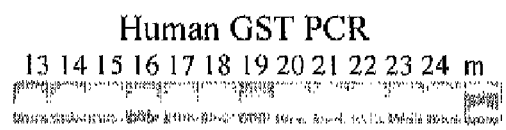
Figure 2:
Figure 2:
Figure 2:

FIG. 2 shows the results of PCR amplification on 36 LBC samples for both human genomic DNA and HPV DNA using the HGS HR-HPV DNA purification and detection kit. As can be seen from the results using this method it is possible to assay for the presence of both human genomic changes and the presence of absence of virus simultaneously.

ments (as indicated by an asterisk) depending on the number of CpG sites available in the amplicon. Detection of an empty lane suggests that the PCR reaction was unsuccessful.

Few multiple bands were detected at these 16 loci. Representative results from this assay are tabulated in Table 5.

TABLE 5

Methylation profiles for DNA samples extracted from pathologically normal cervical samples.

| | Sample ID: | | | | | | | | | | |
|---|---|---|---|---|---|---|---|---|---|---|---|
| | C13 Norm | C14 Norm | C24 Norm | C25 Norm | C26 Norm | C28 Norm | C29 Norm | C18 Norm HPV | C19 Norm HPV | C22 Norm HPV | C42 Norm HPV |
| ABCG2 | U | U | U | U | U | U | U | U | U | U | M |
| MFNG | M | M | U | U | U | U | U | M | M | M | M |
| LAMR1 | U | U | U | U | U | U | U | U | U | M | U |
| HRK | F | U | U | U | U | U | U | U | U | U | U |
| HSX1APF1 | U | U | U | U | U | U | U | U | U | M | F |
| RARRES1 | U | U | U | U | U | U | U | U | U | M | M |
| FLI1 | U | U | U | U | U | U | U | U | U | U | U |
| LDHB | U | F | U | U | U | U | U | U | U | U | F |
| CDK4 | U | U | U | U | U | U | U | U | U | U | U |
| MMP14 | U | F | U | U | U | U | U | U | U | U | C |
| DAB2 | U | U | U | U | U | U | U | U | U | U | U |
| SOCS1 | U | U | U | U | U | U | U | F | U | M | U |
| HIC2 | U | U | U | U | U | U | U | U | U | U | U |
| PLAU | U | F | F | U | U | F | U | F | U | U | M |
| EIF4A2 | U | U | F | F | U | U | U | U | U | U | U |
| SLIT2 | U | U | U | M | M | U | F | M | U | M | U |
| RECK | U | M | U | U | U | U | U | M | U | M | M |
| TERC | F | U | U | U | U | U | F | F | U | M | F |
| GATA5 | M | M | M | M | M | M | M | M | U | M | M |
| STAT1 | U | U | U | U | U | U | U | U | U | U | U |
| HPV Uni | – | – | – | – | – | – | – | + | – | – | – |
| HmGST | U | U | U | U | U | U | U | U | U | U | U |

The methylation profile of a representative number of pathologically normal cervical samples (NORM), some of which were likely to have a HPV infection (NORM HPV). DNA was extracted from a liquid based cytology sample, sodium bisulphite modified and amplified at 384 different genes. The amplicons were digested with restriction enzymes and electrophoresed on an agarose gel. Detection of a single product (an undigested product) indicates that the sample is unmethylated (U) at the promoter region of the gene being interrogated. Detection of multiple bands (a digested product) implies that the sample is methylated (M) at the promoter of the gene being interrogated. The lack of a band at a specific loci (as denoted by "F") infers that the PCR reaction was unsuccessful.

The presence (+) or absence (–) of high and medium risk papilloma viral DNA was also listed. Primers that amplified both the human and mouse GST-P1 gene (HmGST) was included as a control for the PCR reaction. Detection of a band implies that DNA was converted and available for amplification.

Figure 4:
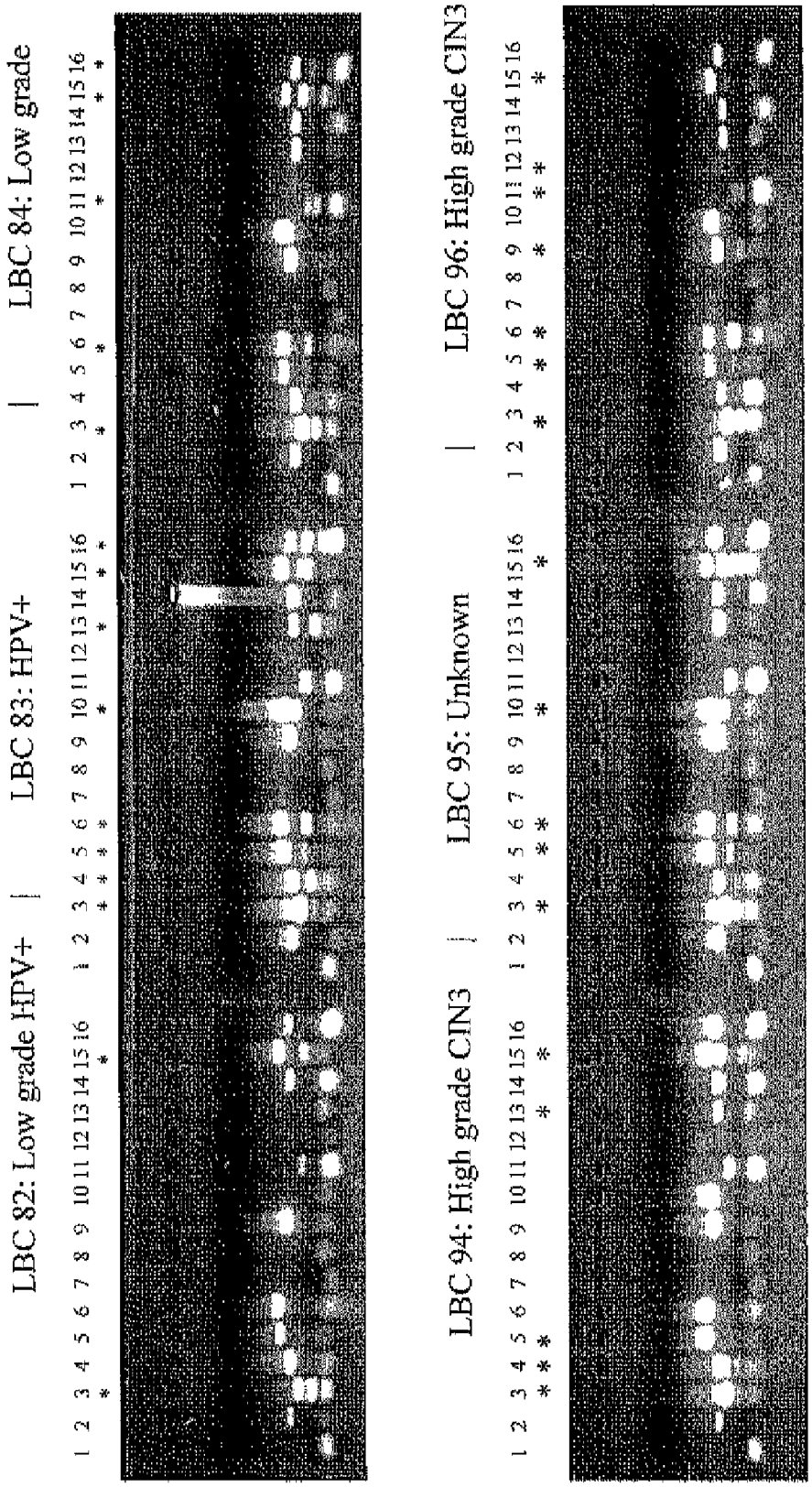
FIG. 4 shows a representative gel of tumour samples amplified at 16 different genomic loci, digested with a combination of BstU1 and Tapl restriction endonuclease and electrophoresed on an agarose gel. DNA was extracted from liquid based cytology specimens (numbers 82, 83, 84, 94, 95 and 96 here), sodium bisulphite modified and amplified with nested primers to genes identified for further analysis. These genes were, from left to right, 1) PGR 2) SFRS8 3) TMSBIO 4) ABCG2 5) MFNG 6) LAMR1 7) RAGE 8) ABU 9) CRBP 10) GPR37 11) HRK 12) RARA 13) SYK 14) ECE1 15) MME and 16) TEM.

FIG. 4 shows a representative gel of tumour samples amplified at 16 different genomic loci, digested with a combination of BstU1 and TaqaI restriction endonuclease and electrophoresed on an agarose gel. DNA was extracted from liquid based cytology specimens (numbers 82, 83, 84, 94, 95 and 96 here), sodium bisulphite modified and amplified with nested primers to genes identified for further analysis. These genes were, from left to right, 1) PGR 2) SFRS8 3) TMSBIO 4) ABCG2 5) MFNG 6) LAMR1 7) RAGE 8) ABL1 9) CRBP 10) GPR37 11) HRK 12) RARA 13) SYK 14) ECE1 15) MME and 16) TEM.

The pathology and HPV infection profile of the samples were assessed by an expert pathologist. When the CpG dinucleotides within the amplicon are unmethylated, bisulphite modification converts the unmethylated cytosines to a uracil base. The unmethylated CpG dinucleotide, and the restriction site, is not retained and therefore not recognized by BstU1 or TaqaI endonucleases. Detection of a single band, representing undigested PCR product, therefore implies that the CpG dinucleotide within the amplicon is unmethylated. Methylated CpG dinucleotide is resistant to bisulphite modification so restriction sites recognized by the restriction endonucleases are retained. Consequently the PCR products are digested into multiple fragments (as indicated by an asterisk) depending on the number of CpG sites available in the amplicon. Detection of an empty lane suggests that the PCR reaction was unsuccessful.

A greater proportion of genes were methylated in tumour samples compared to normal samples (see FIG. 4). Representative results from this assay are tabulated in Table 6.

In Table 6, the methylation profile for a representative number of pathologically abnormal cervical samples (as assessed by an expert pathologist). Samples were classified based on the presence of human papillomavirus (HPV) and the types of lesions (Low-grade LG, Low-grade LG with the papillomavirus LG HPV, Previous high-grade Pr HG, High-grade HG, High grade with a carcinoma in situ 3 component, and carcinoma-in-situ 3 lesion CIN3).

DNA was extracted from a liquid based cytology sample, sodium bisulphite modified and amplified at 384 different genes. The amplicons were digested with restriction enzymes and electrophoresed on an agarose gel. Detection of a single product (an undigested product) is representative of a sample that is unmethylated (U) at the promoter region of the gene being interrogated. Detection of multiple bands (a digested product) is representative of a sample that is methylated (M) at the promoter of the gene being interrogated. The lack of a band at a specific loci (as denoted by "F") infers that the PCR reaction was unsuccessful.

TABLE 6

Methylation profiles for DNA samples extracted from cervical samples with unfavourable pathology

| | C68 HPV | C83 HPV | C85 HPV | C61 LG HPV | C71 LG HPV | C82 LG HPV | C67 LG | C74 LG | C84 LG | C53 Pr HG | C56 Pr HG |
|---|---|---|---|---|---|---|---|---|---|---|---|
| ABCG2 | U | M | U | U | M | U | U | U | U | M | M |
| MFNG | M | M | M | U | F | U | U | F | U | M | M |
| LAMR1 | M | M | U | U | U | U | U | U | U | M | M |
| HRK | U | U | U | F | U | U | U | M | M | U | U |
| HSX1APF1 | U | M | U | F | F | U | M | F | U | U | U |
| RARRES1 | U | M | F | U | F | U | U | U | M | M | M |
| FLI1 | U | M | U | F | U | U | U | F | U | U | M |
| LDHB | U | M | M | F | U | M | U | M | M | M | M |
| CDK4 | U | M | F | F | F | U | M | U | M | M | M |
| MMP14 | U | M | U | U | U | M | U | F | U | M | M |
| DAB2 | M | M | U | U | F | M | U | U | M | U | U |
| SOCS1 | U | M | U | U | M | U | F | M | U | U | M |
| HIC2 | U | M | U | U | M | U | U | U | U | U | U |
| PLAU | M | M | F | F | M | M | F | F | U | U | F |
| EIF4A2 | M | M | U | U | F | M | M | U | M | U | U |
| SLIT2 | U | M | U | U | U | U | U | U | U | U | U |
| RECK | M | M | U | U | F | M | M | F | M | F | M |
| TERC | F | F | F | F | F | F | F | F | F | U | U |
| GATA5 | M | M | U | U | U | M | M | M | M | U | M |
| STAT1 | U | M | U | U | U | U | F | U | U | U | U |
| HPV Uni | − | + | + | + | + | + | + | − | − | − | − |
| HmGST | U | U | U | U | U | U | U | U | U | U | U |

| | C62 Pr HG | C50 HG | C58 HG | C89 HG | C93 HG CIN3 | C94 HG CIN3 | C96 HG CIN3 | C4 CIN3 | C65 CIN3 | C95 |
|---|---|---|---|---|---|---|---|---|---|---|
| ABCG2 | U | M | U | M | M | M | U | U | U | U |
| MFNG | M | M | F | U | M | M | M | M | U | M |
| LAMR1 | F | U | U | U | F | U | M | U | M | M |
| HRK | U | U | U | U | U | U | M | U | M | U |
| HSX1APF1 | F | M | U | U | U | U | U | M | F | U |
| RARRES1 | M | M | M | U | M | M | M | U | U | M |
| FLI1 | F | U | M | U | U | U | U | U | U | M |
| LDHB | U | U | M | M | M | M | U | U | F | M |
| CDK4 | F | M | U | F | U | M | M | F | M | U |
| MMP14 | U | U | U | U | U | M | M | F | U | U |
| DAB2 | F | U | U | M | U | U | M | M | U | M |
| SOCS1 | F | U | F | U | U | U | U | U | U | U |
| HIC2 | M | U | U | U | M | U | U | U | U | U |
| PLAU | M | U | U | U | U | F | U | NT | F | U |
| EIF4A2 | F | U | U | M | M | M | U | NT | M | M |
| SLIT2 | F | U | U | F | M | M | M | NT | U | U |
| RECK | M | U | U | U | U | U | U | NT | U | M |
| TERC | M | U | F | F | F | F | F | NT | F | F |
| GATA5 | M | M | U | M | U | M | M | NT | M | M |
| STAT1 | F | U | U | U | U | U | U | NT | U | U |
| HPV Uni | + | − | − | − | − | − | + | NT | − | + |
| HmGST | U | U | U | U | U | U | U | NT | U | U |

TABLE 7

List of patient pathology

| Sample No | Sample Details |
|---|---|
| C1 | HPV |
| C2 | Ca Endomet |
| C3 | HG CIN3 |
| C4 | CIN3 Cx |
| C5 | AC/AIS |
| C6 | HPV |
| C7 | HPV |
| C8 | NORM |
| C9 | NORM |
| C10 | NORM |
| C11 | NORM |
| C12 | NORM |
| C13 | NORM |
| C14 | NORM |
| C15 | NORM |
| C16 | NORM |
| C17 | NORM |
| C18 | HPV NORM |
| C19 | HPV NORM |
| C20 | NORM |
| C21 | HPV NORM |
| C22 | HPV NORM |
| C23 | NORM |
| C24 | NORM |
| C25 | NORM |
| C26 | NORM |
| C27 | NORM |
| C28 | NORM |

TABLE 7-continued

List of patient pathology

| Sample No | Sample Details |
|---|---|
| C29 | NORM |
| C30 | NORM |
| C31 | NORM |
| C32 | NORM |
| C33 | NORM |
| C34 | NORM |
| C35 | NORM |
| C36 | NORM |
| C37 | NORM |
| C38 | NORM |
| C39 | NORM |
| C40 | NORM |
| C41 | NORM |
| C42 | HPV NORM |
| C43 | NORM |
| C44 | NORM |
| C45 | NORM |
| C46 | NORM |
| C47 | NORM |
| C48 | NORM |
| C49 | HG |
| C50 | HG |
| C51 | Pr HG |
| C52 | HG CIN3 |
| C53 | Pr HG |
| C54 | HG Cx |
| C55 | SSC Cx |
| C56 | Pr HG |
| C57 | AC Cx |
| C58 | HG |
| C59 | HG Cx |
| C60 | HPV |
| C61 | LG HPV |
| C62 | Pr HG |
| C63 | HG |
| C64 | CIN1 HPV |
| C65 | CIN3 |
| C66 | HPV |
| C67 | LG |
| C68 | HPV |
| C69 | HPV |
| C70 | INC HG? |
| C71 | LG HPV |
| C72 | HPV |
| C73 | HPV |
| C74 | LG |
| C75 | HPV |
| C76 | HPV |
| C77 | HPV |
| C78 | SCC |
| C79 | SCC |
| C80 | HPV |
| C81 | INC HG |
| C82 | HPV LG |
| C83 | HPV |
| C84 | LG |
| C85 | HPV |
| C86 | HPV LG |
| C87 | HPV |
| C88 | HPV |
| C89 | HG |
| C90 | HG |
| C91 | HG |
| C92 | HG |
| C93 | HG CIN3 |
| C94 | HG CIN3 |
| C95 | Unknown |
| C96 | HG CIN3 |

Table 7 shows the pathology of samples investigated at 64 different genomic loci for DNA methylation profile.

Liquid Based cytology samples for 96 patients with predetermined pathology were extracted for DNA. The associated pathology of the samples, pertaining to the type of pathology, the degree of invasion and the presence or absence of human papillomavirus infection, were assessed by an expert pathologist.

Samples were labelled as cytologically normal (NORM), with a likely HPV infection (HPV), cytologically normal with a likely HPV infection (HPV NORM), as low grade lesion (LG), as a low grade lesion with HPV infection (LG HPV), as high grade lesion (HG), as increased high-grade lesion (INC HG), as a previous high grade lesions (Pr HG), as a carcinoma in-situ 1 lesion with a likely HPV infection, as a high Grade carcinoma in-situ 3 lesion (HG CIN3), as high grade carcinoma (HG Cx), as squamous cell carcinoma (SCC) as a squamous cell carcinoma/cancer (SCC Cx), as an adenocarcinoma (AC Cx), as an endometrial cancer (Ca Endomet), as an adenocarcinoma/adenocarcinoma in-situ (AC/AIS).

Table 8 shows the genes or genomic regions found by the present inventors to be suitable indicators for disease states by the present invention. It will be appreciated that a person skilled in the art could devise suitable primers or probes to detect changes in one or more of these genes or genomic region is association with detecting the presence of viral nucleic acid.

TABLE 8

Disease genes or genomic regions suitable for the present invention

ABCB1
ABCG2
ABL1(R1)
ABL1(R2)
ABL2
ABO
ADAM23
ADAMTS8
AKT1
ALOX5
ALX3
AMACR
ANXA7
APAF1
APC
APO1
APP
AR
ARHI
ARNT
ASC
ATM
AXIN1
AXL
AXUD1
BAD
BARD1
BCR
BDH
BENE
BIK
BIN1
BIRC5
BLM
BMP2
BMP6
BMPR1A
BRAF
BRCA1
BRCA2
CASPASE-8
CAV1
CBFA2T3
CBFB
CBLC
CCNA1(cycal)
CCND2
CCND3
CD14
CD34

TABLE 8-continued

Disease genes or genomic regions suitable for the present invention

CD44
CD9
CDC20
CDH1
CDH13
CDK10
CDK4
CDKN1A
CDKN1B(p27)
CDKN1C(p57)
CDKN2A
CDKN2A-V2
CDKN2B
CDKN2C
CDKN2D
CDX1
CDX-2
CFTR
CGRP
CHFR
CLDN7
CMYB
CNTN2
COPEB
COX6C
CRBP
CREBBP
CRK
CSPG2
CTNNB1
CX26
CXCL-2
DAB2
DAB2IP
DAPK1
DAPK2
DBCCR1
DCCR
DCK
DDB2
DKK1
DKK3
DLC1
DLK1
DNAJB9
DNMT1
DRG1
DSC3
DUX4
E2F1
ECE1
EDNRB
EFNA4
EGFR
EGR3
EIF4A2
ELAC2
ELK1
ENO3
EP300
EPB41L3
EPHA1
EPHA8
EPO
ERBB2
ERBB4
ERCC4
ESR2
ESR-ALPHA
ETS1
EZH2LONG
FANCF
FASN
FBP
FEZ1
FGF4
FLI1
FLT1
FOLH1
FOS
FOSB
FRA2
FRAT1
FRAT2
FXYD5
GADD45G
GAPD
GATA3
GATA4
GATA5
GATA6
GLTSCR1
GNA13
GNAI1
GNAS
GP9
GPC3
GPR37
GPS1
GRB10
GROS1
GSK3B
GSN
GSTP1
GUSA
H19A
HAI2
HIC-1
HIC-2
HLAG
HMGA1
HOXA11
HOXA13
HOXA5
HOXB5
HOXD13
HOXD8
HPN
HPRT
HPRT1
HRAS
HRK
HSPC070
HSXI1PAF1
HTLF
ID1
IGF2
IGFBP7
IL6
ILK
ING1
INHA
IRF7
JUN
JUNB
JUP
KAI-1
K-ALPHA-1
KIT
KLF4
KPNA3
KRAS2
LAMA3
LAMC2
LAMR1
LATS1
LCK
LDHA
LDHB
LEP1
LIF
LIM2
LMNA1
LMNB1
LOX
LRP2

TABLE 8-continued

Disease genes or genomic regions suitable for the present invention

LRP6
LTF
MAC30
MAD2L1
MADH4
MAGE
MAGE-A3
MAL
MCC
MDGI
MDM2
MFNG
MGMT
MIF
MINT1
MINT25
MINT31
MLH1
MME
MMP14
MMP2
MMP28
MRE11A
MSH2
MSH6
MSLN
MT1G
MT3
MUC1
MYB
MYC
MYCN
MYOD1
MYOG1
N33
NCOA4
NDN
NF1
NF2
NME1
NNAT
NOTCH1
NOV
NROB2
NTRK1
OCLN
OPCML
OXCT
P16
PAX3
PAX5
PAX6
PAX7
PCNA
PDCD2
PDGFD
PENK
PGR
PIM1
PITX2
PLAU
PMS2
PNN
POMC
POU2AF1
PPARG1
PPM1D
PPP2R1B
PRKAR1A
PRKCDBP
PRSS8
PSEN1
PTCH
PTEN
PTGER3
PTGS2
PTPN6
PTPRO

TABLE 8-continued

Disease genes or genomic regions suitable for the present invention

PTTG1IP
PVT1
RAB32
RAB3A
RAB5A
RAD51
RAGE
RARA
RARB
RARRES1
RASSF1
RB1
RBL2
RBM5
RECK
RFC1
RFX1
RGS19IP1
RIN2
RNASE6PL
RUNX3
S100P
SAC2
SCGB3A1
SEMA3B
SFN
SFRP1
SFRP2
SFRS8
SHH
SLC26A4
SLC5A5
SLIT2
SLS5A8
SMARCA3
SMARCB1
SMARCD3
SMOH
SMT3H1
SNCG
SNRPN
SOCS1
SOD1
SOX4
SPARC
SPI7
SRF
SRP72
SSX2
SSX4
STAT1
STAT2
STAT3
STAT4
STK11
SYK
TACSTD
TAGLN
TAUBE-NUSS
TDG
TEM1
TEM8
TERC
TERE1
TERT
TES
TFF1
TFF2
TFP12
TGFBR2
THBS1
THRB
TIG
TIMP3
TJP
TMEFF2
TMSB10
TNC

TABLE 8-continued

Disease genes or genomic regions suitable for the present invention

TNFRSF10B
TNFRSF10C
TNFRSF6
TOP1
TOP2A
TP53
TP53BP2
TP73
TPD52
TPM1
TRA1
TRAF4
TSC2
TSHR
TWIST
VAV
VDR
VEGF
VHL
WFDC1
WT1
YWHAG

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. An assay for screening for potential cervical cancer in a human subject comprising:
    treating a single sample from the human subject with a bisulfite reagent under conditions that cause unmethylated cytosines in human papilloma virus (HPV) nucleic acid in the sample to be converted to uracil to form derivative HPV nucleic acid from the HPV in the sample and cause unmethylated cytosines in human genomic nucleic acid in the sample to be converted to uracil to form derivative human genomic nucleic acid from human genomic nucleic acid in the sample;
    contacting the treated sample with primers capable of binding to regions of derivative HPV nucleic acid, the primers being capable of allowing amplification of a desired HPV-specific nucleic acid molecule of the derivative HPV nucleic acid;
    contacting the treated single sample with primers capable of binding to a region of derivative human genomic nucleic acid, the primers being capable of allowing amplification of the region of derivative human genomic nucleic acid to yield a target genomic specific nucleic acid amplification product, wherein the region of derivative human genomic nucleic acid is derivatized from a region of the human genome in which the methylation status is known to be associated with the potential for cervical cancer in a human subject;
    carrying out an amplification reaction on the treated single sample containing derivative HPV nucleic acid, the derivative human genomic nucleic acid, and the primers; and
    determining potential for cervical cancer in the human subject by assaying for the presence of an amplified HPV-specific nucleic acid product and said target genomic specific nucleic acid amplification product wherein the presence of both an amplified HPV-specific nucleic acid and said target genomic specific nucleic acid amplification product are indicative of a level of risk for cervical cancer.

2. The assay according to claim 1, further comprising testing a sample having the presence of HPV to determine the type, subtype, variant or genotype of the HPV in the sample.

3. The assay according to claim 2 wherein the sample is selected from the group consisting of swab, biopsy, smear, Pap smear, surface scrape, spatula, and fluid samples, as well as samples from different storage media such as frozen material, paraffin blocks, glass slides, forensic collection systems, and archival material.

4. The assay according to claim 1 wherein the bisulphite reagent is sodium bisulphite.

5. The assay according to claim 1 wherein the methylation characteristic is a methylated or unmethylated region of genomic nucleic acid.

6. The assay according to claim 1 wherein the target genomic nucleic acid is selected from the group consisting of regions of CD14, ENDRB, HIC, RARB1, PGR, SFRS8, TMSB10, ABCG2, MFNG, LAMR1, RAGE, ABL1, CRBP, GPR37, HRK, RARA, SYK, ECE1, MME, TEM, NF2, XIAPHSX11, RARRES1, FLI1, HTLF, LDHB, RB1, TGD, CDK4, MMP14, RAB32, BARD1, NF1, LIM2, MMP2, DAB2, BMP6, CDKN1C, DAB2IP, LMNB1, MMP28, HAI2, SOCS1, HIC2, MSH6, RIN2, HMGA1, JUN, S100P*, SRF, VDR, DKK3, KRAS2, PLAU, TNFRSF10B, CDH1, MAC30, DDB2, PAX6, AXL, EIF4A2, SLIT2, RECK, TERC, GATA5, and STAT1.

7. The assay according to claim 1 wherein the primers capable of binding to regions of derivative HPV nucleic acid can produce an amplified HPV-specific nucleic acid product indicative of the presence of HPV types 16, 18, 31, 33, 35, 39, 45, 51, 52, 56, 58, 59, 66 and 68 in a sample.

8. The assay according to claim 1 wherein the primers capable of binding to regions of derivative HPV nucleic acid can produce an amplified HPV-specific nucleic acid product indicative of the presence of HPV types 6, 11, 42, 43, 44, 53, 54 and 55 in a sample.

9. An assay for screening for potential cervical cancer in a human subject comprising:
- contacting a single nucleic acid sample from a human subject with a bisulfite reagent under conditions that cause unmethylated cytosines to be converted to uracil, thereby generating derivative nucleic acids in which said unmethylated cytosines have been converted to uracil;
- performing an amplification reaction on said derivative nucleic acids using primers complementary to portions of derivative nucleic acid from an HPV strain in which unmethylated cytosines have been converted to uracil, wherein said HPV strain is an HPV strain which is associated with an increased risk of cervical cancer and wherein said primers yield an HPV-specific amplification product if said HPV strain is present in said nucleic acid sample;
- performing an amplification reaction on said derivative nucleic acids using primers complementary to portions of a target human derivative sequence in which unmethylated cytosines have been converted to uracil, wherein the target human derivative sequence is derivatized from a region of the human genome in which the methylation status is known to be associated with the potential for cervical cancer in a human subject;
- determining potential for cervical cancer in the human subject by assaying for the presence of an HPV-specific amplification product and an amplification product from said target human derivative sequence wherein the presence of both an HPV-specific amplification product and an amplification product from said target human derivative sequence is indicative of a level of risk for cervical cancer.

10. The method of claim 1, further comprising contacting said target genomic specific nucleic acid amplification product with a restriction enzyme for which cleavage of said amplification product is dependent on the methylation status of said region of the human genome.

11. The method of claim 10, wherein said restriction enzyme is BstU1 or TaqaI.

12. The method of claim 9, further comprising contacting said amplification product from said target human derivative sequence with a restriction enzyme for which cleavage of said amplification product is dependent on the methylation status of said region of the human genome.

13. The method of claim 12, wherein said restriction enzyme is BstU1 or TaqaI.

* * * * *